United States Patent
Parham et al.

(10) Patent No.: US 10,683,453 B2
(45) Date of Patent: Jun. 16, 2020

(54) ORGANIC COMPOUNDS WITH SOLUBLE GROUPS

(71) Applicant: Merck Patent GmbH, Darmstadt (DE)

(72) Inventors: Amir Hossain Parham, Frankfurt am Main (DE); Philipp Stoessel, Frankfurt am Main (DE); Christof Pflumm, Darmstadt (DE); Anja Jatsch, Frankfurt am Main (DE); Joachim Kaiser, Darmstadt (DE); Ewald Aydt, Rossdorf (DE); Dominik Joosten, Frankfurt am Main (DE)

(73) Assignee: Merck Patent GmbH (DE)

(*) Notice: Subject to any disclaimer, the term of this patent is extended or adjusted under 35 U.S.C. 154(b) by 236 days.

(21) Appl. No.: 15/534,325

(22) PCT Filed: Nov. 18, 2015

(86) PCT No.: PCT/EP2015/002311
§ 371 (c)(1),
(2) Date: Jun. 8, 2017

(87) PCT Pub. No.: WO2016/091353
PCT Pub. Date: Jun. 16, 2016

(65) Prior Publication Data
US 2017/0369773 A1   Dec. 28, 2017

(30) Foreign Application Priority Data

Dec. 12, 2014 (EP) ..................... 14004201

(51) Int. Cl.
| | | |
|---|---|---|
| H01L 51/50 | (2006.01) |
| C09K 11/06 | (2006.01) |
| C07D 401/14 | (2006.01) |
| C07C 255/58 | (2006.01) |
| C07D 221/20 | (2006.01) |
| C07D 251/24 | (2006.01) |
| C07D 209/86 | (2006.01) |
| H01L 51/00 | (2006.01) |
| C09B 57/00 | (2006.01) |
| C07C 255/59 | (2006.01) |
| C07D 401/04 | (2006.01) |
| C07D 455/04 | (2006.01) |
| C07D 495/10 | (2006.01) |
| C07D 401/10 | (2006.01) |
| C07D 405/04 | (2006.01) |
| C07D 209/88 | (2006.01) |
| C07D 403/10 | (2006.01) |
| C07D 491/107 | (2006.01) |
| C07D 405/10 | (2006.01) |

(52) U.S. Cl.
CPC ............ *C09K 11/06* (2013.01); *C07C 255/58* (2013.01); *C07C 255/59* (2013.01); *C07D 209/86* (2013.01); *C07D 209/88* (2013.01); *C07D 221/20* (2013.01); *C07D 251/24* (2013.01); *C07D 401/04* (2013.01); *C07D 401/10* (2013.01); *C07D 401/14* (2013.01); *C07D 403/10* (2013.01); *C07D 405/04* (2013.01); *C07D 405/10* (2013.01); *C07D 455/04* (2013.01); *C07D 491/107* (2013.01); *C07D 495/10* (2013.01); *C09B 57/00* (2013.01); *C09B 57/008* (2013.01); *H01L 51/006* (2013.01); *H01L 51/0058* (2013.01); *H01L 51/0061* (2013.01); *H01L 51/0072* (2013.01); *H01L 51/0073* (2013.01); *C07C 2603/18* (2017.05); *C09K 2211/1007* (2013.01); *C09K 2211/1011* (2013.01); *C09K 2211/1014* (2013.01); *C09K 2211/1018* (2013.01); *C09K 2211/1029* (2013.01); *C09K 2211/1059* (2013.01); *C09K 2211/1088* (2013.01); *H01L 51/0051* (2013.01); *H01L 51/0056* (2013.01); *H01L 51/0067* (2013.01); *H01L 51/5012* (2013.01); *H01L 51/5072* (2013.01); *H01L 51/5096* (2013.01); *Y02E 10/549* (2013.01); *Y02P 70/521* (2015.11)

(58) Field of Classification Search
None
See application file for complete search history.

(56) References Cited

U.S. PATENT DOCUMENTS

| | | |
|---|---|---|
| 8,993,129 B2 | 3/2015 | Endo et al. |
| 9,126,970 B2 | 9/2015 | Pflumm et al. |
| 9,133,119 B2 | 9/2015 | Parham et al. |
| 9,660,198 B2 | 5/2017 | Nakagawa et al. |
| 9,666,806 B2 | 5/2017 | Anemian et al. |
| 10,006,079 B2 | 6/2018 | Clouatre et al. |

(Continued)

FOREIGN PATENT DOCUMENTS

| | | |
|---|---|---|
| DE | 102009023155 A1 | 12/2010 |
| EP | 2182040 A2 | 5/2010 |

(Continued)

OTHER PUBLICATIONS

Tao, Y., et al., "Thermally Activated Delayed Fluorescence Materials Towards the Breakthrough of Organoelectronics", Advanced Materials, 2014, vol. 26, pp. 7931-7958.

(Continued)

*Primary Examiner* — Gregory D Clark
(74) *Attorney, Agent, or Firm* — Faegre Drinker Biddle & Reath LLP

(57) ABSTRACT

The present invention relates to soluble organic compounds, to compositions comprising these compounds, to formulations comprising the compounds or compositions, and to electronic devices.

18 Claims, No Drawings

(56) References Cited

U.S. PATENT DOCUMENTS

| | | |
|---|---|---|
| 10,193,079 B2 | 1/2019 | Stoessel et al. |
| 10,249,828 B2 | 4/2019 | Stoessel et al. |
| 2016/0093812 A1 | 3/2016 | Stoessel et al. |
| 2016/0130225 A1* | 5/2016 | Tasaki .................. C07D 209/80 257/40 |
| 2016/0181545 A1 | 6/2016 | Stoessel et al. |

FOREIGN PATENT DOCUMENTS

| | | |
|---|---|---|
| EP | 2599773 A1 | 6/2013 |
| JP | 2013504884 A | 2/2013 |
| JP | 2013527989 A | 7/2013 |
| JP | 2013253121 A | 12/2013 |
| WO | WO-2011070963 A1 | 6/2011 |
| WO | WO-2011088877 A1 | 7/2011 |
| WO | WO-2013011954 A1 | 1/2013 |
| WO | WO-2014128945 A1 | 8/2014 |
| WO | WO-2014146752 A1 | 9/2014 |
| WO | WO-2014166584 A1 | 10/2014 |
| WO | WO-2014166585 A1 | 10/2014 |
| WO | WO-2014166586 A1 | 10/2014 |
| WO | WO-2014194971 A1 | 12/2014 |

OTHER PUBLICATIONS

International Search Report for PCT/EP2015/002311 dated Feb. 12, 2016.
Written Opinion of the International Searching Authority for PCT/EP2015/002311 dated Feb. 12, 2016.

* cited by examiner

ORGANIC COMPOUNDS WITH SOLUBLE GROUPS

CROSS-REFERENCE TO RELATED APPLICATIONS

This application is a national stage application (under 35 U.S.C. § 371) of PCT/EP2015/002311, filed Nov. 18, 2015, which claims benefit of European Application No. 14004201.1, filed Dec. 12, 2014, both of which are incorporated herein by reference in their entirety.

The present invention relates to organic compounds having a small singlet-triplet gap, to compositions and formulations comprising these compounds, to electronic devices comprising the compounds or compositions, and to processes for producing the devices.

The structure of a specific electronic device in which organic semiconductors are used as functional materials is described, for example, in U.S. Pat. Nos. 4,539,507, 5,151, 629, EP 0676461 and WO 98/27136. These devices are organic light-emitting diodes (OLEDs), a specific group of organic electroluminescent devices. Emitting materials used here are especially also organometallic iridium and platinum complexes which exhibit phosphorescence rather than fluorescence (M. A. Baldo et al., Appl. Phys. Lett. 1999, 75, 4-6). For quantum-mechanical reasons, up to four times the energy efficiency and power efficiency is possible using organometallic compounds as phosphorescent emitters.

In spite of the good results which are achieved with organometallic iridium and platinum complexes, however, they also have a number of disadvantages: for instance, iridium and platinum are scarce and costly metals. It would therefore be desirable for conservation of resources to be able to avoid the use of these scarce metals. Furthermore, some metal complexes of this kind have lower thermal stability than purely organic compounds, and so it would be advantageous for this reason too to use purely organic compounds, if they lead to comparably good efficiencies. Furthermore, iridium or platinum emitters that phosphoresce in the blue, especially deep blue, and have high efficiency and lifetime are technically difficult to achieve, and so there is a need for improvement here too. Furthermore, there is a need for improvement especially in the case of the lifetime of phosphorescent OLEDs containing Ir or Pt emitters when the OLED is operated at relatively high temperature, as required for some applications. Furthermore, many of the known organic semiconductor materials are applied by vapour deposition by means of sublimation under reduced pressure for production of electronic devices, which is very inconvenient and costly in some cases. Moreover, it is not possible to apply all materials by vapour deposition, and so particular organic materials, in spite of good optoelectronic properties, cannot be used in electronic devices because of their poor processability. Particularly for the mass production of electronic products, inexpensive processibility of organic materials is of very great commercial interest. Therefore, highly efficient organic molecules processible from solution are desirable.

An alternative to the development of phosphorescent metal complexes is the use of emitters which exhibit thermally activated delayed fluorescence (TADF) (e.g. H. Uoyama et al., Nature 2012, vol. 492, 234). These are organic materials in which the energy gap between the lowest triplet state $T_1$ and the first excited singlet state $S_1$ is so small that this energy gap is smaller than or in the region of the thermal energy. For quantum-statistical reasons, on electronic excitation in the OLED, 75% of the excited states are in the triplet state and 25% in the singlet state. Since purely organic molecules cannot usually emit from the triplet state, 75% of the excited states cannot be utilized for emission, as a result of which it is possible in principle to convert only 25% of the excitation energy to light. If, however, the energy gap between the lowest triplet state and the lowest excited singlet state is not greater or not significantly greater than the thermal energy described by $k_B T$ where $k_B$ is the Boltzmann constant and T is the temperature, the first excited singlet state of the molecule is accessible from the triplet state by thermal excitation and can be populated thermally. Since this singlet state is an emissive state from which fluorescence is possible, this state can be used to generate light. Thus, in principle, the conversion of up to 100% of the electrical energy to light is possible when purely organic materials are used as emitter. Thus, the prior art describes an external quantum efficiency of more than 19%, which is within the same order of magnitude as for phosphorescent OLEDs. It is thus possible with purely organic materials of this kind to achieve very good efficiencies and at the same time to avoid the use of scarce metals such as iridium or platinum. In addition, it is also possible with such materials to achieve high-efficiency blue-emitting OLEDs.

The compounds that exhibit TADF and are described in the prior art are all applied by vapour deposition by means of sublimation under reduced pressure, in order to produce electronic devices comprising these compounds.

In general, there is still considerable need for improvement in the case of the compounds from the prior art, especially with regard to processibility. Moreover, the inventive compounds described further down exhibit elevated air stability compared to the organic metal complexes. Finally, the inventive compounds processed from solution lead to electronic devices, especially organic electroluminescent devices, which exhibit fewer short circuits.

The technical problem underlying the present invention is thus that of providing compounds having good performance data in electronic devices, which avoid the use of metals in metal complexes and can be processed from solution.

It has been found that, surprisingly, the compounds described in detail further down eliminate the disadvantage from the prior art and lead to efficient electronic devices which can be processed easily from solution and are thus suitable for inexpensive mass production of electronic devices.

The present invention therefore provides such organic compounds, compositions and formulations comprising these compounds, and electronic devices, especially organic electroluminescent devices, comprising these compounds and compositions, and processes for producing the devices.

The present invention provides an organic compound which has a gap between the first excited triplet state ($T_1$) and the first excited singlet state ($S_1$) of not more than 0.15 eV, characterized in that the organic compound contains at least one solubilizing group.

Triplet and singlet states and the energies of HOMOs (highest occupied molecular orbitals) and LUMOs (lowest unoccupied molecular orbitals) are determined in the present case with the aid of a quantum chemistry method disclosed in detail in the examples section.

There follows a detailed description of the luminescent organic compound having a gap between the lowest triplet state $T_1$ and the first excited singlet state $S_1$ of ≤0.15 eV. This is a compound which exhibits TADF (thermally activated delayed fluorescence). This compound is abbreviated in the description which follows to "TADF compound".

The organic TADF compound according to the invention is a carbon compound which does not contain any metals. More particularly, the TADF compound according to the invention is an organic compound formed from the elements C, H, D, B, Si, N, P, O, S, F, Cl, Br and I.

Preferably, the organic TADF compound according to the invention has a gap between $S_1$ and $T_1$ of not more than 0.12 eV, more preferably of not more than 0.10 eV, even more preferably of not more than 0.08 eV and especially preferably of not more than 0.05 eV.

In a preferred embodiment, the $S_1$ level of the organic TADF compound has a higher energy than the $T_1$ level. In that case, the gap between the $S_1$ and $T_1$ energy levels is defined as follows: $\Delta E = E(S_1) - E(T_1)$ where $\Delta E$ is not more than 0.15 eV, preferably not more than 0.12 eV, more preferably not more than 0.10 eV, even more preferably not more than 0.08 eV and especially preferably not more than 0.05 eV.

Singlet and triplet energies are determined in the present case with the aid of quantum chemistry methods which are disclosed in a general and detailed manner in the examples section.

In a preferred embodiment, the organic TADF compound is an organic compound of the general formula (1)

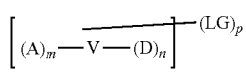

Formula (1)

where the symbols and indices used are as follows:
m is an integer selected from 1, 2, 3, 4 and 5;
n is an integer selected from 1, 2, 3, 4 and 5;
p is an integer equal to 1 or greater than 1; preferably, p is an integer from 1 to 12, very preferably an integer from 1 to 10, very particularly preferably an integer from 1 to 8, especially preferably an integer from 1 to 6 and further preferably an integer from 1 to 4;
A is an acceptor group which may be substituted by one or more $R^1$ radicals which may be the same or different at each instance;
D is a donor group which may be substituted by one or more $R^1$ radicals which may be the same or different at each instance;
LG is a solubilizing group which may be bonded to A, D and/or V, and is preferably bonded to the A and/or D groups and is very preferably bonded to the D group;
V is any organic bridge between the A and D groups or a single bond, where either m or n is 1 when V is a single bond, where V may be substituted by one or more $R^1$ radicals which may be the same or different at each instance;
$R^1$ is the same or different at each instance and is hydrogen, a straight-chain alkyl, alkoxy or thioalkoxy group having 1 to 40 carbon atoms or a branched or cyclic alkyl, alkoxy or thioalkoxy group having 3 to 40 carbon atoms or a silyl group or a substituted keto group having 1 to 40 carbon atoms, an alkoxycarbonyl group having 2 to 40 carbon atoms, an aryloxycarbonyl group having 7 to 40 carbon atoms, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where two or more of the $R^1$ groups may together form a mono- or polycyclic, aliphatic or aromatic ring system, it being preferable when no two or more of the $R^1$ groups can together form a mono- or polycyclic, aliphatic or aromatic ring system.

It is further preferable that the compound of the general formula (1) contains at least 2, preferably at least 3, very preferably at least 4, even more preferably at least 5 and especially at least 6 aromatic rings.

In a further preferred embodiment, the organic TADF compound is an organic compound having a molecular weight of not more than 5000 g/mol, very preferably of not more than 4000 g/mol, more preferably of not more than 3000 g/mol, even more preferably of not more than 2000 g/mol, especially preferably of not more than 1500 g/mol and even more preferably of not more than 1000 g/mol.

The acceptor group A (also called acceptor substituent) in the present case is understood to mean a group which is an electron acceptor group. What is meant by an acceptor group is well known to those skilled in the art. It is preferable when the acceptor group has a negative inductive effect (−I) and/or a negative mesomeric effect (−M). The determination of these properties with the aid of the Hammett equation is well known to those skilled in the art. Suitable acceptor substituents are especially cyano groups, nitriles, pyrimidines, pyrazines, =O (oxo group, for example ketones), but also $CF_3$ and, for example, electron-deficient heteroaryl groups which may also have further substitution. Preferred acceptor groups A here are cyano groups and oxo groups, and cyano groups are very preferred. Examples of preferred electron-deficient heteroaryl groups are selected from the group consisting of triazines, pyrimidines, phosphine oxides and ketones.

The donor group D (also called donor substituent) in the present case is understood to mean a group which is an electron donor group. What is meant by a donor group is well known to those skilled in the art. It is preferable when the donor group has a positive inductive effect (+I) and/or a positive mesomeric effect (+M). The determination of these properties with the aid of the Hammett equation is well known to those skilled in the art. Suitable donor substituents are especially diaryl- or -heteroarylamino groups and carbazole groups or carbazole derivatives, such as indenocarbazoles or indolocarbazoles, which are each preferably bonded via N to the bridge V or to the group A. These groups may also have further substitution.

A solubilizing group LG is understood in the present context to mean a group which increases the solubility of organic semiconductor materials in organic solvents, such that it is possible to produce layers from solution having a layer thickness between 10 and 400 nm, preferably between 10 and 200 nm.

Solubilities of the compounds according to the invention are determined in the context of the present invention by the method described in the examples section.

In a preferred embodiment of the present invention, LG is selected from the group consisting of
a straight-chain alkyl or alkoxy group having 2 to 40 carbon atoms, preferably having 2 to 30 carbon atoms, very preferably having 2 to 20 carbon atoms, even more preferably having 2 to 15 carbon atoms and especially preferably having 3 to 15 carbon atoms,
a branched or cyclic alkyl or alkoxy group having 3 to 40 carbon atoms, preferably having 3 to 30 carbon atoms, very preferably having 3 to 20 carbon atoms, even more preferably having 3 to 15 carbon atoms and especially preferably having 3 to 10 carbon atoms,
an aromatic or heteroaromatic ring system having 3 or more aromatic or heteroaromatic rings which may be substituted by one or more identical or different $R^1$ radicals;

an aromatic or heteroaromatic ring system having 1 or 2 aromatic or heteroaromatic rings substituted in the ortho position by one or more identical or different $R^1$ radicals other than H, where the rings may be substituted by further identical or different $R^1$ radicals.

In a very preferred embodiment, LG is a group of the formula (LG-1)

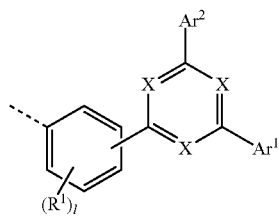

Formula (LG-1)

where the symbols used are as follows:
$Ar^1$, $Ar^2$ are each independently an aryl or heteroaryl group which may be substituted by one or more $R^1$ radicals,
X is in each case independently N or $CR^2$, where not more than one of the three X groups may be an N; all three X groups are $CR^2$ and X is very preferably CH,
$R^1$, $R^2$ are each independently hydrogen, a straight-chain alkyl, alkoxy or thioalkoxy group having 1 to 40 carbon atoms or a branched or cyclic alkyl, alkoxy or thioalkoxy group having 3 to 40 carbon atoms or a silyl group or a substituted keto group having 1 to 40 carbon atoms, an alkoxycarbonyl group having 2 to 40 carbon atoms, an aryloxycarbonyl group having 7 to 40 carbon atoms, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where two or more of the $R^1$ and/or $R^2$ groups may form a mono- or polycyclic, aliphatic or aromatic ring system with one another and/or with the ring to which the $R^1$ group is bonded; and
l is 0, 1, 2, 3 or 4;
where the dotted bond indicates the bond to the functional structural element.

If the $Ar^1$ and $Ar^2$ groups are heteroaryl groups, it is preferable that each heteroaryl group has not more than one heteroatom.

It is preferable when neither of the $R^1$ and/or $R^2$ groups in the formula (LG-1) can form a mono- or polycyclic, aliphatic or aromatic ring system with one another and/or with the ring to which the $R^1$ group is bonded.

Unless a different definition has been given elsewhere, an aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example pyridine, thiophene, etc., or a fused (annelated) aryl or heteroaryl group, for example naphthalene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or $CH_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups according to the present invention may be straight-chain, branched or cyclic, where one or more nonadjacent $CH_2$ groups may be replaced by the abovementioned groups; in addition, it is also possible for one or more hydrogen atoms to be replaced by D, F, Cl, Br, I, CN or $NO_2$, preferably F, Cl or CN, further preferably F or CN, especially preferably CN.

An aromatic or heteroaromatic ring system which has 5-30 or 5-60 aromatic ring atoms and may also be substituted in each case by the abovementioned R, $R^1$ or $R^2$ radicals is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

It is preferable when the phenylene group of the formula (LG-1) has ortho or meta linkage, very particular preference being given to meta linkage according to the following formula (LG-2):

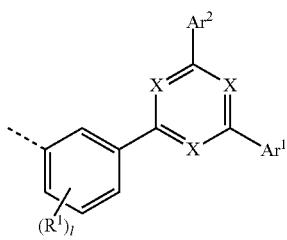

Formula (LG-2)

In a particularly preferred embodiment of the present invention, LG is delimited from the acceptor groups; in other words, the LG groups do not contain any electron-deficient groups, i.e., more particularly, no electron-deficient heteroaromatics either.

Examples of particularly preferred LG groups are listed in the table which follows, where the groups may have further substitution by one or more identical or different $R^1$ radicals, where it is optionally possible for two or more adjacent $R^1$ substituents to form a monocyclic or polycyclic, aliphatic, aromatic or heteroaromatic ring system; preferably, no two or more adjacent $R^1$ substituents form a monocyclic or polycyclic, aliphatic, aromatic or heteroaromatic ring system.

Formula (LG-3)

Formula (LG-4)

Formula (LG-5)

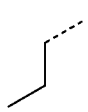

Formula (LG-6)

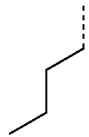

Formula (LG-7)

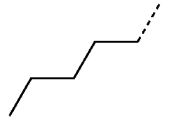

Formula (LG-8)

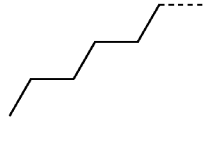

Formula (LG-9)

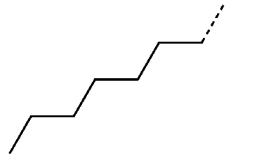

Formula (LG-10)

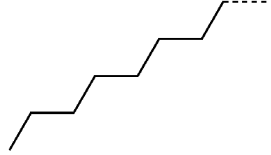

Formula (LG-11)

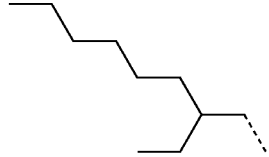

Formula (LG-12)

Formula (LG-13)

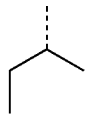

Formula (LG-14)

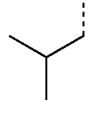

Formula (LG-15)

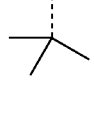

Formula (LG-16)

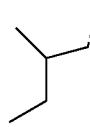

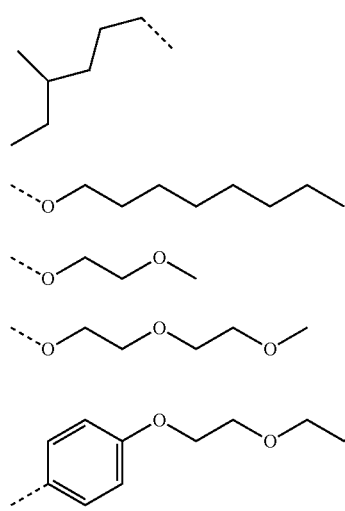

Formula (LG-36)
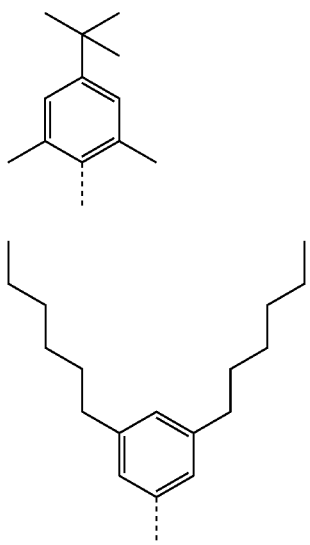
Formula (LG-37)
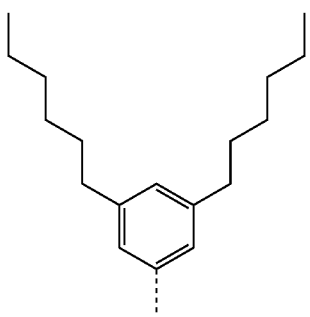
Formula (LG-38)
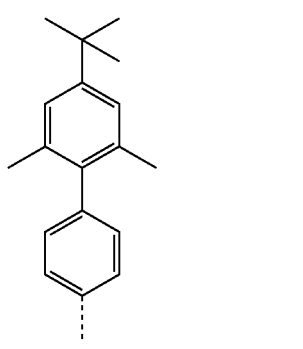
(Formula LG-39)
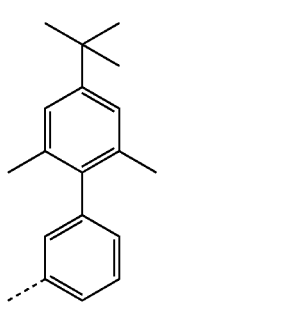
(Formula LG-40)
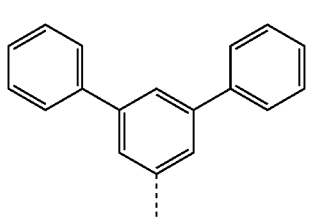
(Formula LG-41)
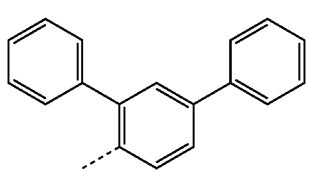
(Formula LG-42)
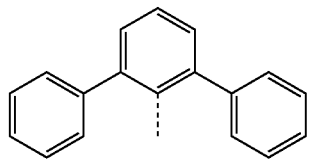
(Formula LG-43)
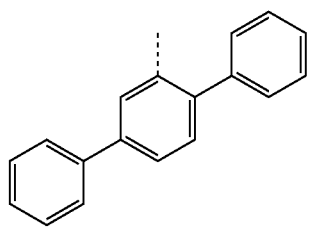
(Formula LG-44)
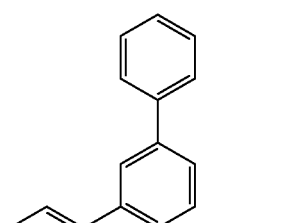
(Formula LG-45)
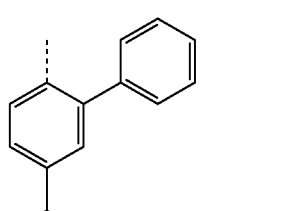
(Formula LG-46)
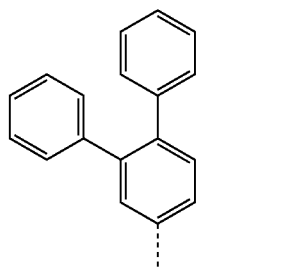
(Formula LG-47)
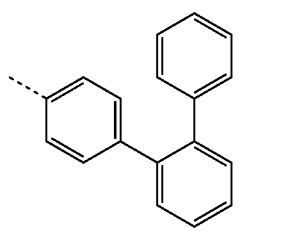

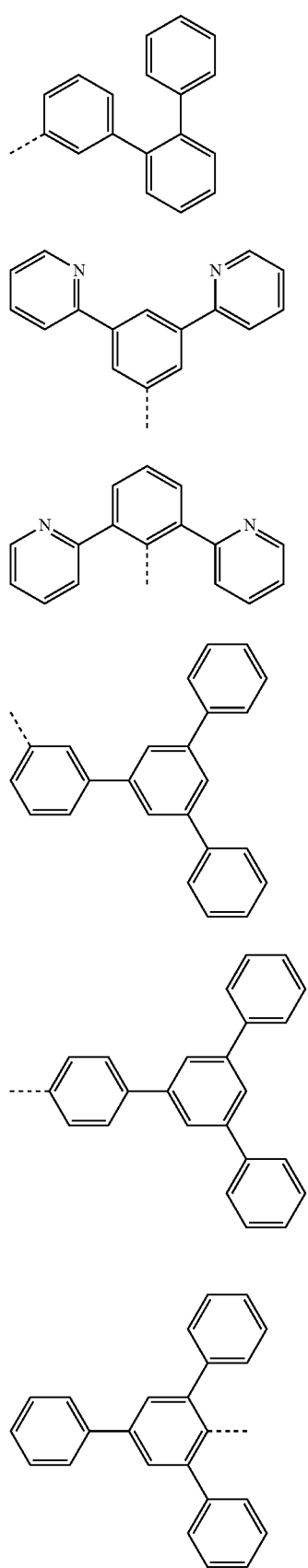

(Formula LG-48)

(Formula LG-49)

(Formula LG-50)

(Formula LG-51)

(Formula LG-52)

(Formula LG-53)

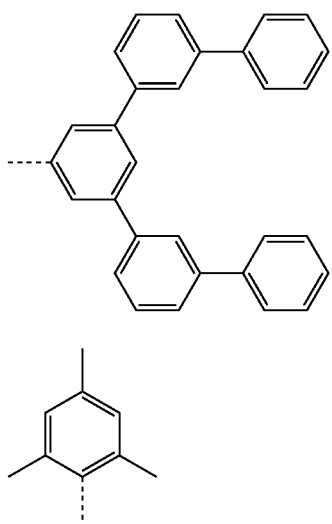

(Formula LG-54)

(Formula LG-27a)

(Formula LG-55)

A further preferred soluble LG group has the formula —N(X³)(X⁴) where at least one of the two $X^3$ and $X^4$ groups is one of the abovementioned soluble groups (LG-1) to (LG-55), it being very preferable when the two $X^3$ and $X^4$ groups are selected from the abovementioned soluble groups (LG-1) to (LG-55). It is particularly preferable when both $X^3$ and $X^4$ groups are selected from the abovementioned soluble groups (LG-1) to (LG-55) and are additionally identical.

If only one of the two $X^3$ and $X^4$ groups is one of the groups (LG-1) to (LG-55), the other group is preferably an aryl or heteroaryl group which may be substituted by one or more $R^1$ radicals, it being very preferable when the group is a phenyl, biphenyl, terphenyl or quaterphenyl group which may be substituted by one or more $R^1$ radicals, it being especially preferable when the group is an unsubstituted phenyl, biphenyl, terphenyl or quaterphenyl group.

Further preferred LG groups are those which are obtained by bonding one or more of the abovementioned groups (LG-1) to (LG-55) to a phenylene group. For example, it is possible with the aid of the group (LG-8) to form the following solubilizing groups as well:

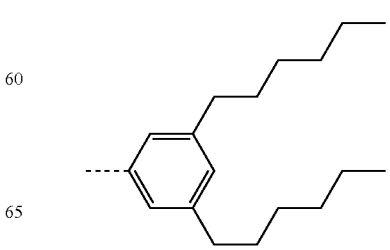

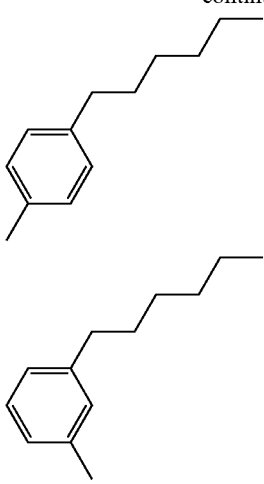

Preferred LG groups are thus also those of the following formula (LGX):

Formula (LGX)

where the index x is an integer from 1 to 5, the index x preferably being 1 or 2;
BX is the same or different and is a group of the formulae (LG-1) to (LG-55).

Preference is further given to those LG groups which contain one of the groups of the formulae (LG-1) to (LG-55) or (LGX).

In a preferred embodiment of the present invention, the bridge V is selected from one of the following groups, where the groups as specified above may be substituted by one or more A groups and by one or more D groups and by one or more $R^1$ radicals which may be the same or different at each instance.

Formula (V-1)

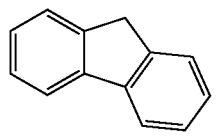

Formula (V-2)

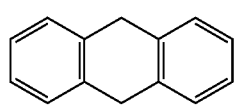

Formula (V-3)

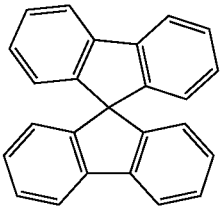

Formula (V-4)

Formula (V-5)

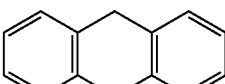

Formula (V-6)

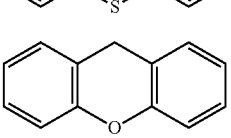

Formula (V-7)

In a preferred embodiment, the compound of the general formula (1) contains, in the A and D groups and the groups of the formulae (LG-1) to (LG-55), preferably 3 to 15, very preferably 3 to 12, even more preferably 3 to 10 and especially 4 to 10 aromatic rings.

It is further preferable when the compound of the formula (1) contains at least one heterocyclic ring.

Very preferably, the compound of the general formula (1) contains at least one heteroaromatic ring or a heteroaromatic ring system.

The TADF compound is preferably an aromatic compound having both donor and acceptor substituents, with only slight spatial overlap between the LUMO and the HOMO of the compound. What is meant by donor and acceptor substituents is known in principle to those skilled in the art and has already been elucidated above. Suitable donor substituents are especially diaryl- or -heteroarylamino groups and carbazole groups or carbazole derivatives, each preferably bonded to the aromatic compound via N. These groups may also have further substitution. Suitable acceptor substituents are especially cyano groups, but also, for example, electron-deficient heteroaryl groups which may also have further substitution.

In a preferred embodiment, the present invention relates to an organic TADF compound of the general formula (1) having a small spatial overlap of the molecular orbitals Λ involved in particular electronic transitions (charge transfer states).

The overlap of the molecular orbitals Λ in the present case is determined by means of a quantum chemistry method which is disclosed in detail in the examples section.

In the present case, a small overlap in the molecular orbitals means that the value of the parameter Λ is 0.3 or less, preferably 0.2 or less, very preferably 0.15 or less, even more preferably 0.1 or less and especially preferably 0.05 or less.

Orbital energies and the overlap of the molecular orbitals are determined in the present case with the aid of quantum chemistry methods which are disclosed in a general and detailed manner in the examples section.

It is additionally preferable when the organic TADF compound has a short decay time. The decay time is preferably not more than 50 μs. The way in which the determination of the decay time is conducted in the context of the present invention is disclosed in a general and detailed manner in the examples section.

Particularly preferred TADF compounds in the context of the present invention are those of the general formula (2)

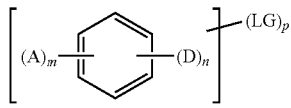

Formula (2)

where the indices and symbols used have the abovementioned definitions. In addition, preferred embodiments disclosed elsewhere in the present invention for the indices and symbols also constitute preferred embodiments for the compound of the formula (2).

The one or more LG groups are preferably bonded here to the one or more D groups.

Very particularly preferred TADF compounds are those of the formula (3) in which pp is 1, 2 or 3, pp preferably being 1 or 2 and pp very preferably being 2.

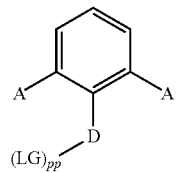

Formula (3)

Especially preferred TADF compounds are those of the formula (4).

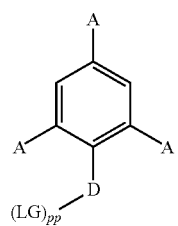

Formula (4)

Further especially preferred TADF compounds are those of the formula (5) where pp may be the same or different at each instance; q', q" and q''' are each independently 0 or 1, where the sum total of q'+q"+q''' is 1, 2 or 3.

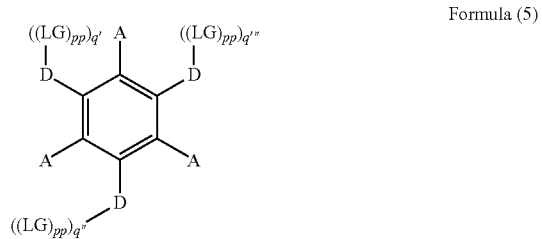

Formula (5)

Further especially preferred TADF compounds are those of the formula (6) where pp may be the same or different at each instance; q', q", q''' and q'''' are each independently 0 or 1, where the sum total of q'+q"+q'''+q'''' is 1, 2, 3 or 4.

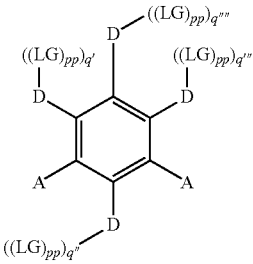

Formula (6)

Further especially preferred TADF compounds are those of the formula (7) where pp may be the same or different at each instance; q' and q" are each independently 0 or 1, where the sum total of q'+q" is 1 or 2.

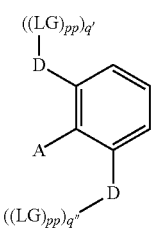

Formula (7)

Further especially preferred TADF compounds are those of the formula (8) where pp may be the same or different at each instance; q', q" and q''' are each independently 0 or 1, where the sum total of q'+q"+q''' is 1, 2 or 3.

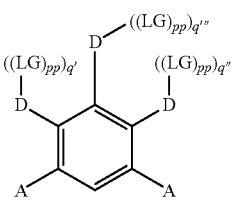

Formula (8)

It is further especially preferable when A in the compounds of the formulae (2) to (8) is CN. It is even more preferable when A in the compounds of the formulae (2) to (8) is CN and D is a carbazole, where the carbazole may have further substitution by one or more $R^1$ radicals.

Particularly preferred TADF compounds in the context of the present invention are those of the general formula (9) where the spirobifluorene may be substituted by one or more $R^1$ radicals which may be the same or different at each instance

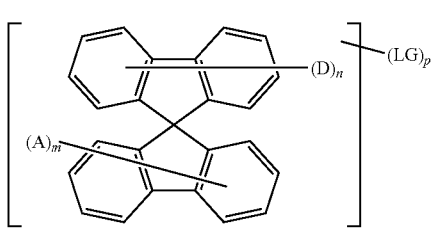

Formula (9)

where the indices and symbols used have the abovementioned definitions. In addition, preferred embodiments disclosed elsewhere in the present invention for the indices and symbols also constitute preferred embodiments for the compound of the formula (9). Formula (9) makes it clear that A and D are bonded on different sides in the Spiro compound.

Very particularly preferred TADF compounds are also those of the formula (10).

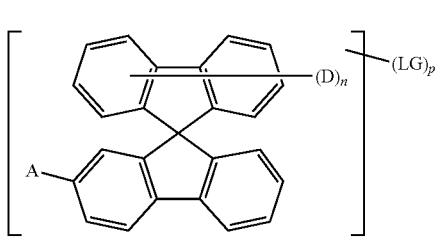

Formula (10)

Especially preferred TADF compounds are those of the formula (11) in which pp is 1, 2 or 3, pp preferably being 1 or 2 and pp very preferably being 2.

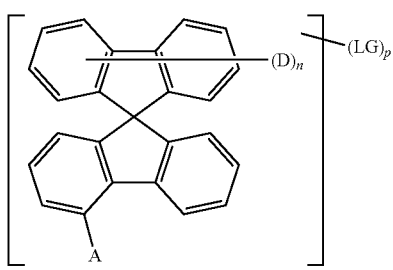

Formula (11)

Further very particularly preferred TADF compounds are also those of the formula (12).

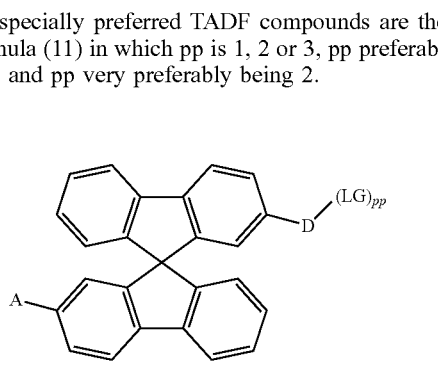

Formula (12)

Especially preferred TADF compounds are those of the formula (13) in which pp is 1, 2 or 3, pp preferably being 1 or 2 and pp very preferably being 2.

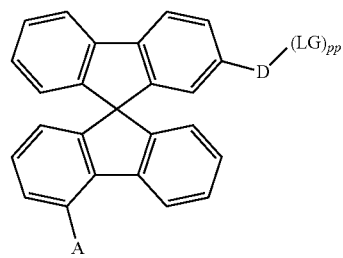

Formula (13)

Further very particularly preferred TADF compounds are those of the formula (14).

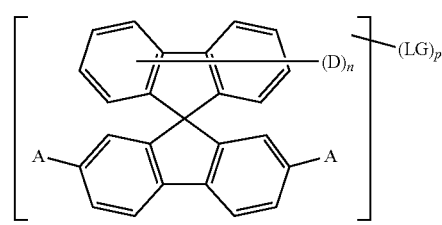

Formula (14)

Especially preferred TADF compounds are those of the formula (15) where pp may be the same or different at each instance; q' and q" are each independently 0 or 1, where the sum total of q' q" is 1 or 2.

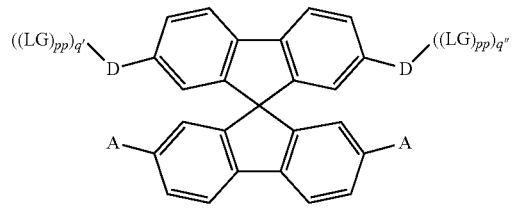

Formula (15)

Additionally especially preferred TADF compounds are those of the formula (16) in which pp is 1, 2 or 3, pp preferably being 1 or 2 and pp very preferably being 2.

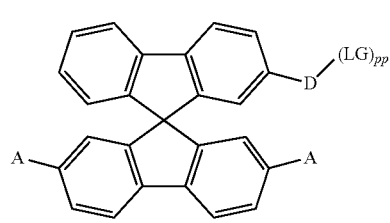

Formula (16)

Additionally very particularly preferred TADF compounds are those of the formula (17).

Formula (17)

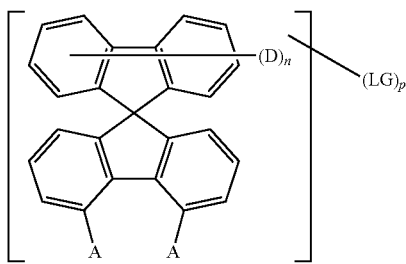

Especially preferred TADF compounds are those of the formula (18) where pp may be the same or different at each instance; q' and q" are each independently 0 or 1, where the sum total of q'+q" is 1 or 2.

Formula (18)

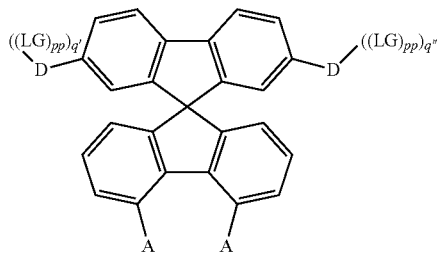

Further especially preferred TADF compounds are those of the formula (19) in which pp is 1, 2 or 3, pp preferably being 1 or 2 and pp very preferably being 2.

Formula (20)

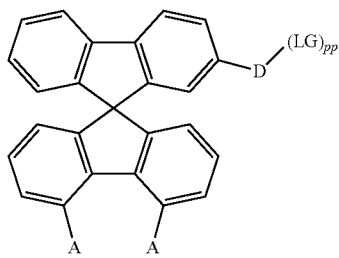

Additionally very particularly preferred TADF compounds are those of the formula (21).

Formula (21)

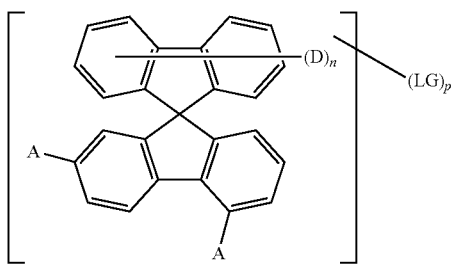

Especially preferred TADF compounds are those of the formula (22) where pp may be the same or different at each instance; q' and q" are each independently 0 or 1, where the sum total of q' q" is 1 or 2.

Formula (22)

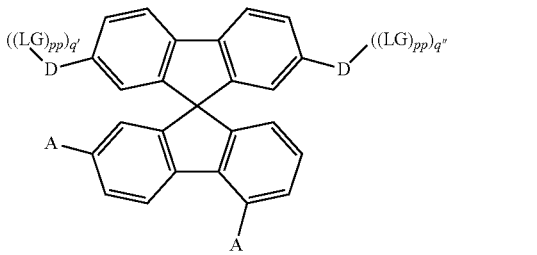

Further especially preferred TADF compounds are those of the formula (23) in which pp is 1, 2 or 3, pp preferably being 1 or 2 and pp very preferably being 2.

Formula (23)

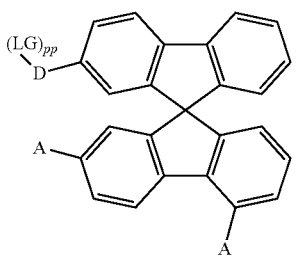

Additionally especially preferred TADF compounds are those of the formula (24) in which pp is 1, 2 or 3, pp preferably being 1 or 2 and pp very preferably being 2.

Formula (24)

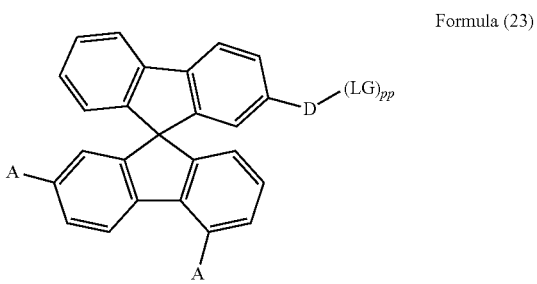

The one or more LG groups in the compounds of the formulae (6) to (24) bind here preferentially to D group(s).

Very particularly preferred TADF compounds are also those of the formula (25).

Formula (25)

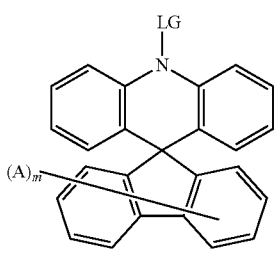

Further very particularly preferred TADF compounds are those of the formula (26).

Formula (26)

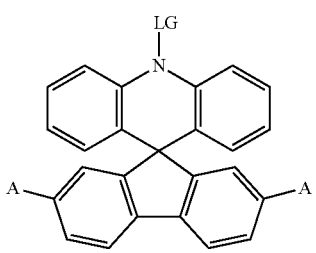

Especially preferred TADF compounds are those of the formula (27).

Formula (27)

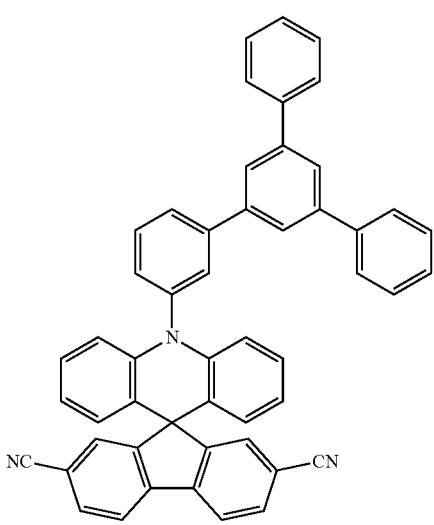

Very particularly preferred TADF compounds are also those of the formulae (28) and (29).

Formula (28)

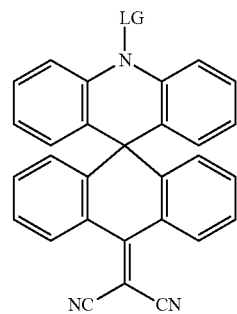

Formula (29)

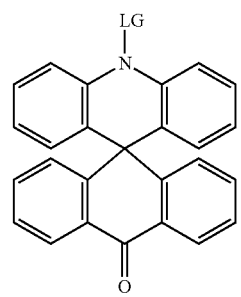

The compounds of the formulae (2) to (29) may be substituted by one or more $R^1$ radicals which may be the same or different at each instance.

The following overview contains an illustrative overview of inventive TADF compounds.

Formula (E-1)

Formula (E-2)
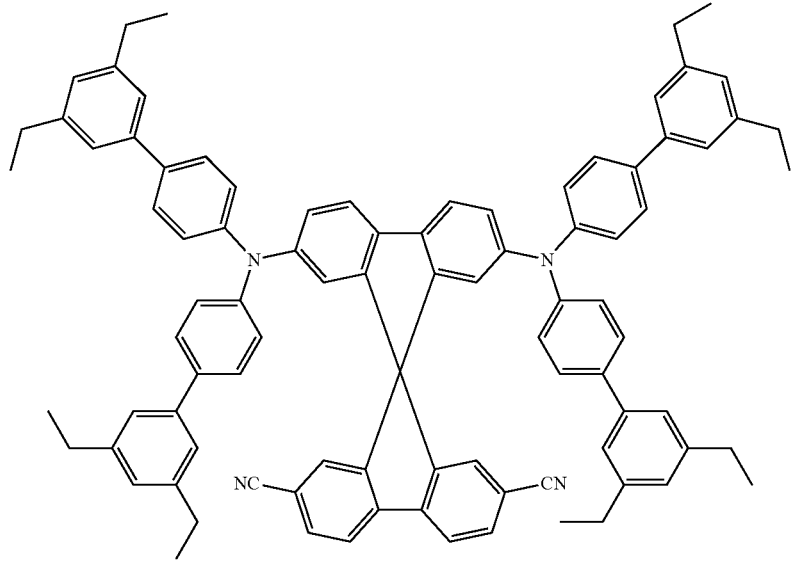
Formula (E-3)
Formula (E-4)
Formula (E-5)
Formula (E-6)
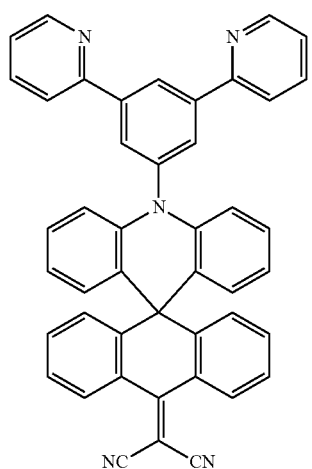
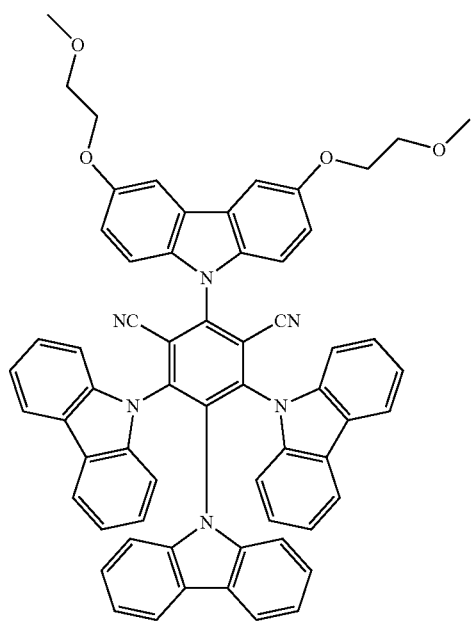

-continued
Formula (E-7)
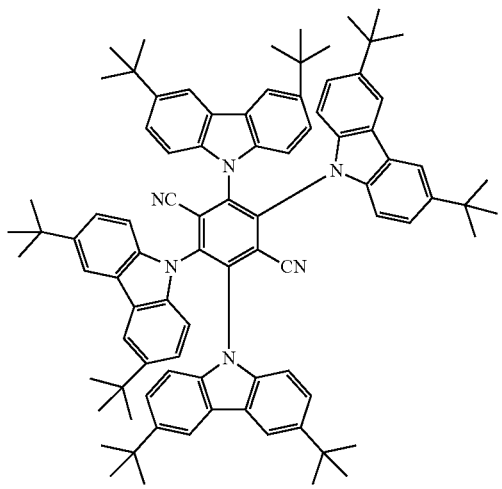
Formula (E-8)
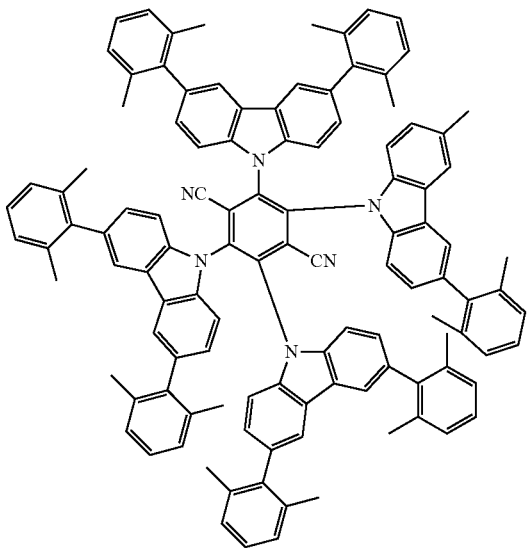
Formula (E-9)
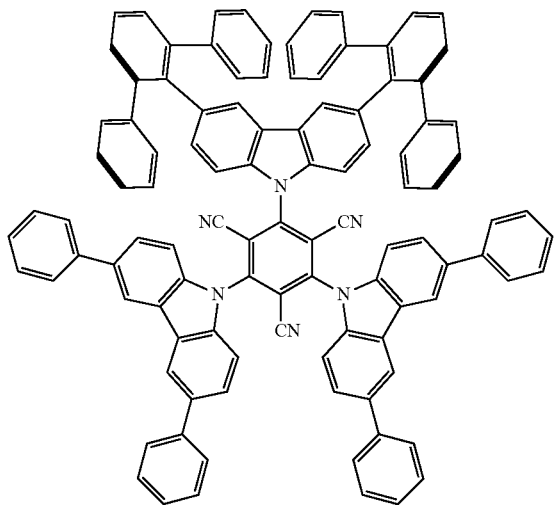
Formula (E-10)
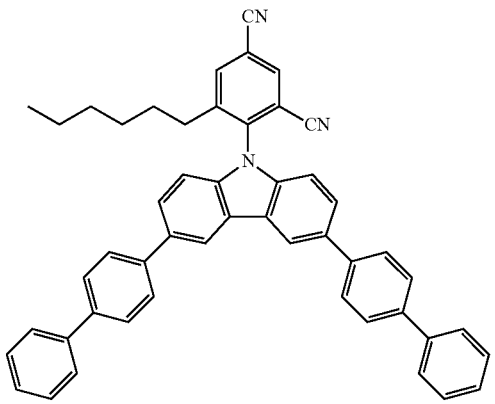
Formula (E-11)
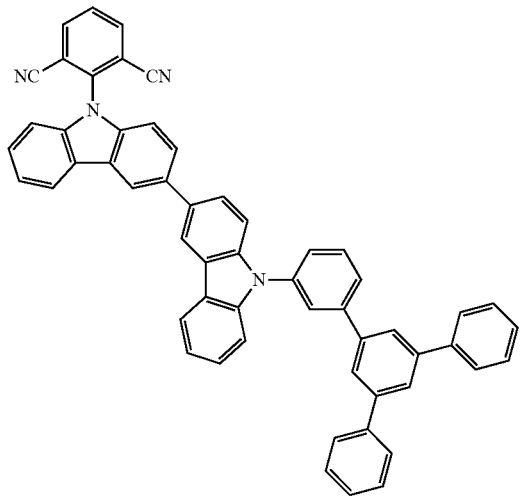
Formula (E-12)
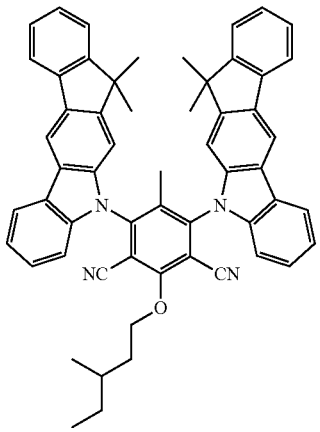

-continued
Formula (E-13)
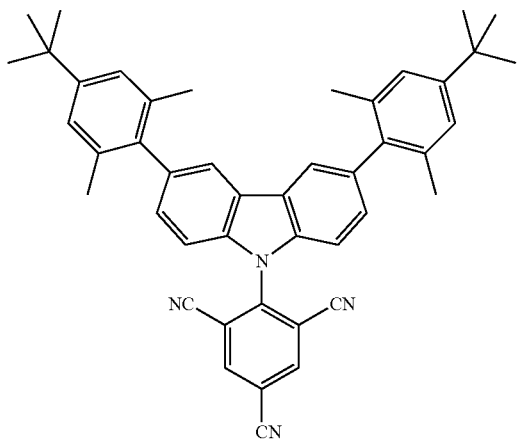
Formula (E-14)
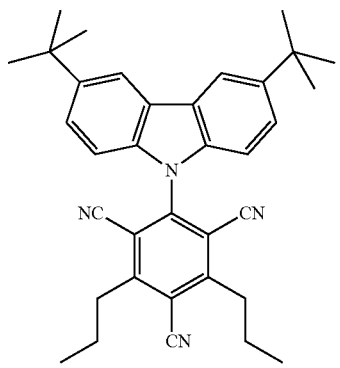
Formula (E-15)
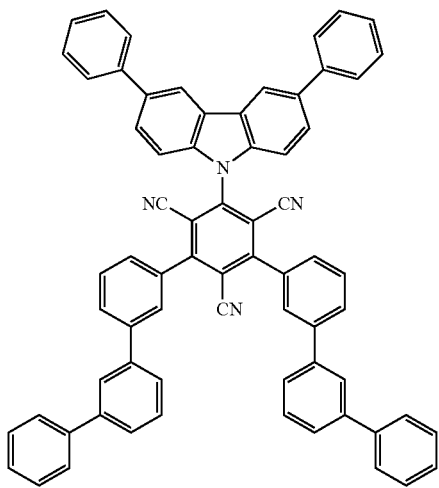
Formula (E-16)
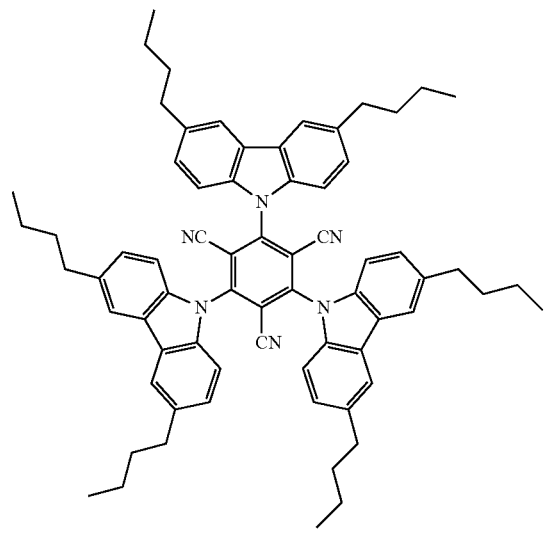
Formula (E-17)
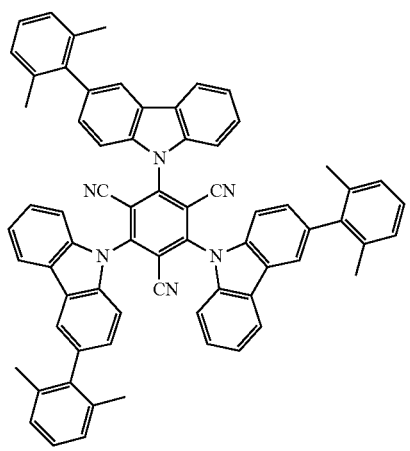
Formula (E-18)
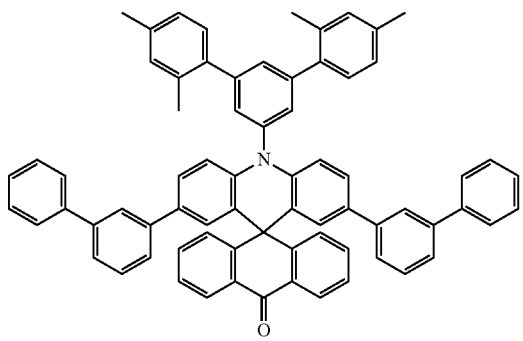

Formula (E-19)
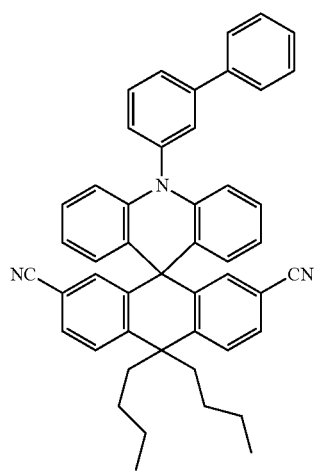
Formula (E-20)
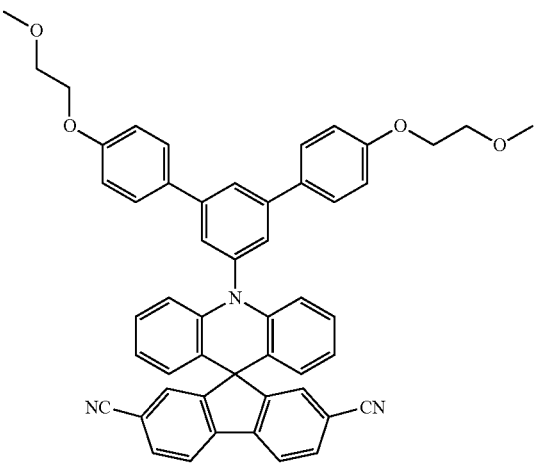
Formula (E-21)
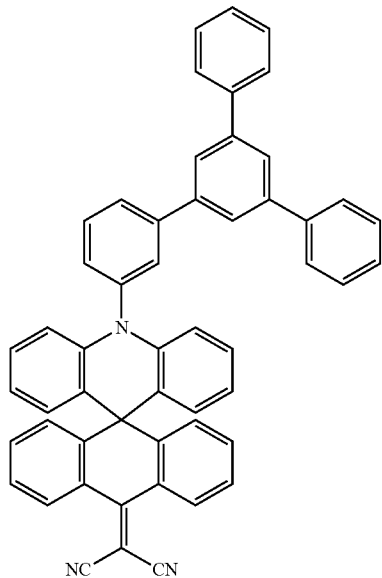
Formula (E-22)
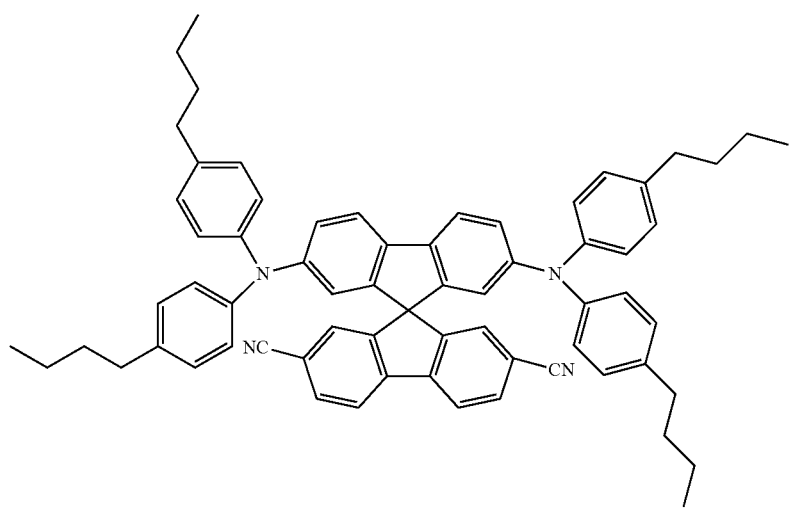

-continued
Formula (E-23)
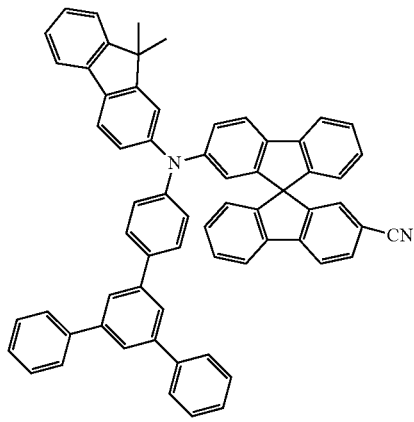
Formula (E-24)
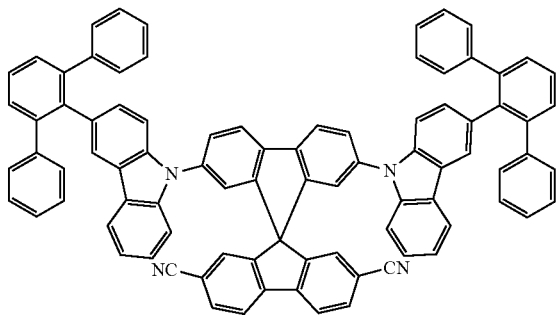
Formula (E-25)
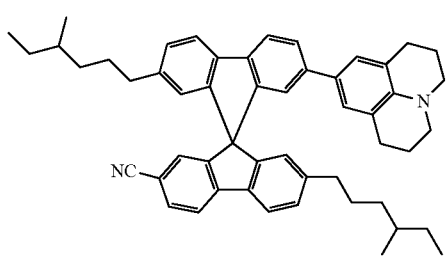
Formula (E-26)
Formula (E-27)
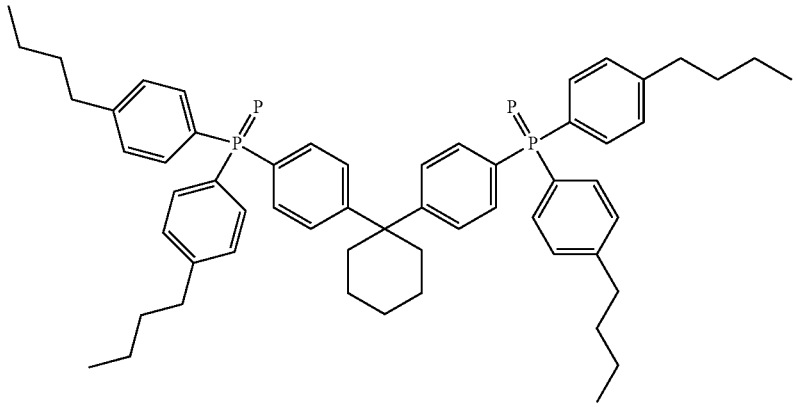
Formula (E-28)
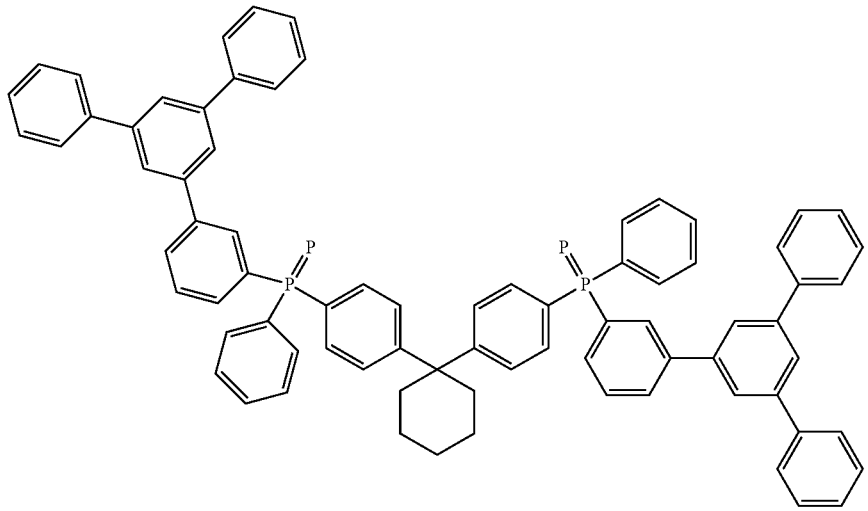

Formula (E-29)
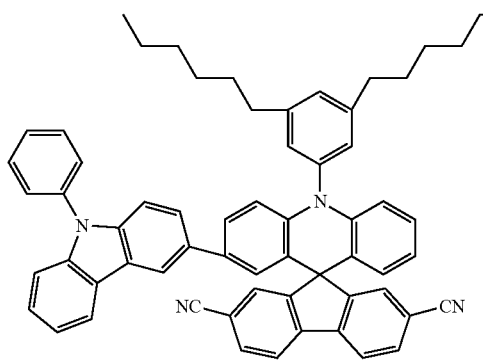
Formula (E-30)
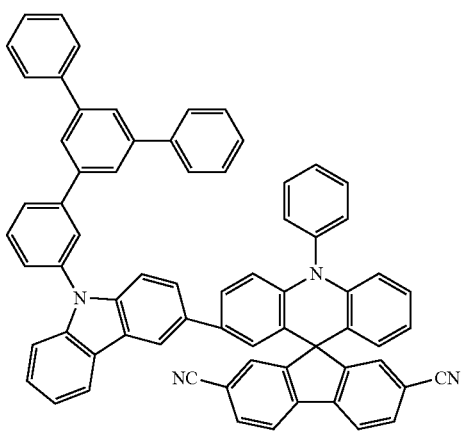
Formula (E-31)
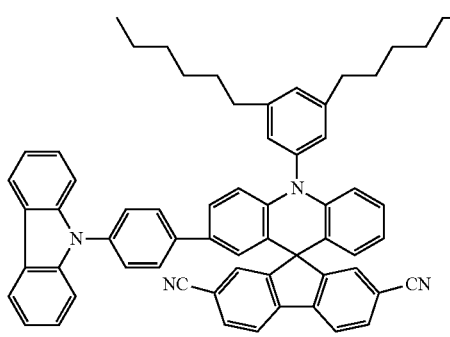
Formula (E-32)
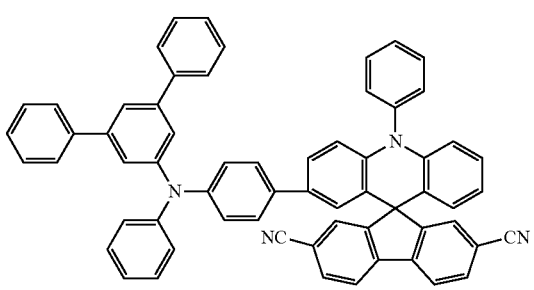
Formula (E-33)
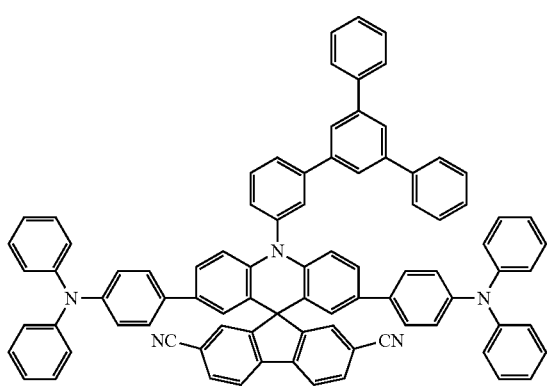
Formula (E-34)
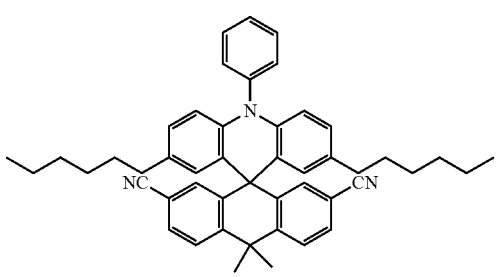

-continued
Formula (E-35)
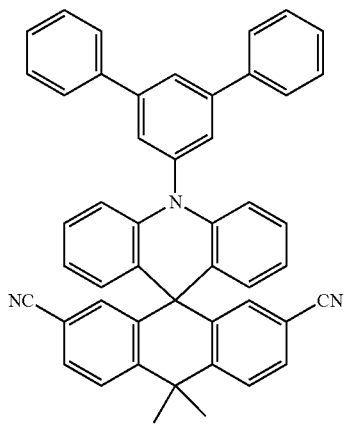
Formula (E-36)
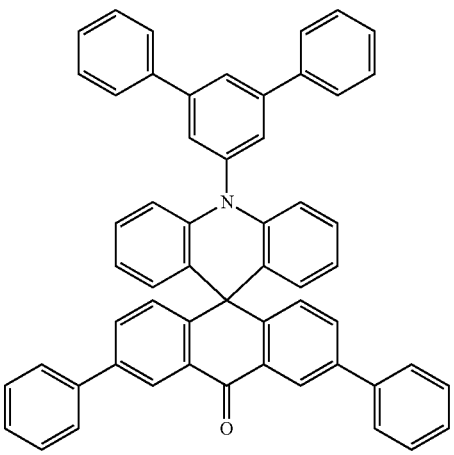
Formula (E-37)
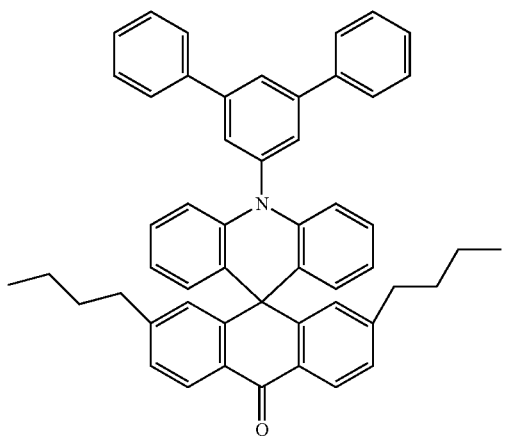
Formula (E-38)
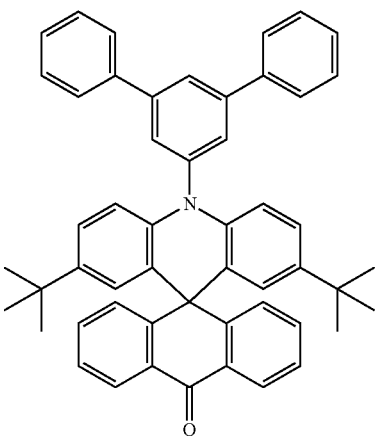
Formula (E-39)
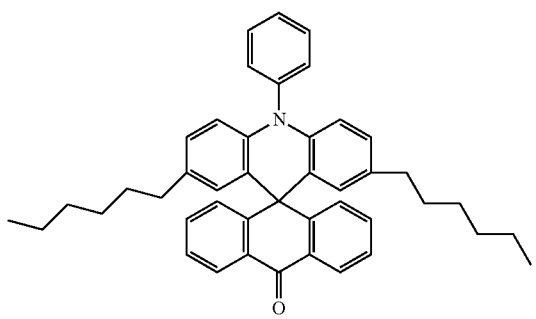
Formula (E-40)
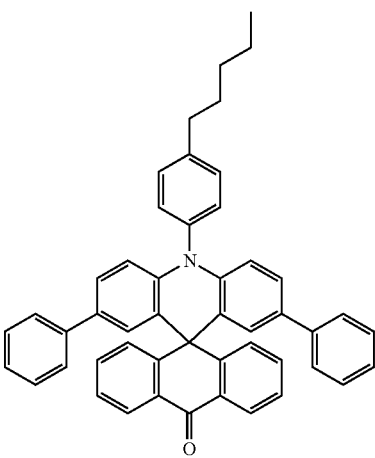

-continued
Formula (E-41)
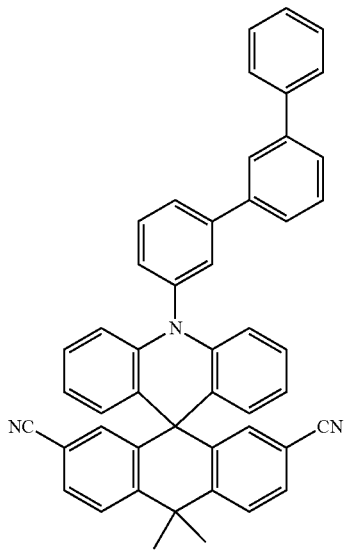
Formula (E-42)
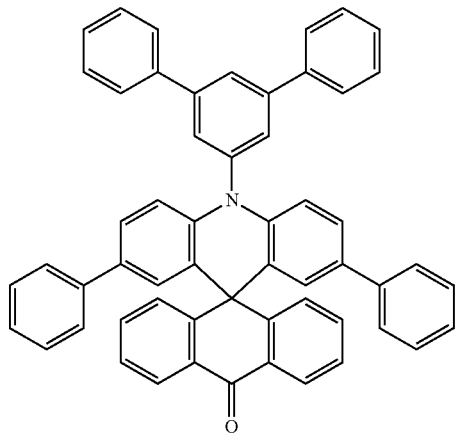
Formula (E-43)
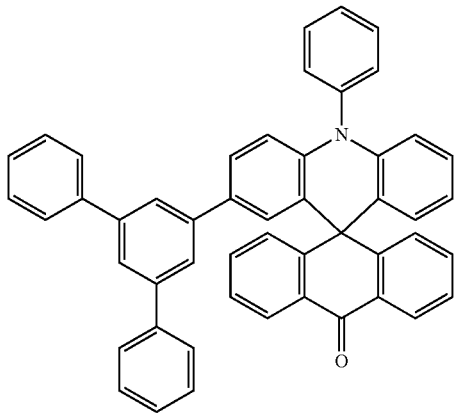
Formula (E-44)
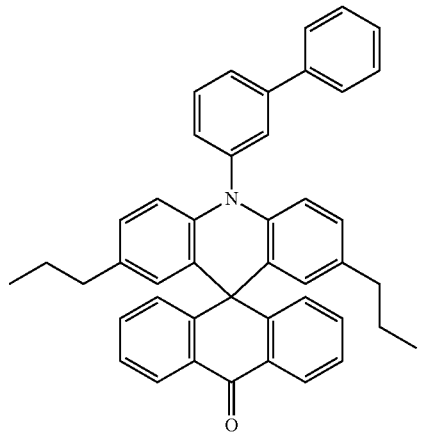
Formula (E-45)
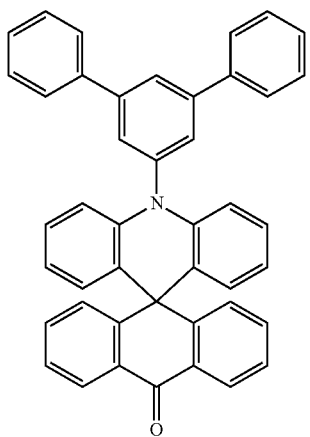
Formula (E-46)
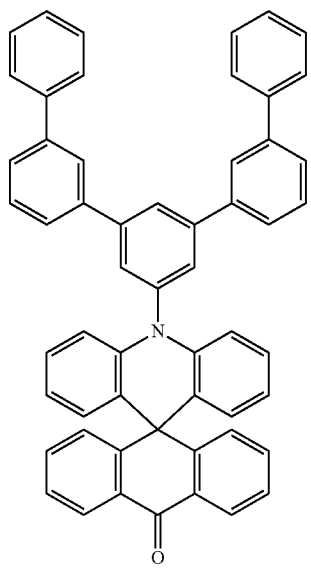

-continued
Formula (E-47)
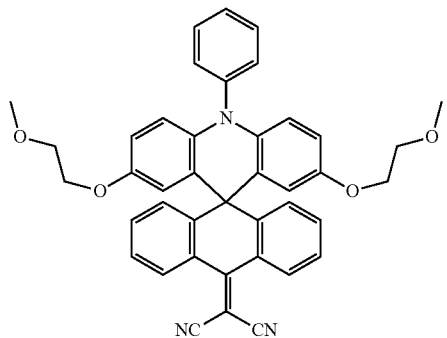
Formula (E-48)
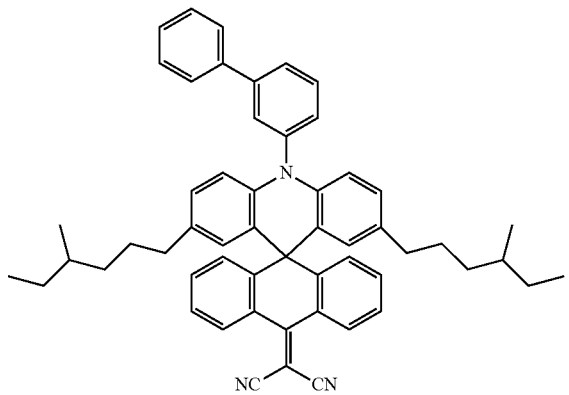
Formula (E-49)
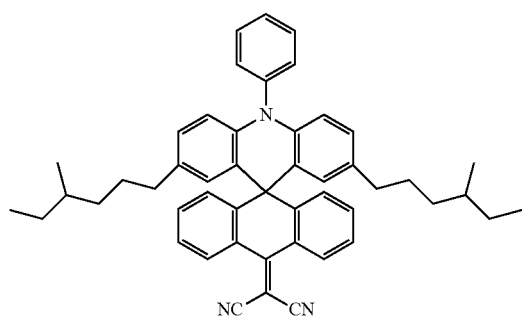
Formula (E-50)
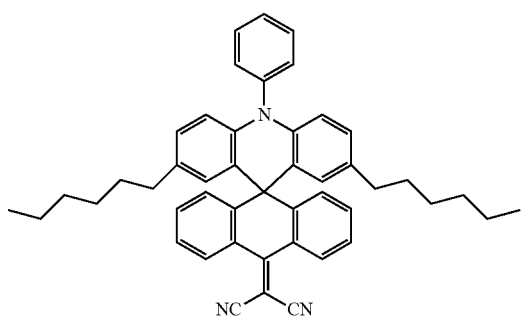
Formula (E-51)
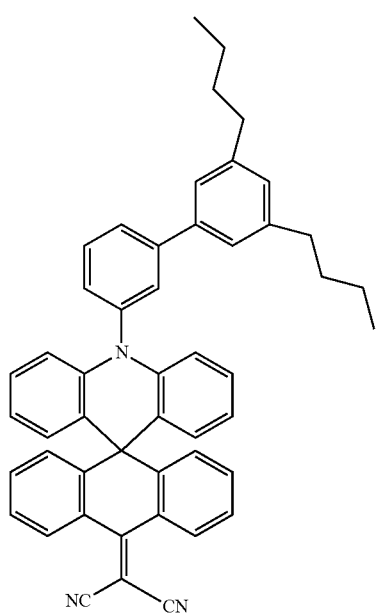
Formula (E-52)
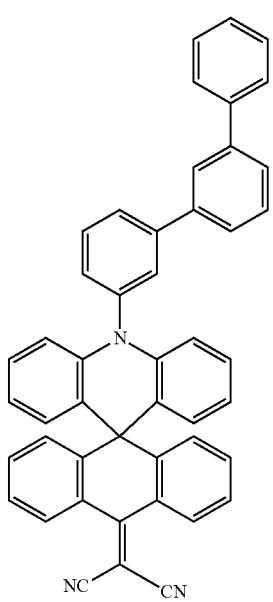

Formula (E-53)
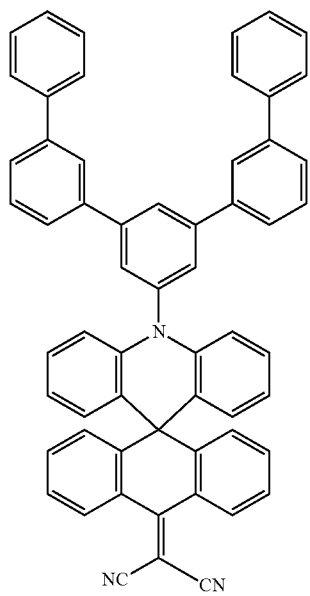
Formula (E-54)
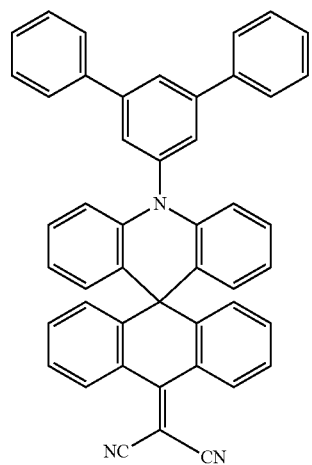
Formula (E-55)
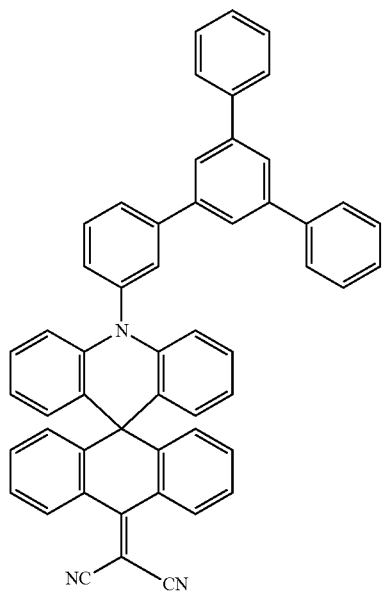
Formula (E-56)
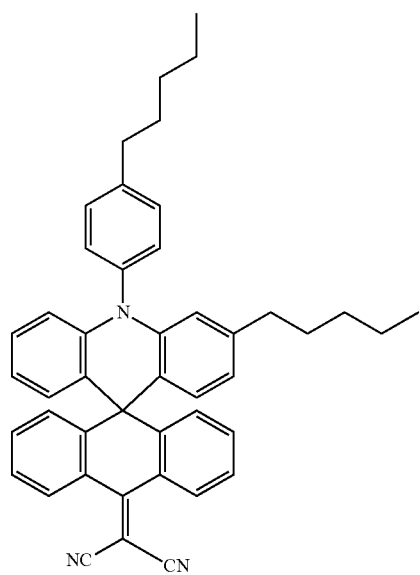

-continued
Formula (E-57)
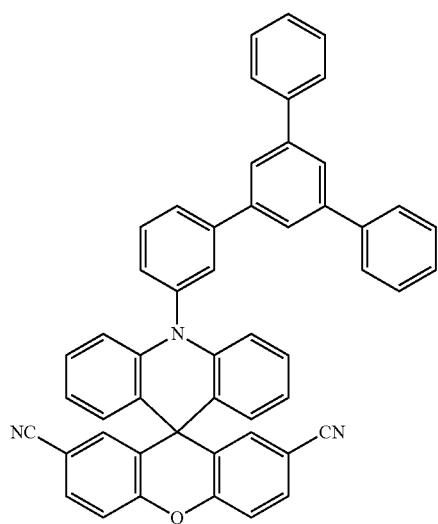
Formula (E-58)
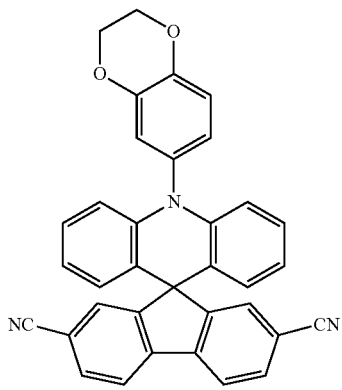
Formula (E-59)
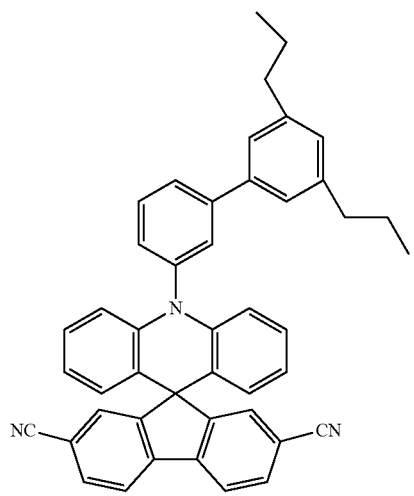
Formula (E-60)
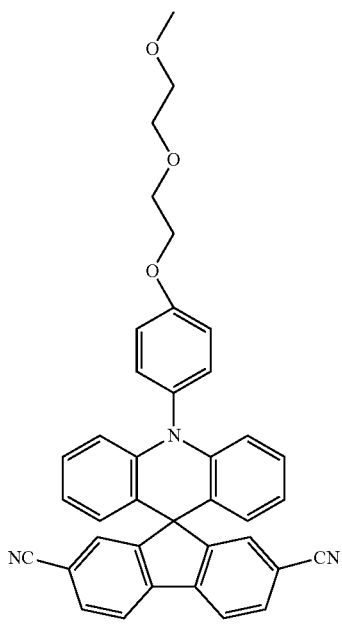
Formula (E-61)
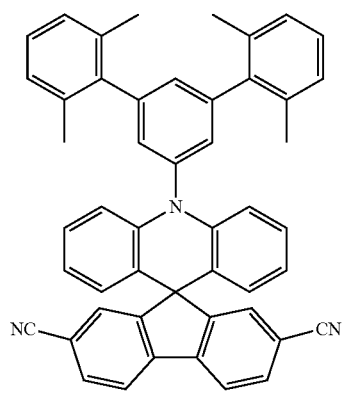
Formula (E-62)
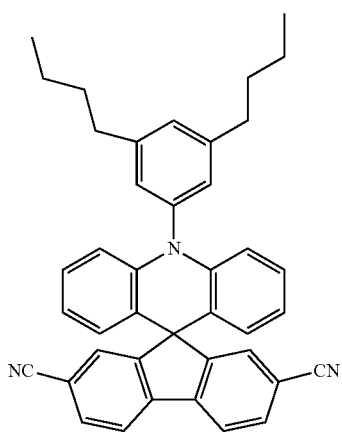

-continued
Formula (E-63)
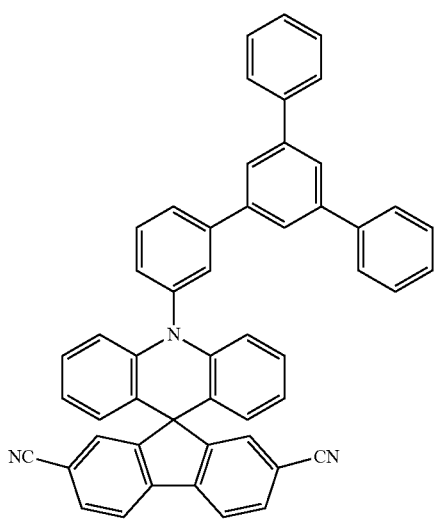
Formula (E-64)
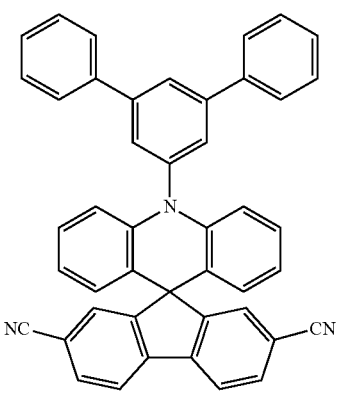
Formula (E-65)
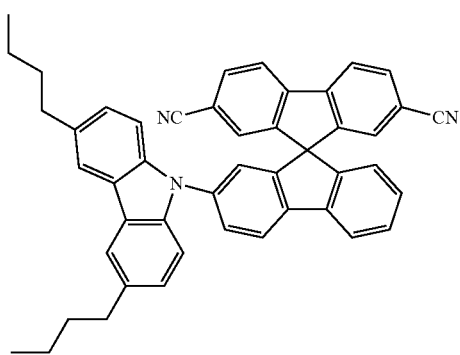
Formula (E-66)
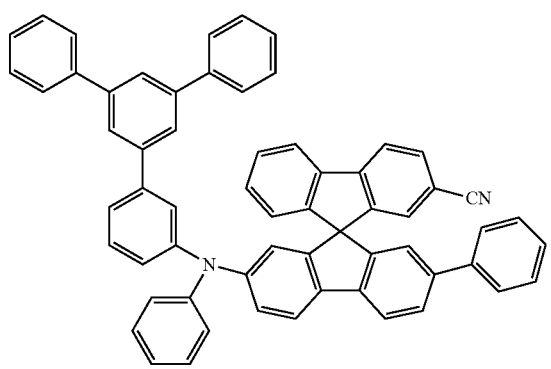
Formula (E-67)
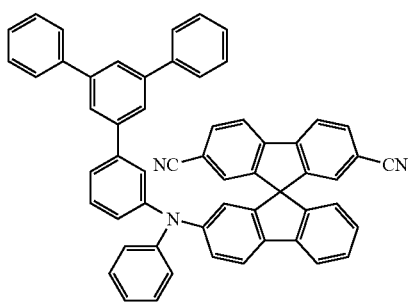
Formula (E-68)
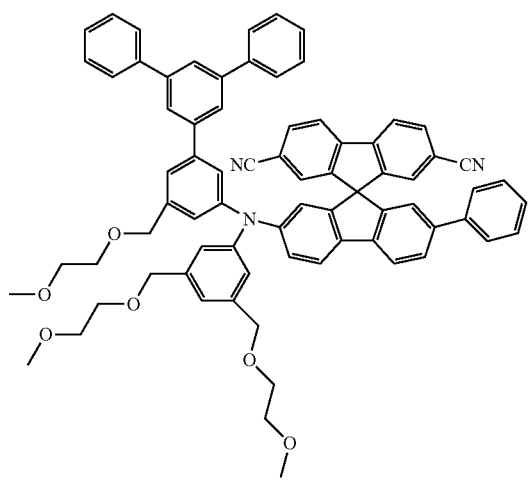

Formula (E-69)
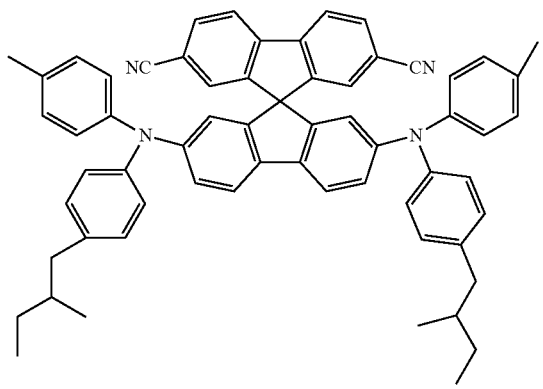
Formula (E-70)
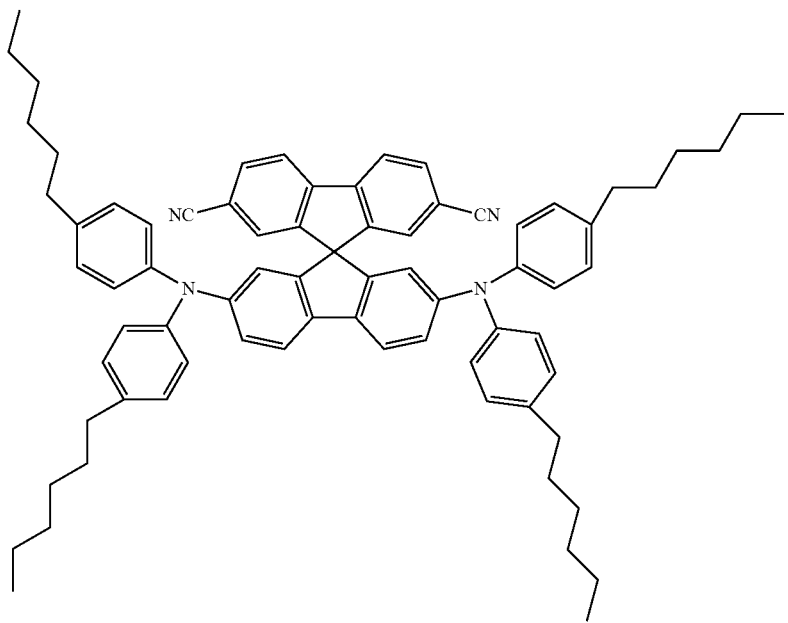
Formula (E-71)
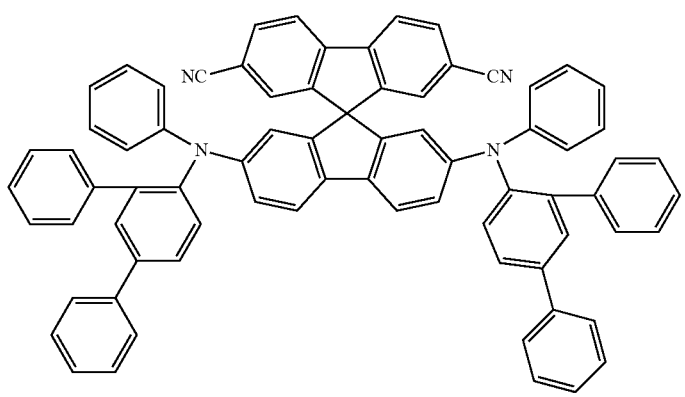

-continued
Formula (E-72)
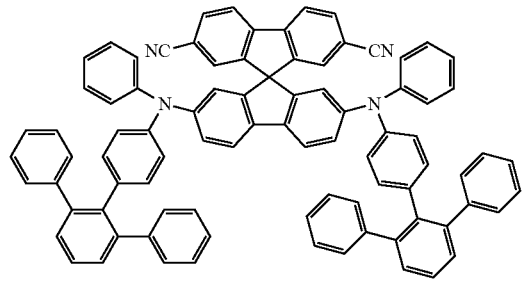
Formula (E-73)
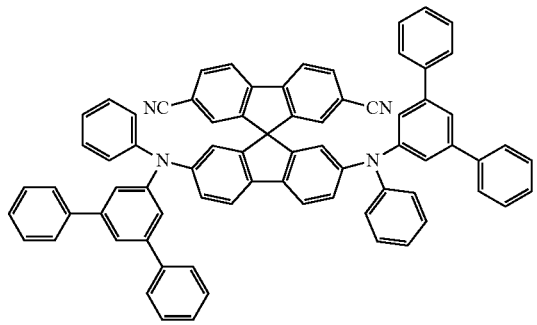
Formula (E-74)
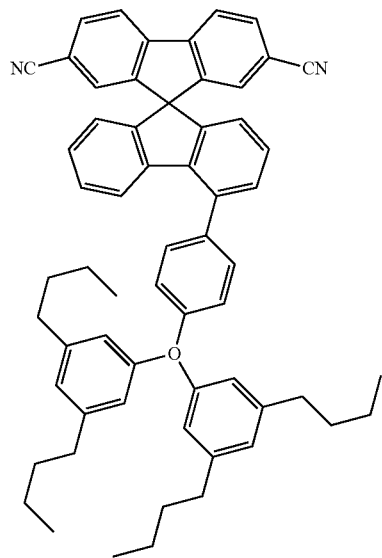
Formula (E-75)
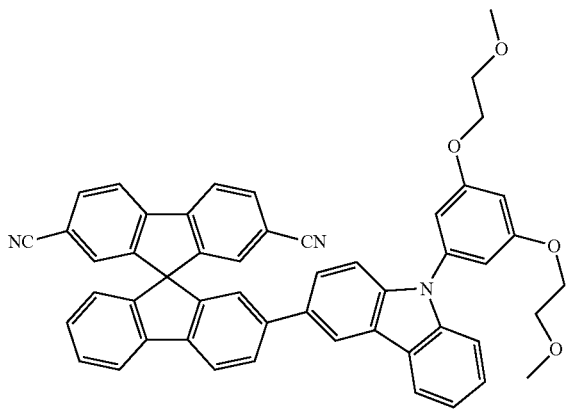
Formula (E-76)
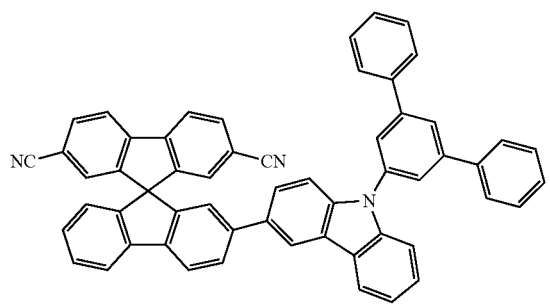
Formula (E-77)
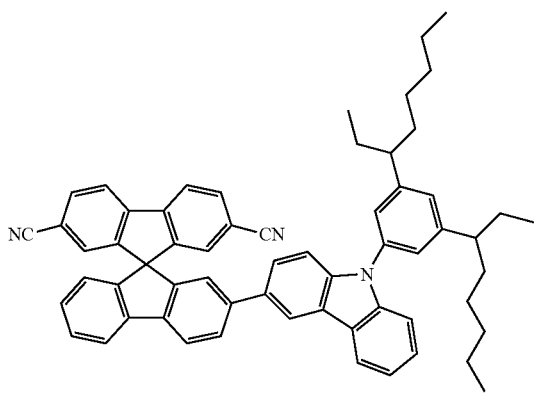

-continued
Formula (E-78)
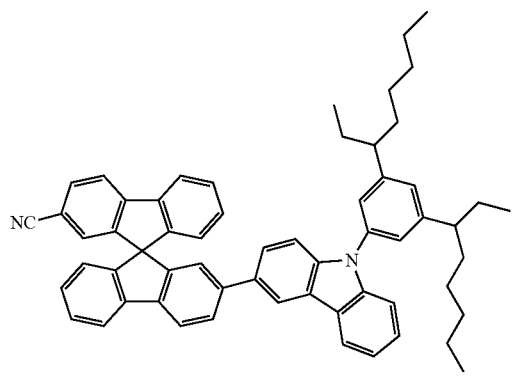
Formula (E-79)
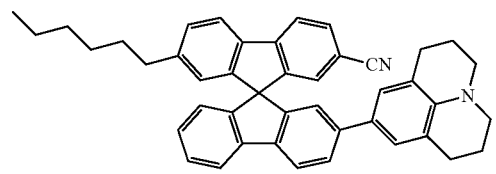
Formula (E-80)
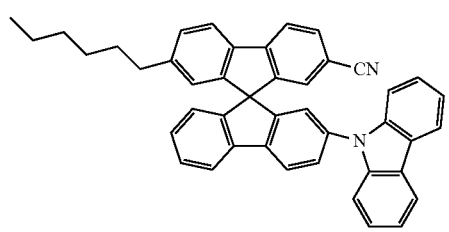
Formula (E-81)
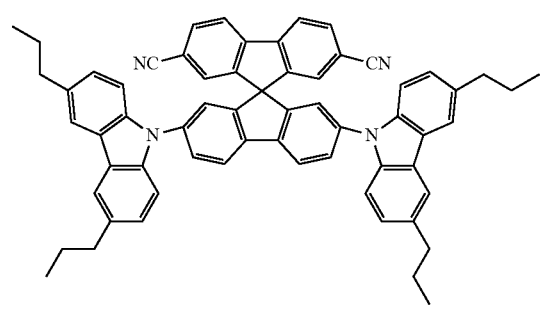
Formula (E-82)
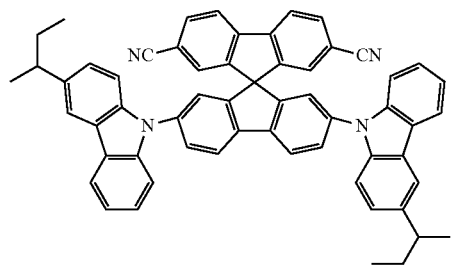
Formula (E-83)
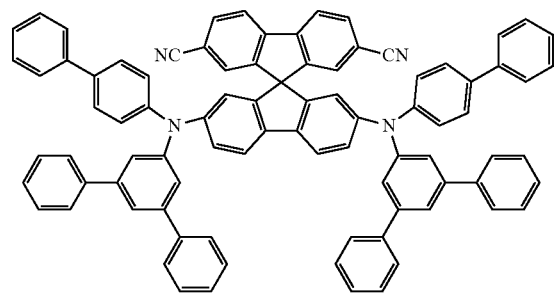
Formula (E-84)
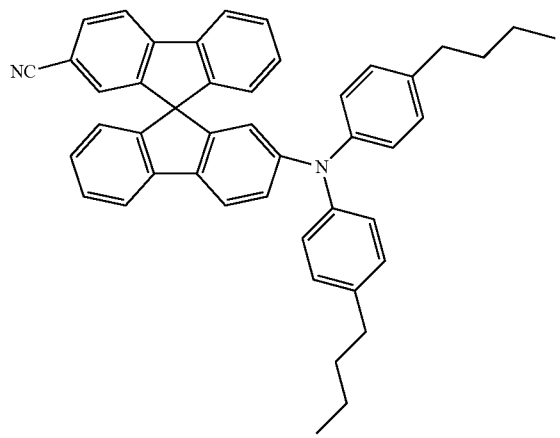
Formula (E-85)
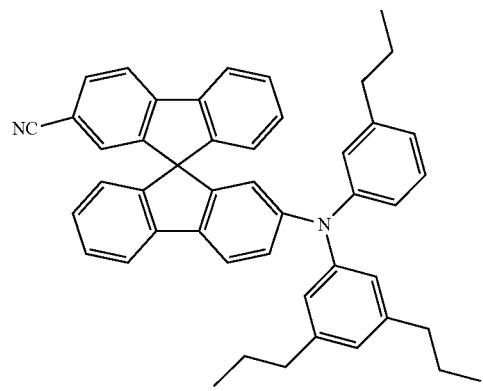

-continued
Formula (E-86)
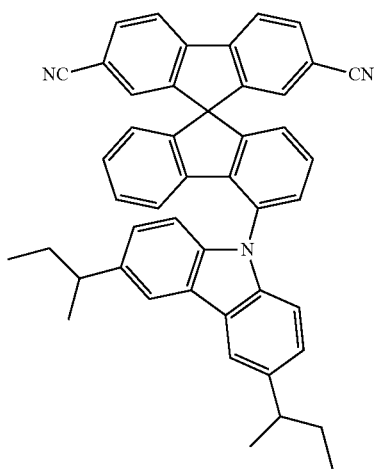
Formula (E-87)
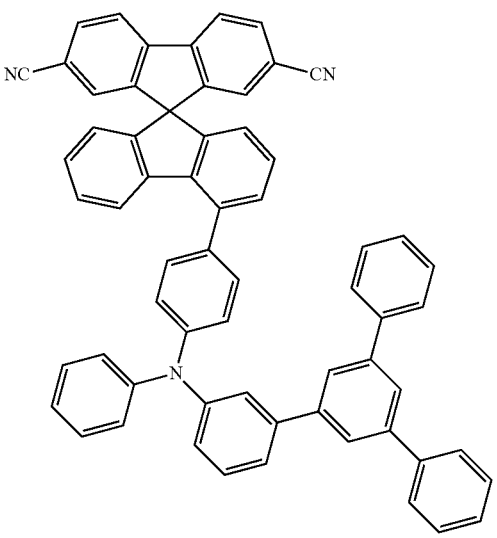
Formula (E-88)
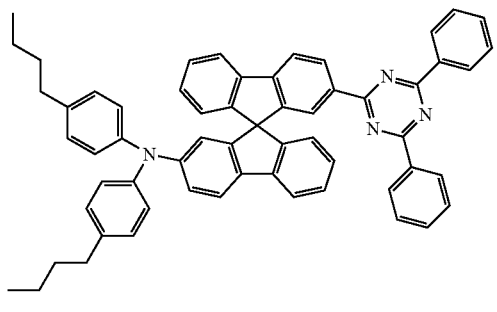
Formula (E-89)
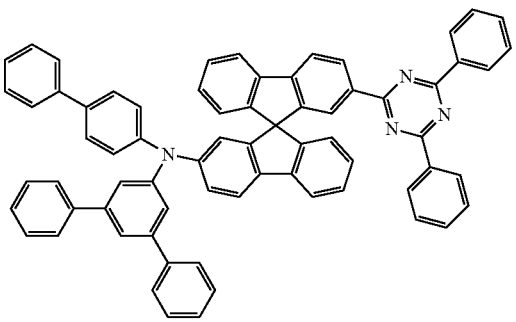
Formula (E-90)
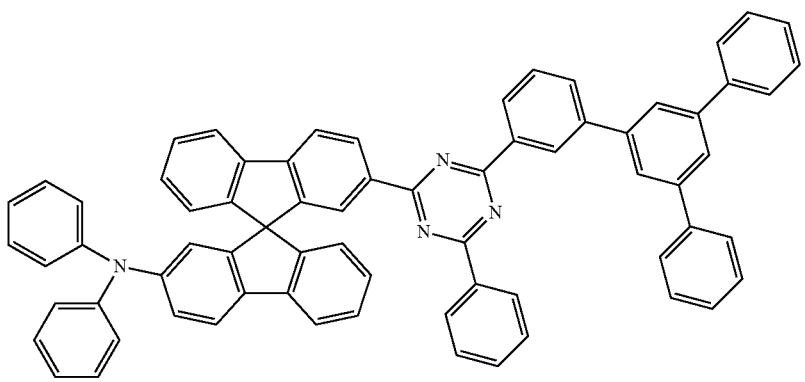

-continued
Formula (E-91)
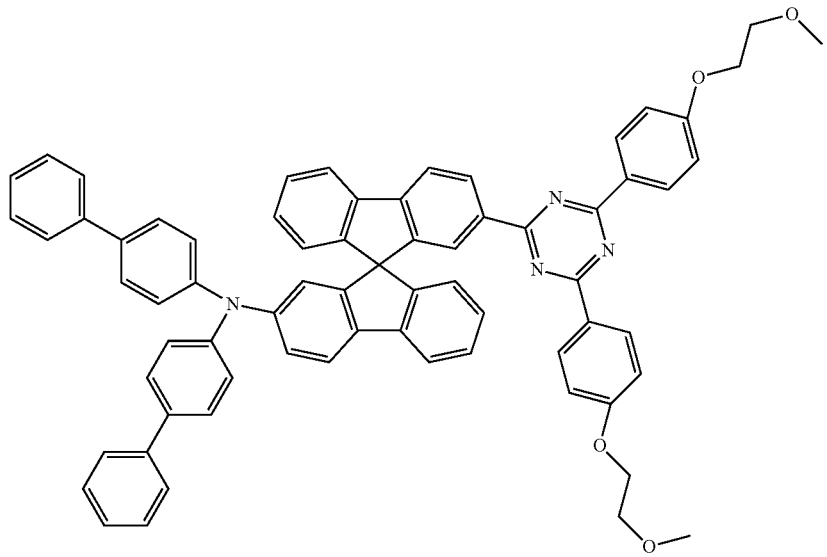
Formula (E-92)                        Formula (E-93)
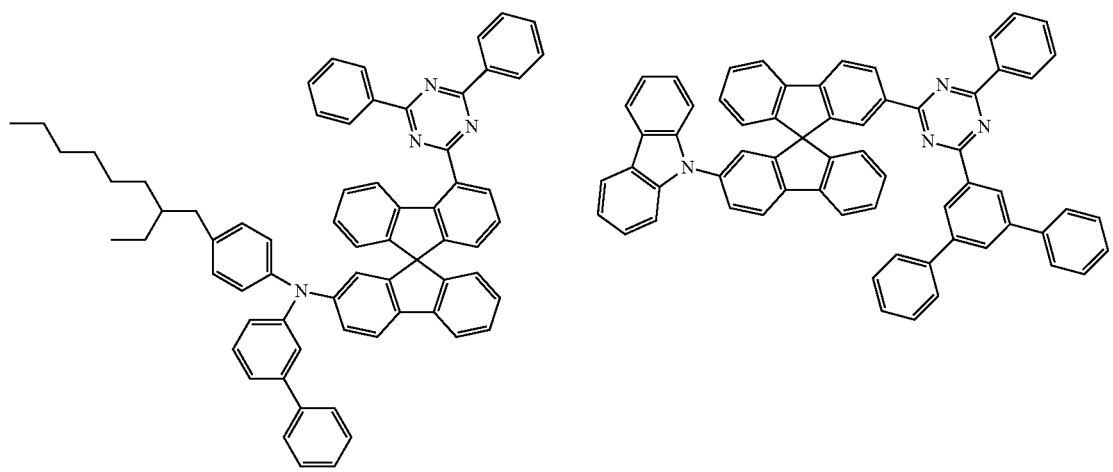
Formula (E-94)
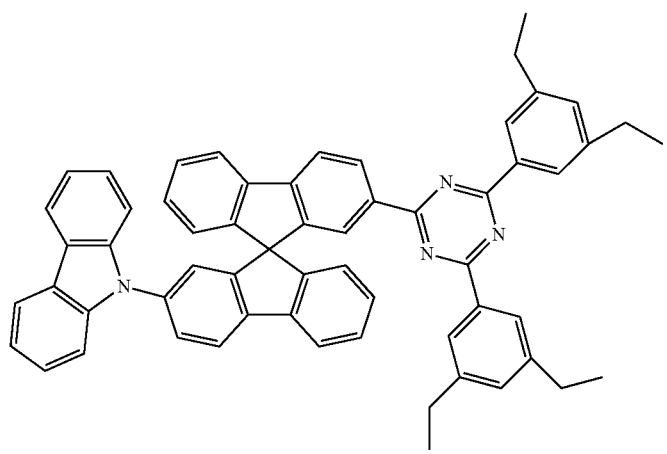

The inventive compounds can be prepared by methods well known to those skilled in the art. The examples disclose various methods.

The inventive organic TADF compounds or compositions comprising the inventive organic TADF compounds may be used in electronic devices, especially in organic electroluminescent devices such as the organic light-emitting diodes (OLEDs) and the organic light-emitting electrochemical cells (OLECs).

The present invention therefore also relates to a composition comprising at least one inventive TADF compound and at least one further organic functional material and/or an inorganic nanoparticle.

The further organic functional material is preferably selected from the group of the electron-conducting materials (ETM), electron-injecting materials (EIM), electron-blocking materials (EBM), hole-conducting materials (HTM), hole-injecting materials (HIM), hole-blocking materials (HBM), fluorescent emitters, phosphorescent emitters and matrix materials, particular preference being given to matrix materials.

The person skilled in the art is well aware of these organic functional materials and will be able to select the materials suitable in each case for the composition without difficulty from a multitude of familiar materials and with reference to standard considerations.

Fluorescent emitters (also called fluorescent dopants) in the context of the present invention are compounds where light is emitted through a spin-allowed transition, preferably a transition from an excited singlet state.

The term "phosphorescent emitters" (also called phosphorescent dopants) typically encompasses compounds where light is emitted through a spin-forbidden transition, for example a transition from a triplet state or a state having a higher spin quantum number, for example a quintet state, the phosphorescent emitters preferably being compounds which emit light from an excited triplet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, are compounds containing copper, molybdenum, tungsten, rhenium, ruthenium, osmium, rhodium, iridium, palladium, platinum, silver, gold or europium, especially compounds containing iridium, platinum or copper.

The TADF compound is preferably used as luminescent compound in the emission layer of an electroluminescent device.

A luminescent compound in the context of the present invention is a compound capable of emitting light at room temperature under optical excitation in an environment as exists in the organic electroluminescent device. This compound preferably has a luminescence quantum efficiency of at least 40%, more preferably of at least 50%, even more preferably of at least 60% and especially preferably of at least 70%. The luminescence quantum efficiency is determined in a mixed layer with the matrix material like that which is to be used in the organic electroluminescent device. The way in which the determination of the luminescence quantum yield is conducted in the context of the present invention is described in a general and detailed manner in the examples section.

The organic TADF compound is preferably present in the emitting layer of an organic electroluminescent device. The inventive TADF compounds may be used either as emitters or as matrix, it being preferable when they are used as emitters. When they are used as emitters in an emission layer, they are preferably present in a matrix. The matrix may consist here of just one material or of a plurality of materials (mixed matrix). The matrix material makes no significant contribution, if any, to the emission of the mixture.

In order to avoid exciplex formation in the emitting layer, it is preferable when the following is true of LUMO(TADF), i.e. the LUMO of the TADF compound, and the HOMO (matrix):

LUMO(TADF)−HOMO(matrix)>$S_1$(TADF)−0.4 eV;

very preferably:

LUMO(TADF)−HOMO(matrix)>$S_1$(TADF)−0.3 eV;

and especially preferably:

LUMO(TADF)−HOMO(matrix)>$S_1$(TADF)−0.2 eV.

$S_1$(TADF) here is the first excited singlet state $S_1$ of the TADF compound.

In order that the TADF compound is the emitting compound in the mixture of the emitting layer, it is preferable that the lowest triplet energy of the matrix is not more than 0.1 eV lower than the triplet energy of the molecule which exhibits TADF. Especially preferably, $T_1$(matrix)≥$T_1$(TADF). More preferably: $T_1$ (matrix)−$T_1$ (TADF) 0.1 eV, most preferably $T_1$ (matrix)−$T_1$ (TADF)≥0.2 eV. $T_1$ (matrix) here is the lowest triplet energy of the matrix compound and $T_1$ (TADF) is the lowest triplet energy of the compound which exhibits TADF. The triplet energy of the matrix, according to the method disclosed in a general and detailed manner in the examples section, is determined by quantum-chemical calculation.

Examples of suitable matrix compounds are lactams, for example according to WO 2011/116865A1, WO 2013/064206A1, WO 2014/056567A1, WO 2014/094964A1, ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, or bridged carbazole derivatives, for example according to US 2009/0136779, WO 2010/050778, WO 2011/042107 or WO 2011/088877.

The inventive TADF compounds and the inventive compositions are of very good suitability for production of electronic devices, especially organic electroluminescent devices, easily and inexpensively from solution. Formulations are required for production from solution. The electronic devices thus produced have very good performance data. In addition, it is found that the electronic devices thus produced have lower failure rates in the production of the devices. The formulations are thus suitable for inexpensive and reliable mass production of electronic devices for commercial use.

Therefore, the present invention also relates to a formulation comprising at least one inventive TADF compound or at least one inventive composition and at least one solvent.

"Formulation" is understood in the present case to mean a composition which, as well as the at least one organic TADF molecule and the possible further organic functional materials, also contains an organic solvent or organic solvent mixture. The solvent or solvent mixture is preferably present in excess.

"Solvent mixture" is understood in the present case to mean a mixture of at least two different solvents.

It is further preferable that the formulation is in liquid form. The formulation may be a true solution or an emulsion, miniemulsion, dispersion or suspension, it being very preferable when the formulation is a true solution.

The formulation is used for production of a layer of organic electronic devices, especially the emission layer of organic electroluminescent devices. During the production of the layer, the solvent or solvent mixture is removed, such that the TADF compound(s) and the potential further organic functional materials are present in excess in the layer with respect to the remaining solvent or solvent mixture. Preferably, the solvent or solvent mixture is present only in traces if at all in the layer of the organic electronic device. It is very preferable when the solvent or solvent mixture has been completely removed and is therefore no longer detectable in the layer applied.

It is preferable when the solvent or solvents (in the case of a solvent mixture) used has/have a surface tension of at least 28 mN/m, preferably at least 30 mN/m, very preferably at least 32 mN/m and even more preferably at least 35 mN/m.

It is further preferable when the boiling or sublimation temperature of the solvent(s) is less than 300° C. and preferably less than 260° C.

It is very preferable when the viscosity of the solvent or of the different solvents in a solvent mixture is greater than 3 mPa*s and preferably greater than 5 mPa*s.

It is further preferable when the molecular weight of the solvent(s) is less than or equal to 1000 g/mol, preferably less than or equal to 700 g/mol, very preferably less than or equal to 500 g/mol and especially preferably less than or equal to 300 g/mol.

As already explained, the solvent or the solvents in a solvent mixture is/are present in excess in the formulation compared to the TADF compound.

The formulation of the present invention may preferably contain 0.01% to 20% by weight, very preferably 0.05% to 10% by weight, more preferably 0.1% to 5% by weight and especially preferably 0.5% to 5% by weight of low molecular weight organic semiconductor materials, low molecular weight organic semiconductor materials being understood to mean the inventive TADF compounds and the further organic functional materials already mentioned above, the molecular weight of which is not more than 4000 g/mol, preferably not more than 3000 g/mol, very preferably not more than 2000 g/mol, even more preferably not more than 1500 g/mol and especially preferably not more than 1000 g/mol.

The person skilled in the art can select from a multitude of solvents and solvent mixtures in order to provide the inventive formulations.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The formulation of the present invention contains one or more organic solvents, preferably at least one aromatic solvent. The solvents are preferably selected from the group consisting of aromatic hydrocarbons such as toluene, o-, m- or p-xylene, phenoxytoluenes, trimethylbenzenes (e.g. 1,2, 3-, 1,2,4- and 1,3,5-trimethylbenzenes), tetralin, other mono-, di-, tri- and tetraalkylbenzenes (e.g. diethylbenzenes, methylcumene, tetramethylbenzenes, etc.), aromatic ethers (e.g. anisole, alkylanisoles, e.g. 2, 3 and 4 isomers of methylanisole, 2,3, 2,4, 2,5, 2,6, 3,4 and 3,5 isomers of dimethylanisole), naphthalene derivatives, alkylnaphthalene derivatives (e.g. 1- and 2-methylnaphthalene), di- and tetrahydronaphthalene derivatives. Likewise preferred are aromatic esters (e.g. alkyl benzoates), aromatic ketones (e.g. acetophenone, propiophenone), alkyl ketones (e.g. cyclohexanone), heteroaromatic solvents (e.g. thiophene, mono-, di- and trialkylthiophenes, 2-alkylthiazoles, benzothiazoles, etc., pyridines), haloarylenes and aniline derivatives. These solvents may contain halogen atoms.

Particular preference is given to: 3-fluorotrifluoromethylbenzene, trifluoromethylbenzene, dioxane, trifluoromethoxybenzene, 4-fluorobenzotrifluoride, 3-fluoropyridine, toluene, 2-fluorotoluene, 2-fluorobenzotrifluoride, 3-fluorotoluene, pyridine, 4-fluorotoluene, 2,5-difluorotoluene, 1-chloro-2,4-difluorobenzene, 2-fluoropyridine, 3-chlorofluorobenzene, 1-chloro-2,5-difluorobenzene, 4-chlorofluorobenzene, chlorobenzene, 2-chlorofluorobenzene, p-xylene, m-xylene, o-xylene, 2,6-lutidine, 2-fluoro-m-xylene, 3-fluoro-o-xylene, 2-chlorobenzotrifluoride, dimethylformamide, 2-chloro-6-fluorotoluene, 2-fluoroanisole, anisole, 2,3-dimethylpyrazine, bromobenzene, 4-fluoroanisole, 3-fluoroanisole, 3-trifluoromethylanisole, 2-methylanisole, phenetole, benzodioxole, 4-methylanisole, 3-methylanisole, 4-fluoro-3-methylanisole, 1,2-dichlorobenzene, 2-fluorobenzonitrile, 4-fluoroveratrole, 2,6-dimethylanisole, aniline, 3-fluorobenzonitrile, 2,5-dimethylanisole, 3,4-dimethylanisole, 2,4-dimethylanisole, benzonitrile, 3,5-dimethylanisole, N,N-dimethylaniline, 1-fluoro-3,5-dimethoxybenzene, phenyl acetate, N-methylaniline, methyl benzoate, N-methylpyrrolidone, morpholine, 1,2-dihydronaphthalene, 1,2,3,4-tetrahydronaphthalene, o-tolunitrile, veratrole, ethyl benzoate, N,N-diethylaniline, propyl benzoate, 1-methylnaphthalene, butyl benzoate, 2-methylbiphenyl, 2-phenylpyridine or 2,2'-bitolyl.

Particular preference is given to aromatic hydrocarbons, especially toluene, phenoxytoluene, dimethylbenzenes (xylenes), trimethylbenzenes, tetralin and methylnaphthalenes, aromatic ethers, especially anisole, and aromatic esters, especially methyl benzoate.

Especially preferred are aromatic ethers, especially anisole and derivatives thereof, such as alkylanisoles, and aromatic esters, especially methyl benzoate.

These solvents may be used as a mixture of two, three or more.

Preferred organic solvents may have Hansen solubility parameters of $H_d$ in the range from 17.0 to 23.2 MPa$^{0.5}$, $H_p$ in the range from 0.2 to 12.5 MPa$^{0.5}$ and $H_h$ in the range from 0.9 to 14.2 MPa$^{0.5}$. Particularly preferred organic solvents have Hansen solubility parameters of $H_d$ in the range from 18.5 to 21.0 MPa$^{0.5}$, $H_p$ in the range from 2.0 to 6.0 MPa$^{0.5}$ and $H_h$ in the range from 2.0 to 6.0 MPa$^{0.5}$.

TABLE 2

Hansen solubility parameters of useful solvents

| Solvent | $H_d$ [MPa$^{0.5}$] | $H_h$ [MPa$^{0.5}$] | $H_p$ [MPa$^{0.5}$] |
|---|---|---|---|
| 1,2,3,4-Tetrahydro-1-naphthol | 19.6 | 9.2 | 12.8 |
| 1,2,3,4-Tetrahydronaphthalene | 19.1 | 2.3 | 4.0 |
| 1,2,3,4-Tetramethylbenzene | 18.7 | 1.8 | 1.6 |
| 1,2,3,5-Tetramethylbenzene | 18.7 | 1.8 | 1.6 |
| 1,2,3-Trimethylbenzene | 19.0 | 2.9 | 1.6 |
| 1,2,4,5-Tetramethylbenzene | 18.7 | 1.8 | 1.6 |
| 1,2,4-Trichlorobenzene | 20.5 | 6.9 | 2.7 |
| 1,2,4-Trimethylbenzene | 19.0 | 2.9 | 1.6 |
| 1,2-Dihydronaphthalene | 20.1 | 5.5 | 4.9 |
| 1,2-Dimethylnaphthalene | 21.0 | 1.7 | 5.2 |
| 1,3,3-Trimethyl-2-methyleneindole | 17.9 | 1.0 | 3.0 |
| 1,3-Benzodioxole | 19.7 | 7.4 | 7.9 |
| 1,3-Diisopropylbenzene | 17.5 | 0.2 | 1.1 |
| 1,3-Dimethylnaphthalene | 21.0 | 1.7 | 5.2 |
| 1,4-Benzodioxane | 19.5 | 8.7 | 7.2 |
| 1,4-Diisopropylbenzene | 17.5 | 0.6 | 1.6 |
| 1,4-Dimethylnaphthalene | 21.0 | 1.7 | 5.2 |
| 1,5-Dimethyltetralin | 19.3 | 5.5 | 2.6 |
| 1-Benzothiophene | 19.7 | 12.3 | 6.3 |
| 1-Bromonaphthalene | 23.1 | 10.3 | 6.1 |
| 1-Chloromethylnaphthalene | 22.1 | 9.9 | 5.3 |
| 1-Ethylnaphthalene | 20.7 | 7.8 | 4.4 |
| 1-Methoxynaphthalene | 21.4 | 10.5 | 7.5 |
| 1-Methylnaphthalene | 21.7 | 8.4 | 4.5 |
| 1-Methylindane | 19.4 | 5.7 | 2.5 |
| 1-Methylindole | 19.2 | 8.1 | 10.2 |
| 2,3,3-Trimethoxyindolenine | 19.6 | 6.8 | 4.2 |
| 2,3-Benzofuran | 21.3 | 5.5 | 5.6 |
| 2,3-Dihydrobenzofuran | 19.9 | 9.5 | 6.6 |
| 2,3-Dimethylanisole | 18.9 | 4.6 | 4.5 |
| 2,4-Dimethylanisole | 18.9 | 4.6 | 4.5 |
| 2,5-Dimethylanisole | 18.9 | 4.6 | 4.5 |
| 2,6-Diisopropylnaphthalene | 18.3 | 3.5 | 2.2 |
| 2,6-Dimethylanisole | 18.9 | 4.6 | 4.5 |
| 2,6-Dimethylnaphthalene | 20.1 | 5.0 | 3.0 |
| 2-Bromo-3-(bromomethyl)thiophene | 19.3 | 7.3 | 6.6 |
| 2-Bromomethylnaphthalene | 22.0 | 9.4 | 7.2 |
| 2-Bromonaphthalene | 23.1 | 10.3 | 6.1 |
| 2-Ethoxynaphthalene | 20.5 | 10.0 | 7.0 |
| 2-Ethylnaphthalene | 20.7 | 7.8 | 4.4 |
| 2-Isopropylanisole | 17.7 | 4.3 | 5.4 |
| 2-Methylquinoline | 20.0 | 7.8 | 4.0 |
| 2-Methylanisole | 18.3 | 5.1 | 6.2 |
| 2-Methylindole | 17.8 | 9.7 | 4.8 |
| 2-Phenoxyethanol | 18.7 | 8.5 | 13.0 |
| 3,4-Dimethylanisole | 18.9 | 4.6 | 4.5 |
| 3,5-Dimethylanisole | 18.9 | 4.6 | 4.5 |
| 3-Bromoquinoline | 21.4 | 8.7 | 5.1 |
| 3-Isopropylbiphenyl | 19.1 | 1.3 | 1.9 |
| 3-Methylanisole | 18.7 | 5.7 | 5.4 |
| 4-Benzylacetone | 18.3 | 8.8 | 5.0 |
| 4-Isopropylbiphenyl | 19.0 | 2.5 | 1.9 |
| 4-Methoxybenzyl alcohol | 19.0 | 8.5 | 13.3 |
| 4-Methylanisole | 18.6 | 5.9 | 7.2 |
| 4-Phenyl-2-butanone | 18.3 | 8.8 | 5.0 |
| 5,6,7,8-Tetrahydro-1-naphthol | 19.6 | 7.2 | 10.9 |
| 5,6,7,8-Tetrahydro-2-naphthol | 19.6 | 7.2 | 10.9 |
| 5,6,7,8-Tetrahydro-2-naphthylamine | 20.1 | 7.9 | 8.6 |
| 5,6,7,8-Tetrahydro-1-naphthylamine | 20.1 | 7.9 | 8.6 |
| 5-Decanolide | 17.1 | 7.8 | 3.8 |
| 5-Methoxyindane | 19.8 | 9.8 | 4.0 |
| 5-Methoxyindole | 17.4 | 12.3 | 7.8 |
| 5-tert-Butyl-m-xylene | 17.6 | 3.4 | 2.2 |
| 6-Methoxy-1,2,3,4-tetrahydronapthalene | 19.4 | 6.8 | 5.4 |
| 6-Methylquinoline | 21.7 | 8.4 | 4.5 |
| 8-Methylquinoline | 21.7 | 8.4 | 4.5 |
| Acetophenone | 18.8 | 10.8 | 5.5 |
| Anisole | 18.5 | 5.5 | 5.2 |
| α-Pinene | 17.4 | 3.0 | 3.2 |
| Benzonitrile | 19.2 | 11.9 | 4.7 |
| Benzothiazole | 21.3 | 5.5 | 5.6 |
| Benzyl acetate | 18.2 | 7.3 | 6.4 |
| Benzyl alcohol | 19.1 | 6.7 | 14.2 |
| Bromobenzene | 19.8 | 7.6 | 4.3 |
| Butylbenzene | 17.6 | 2.6 | 1.7 |
| Butyl benzoate | 17.7 | 5.9 | 5.2 |
| Cyclohexylbenzene | 18.6 | 1.0 | 1.6 |
| Decahydronaphthalene | 17.5 | 0.4 | 1.0 |
| Diphenyl ether | 19.9 | 2.9 | 3.3 |
| Ethyl phenyl ketone (propiophenone) | 18.3 | 8.9 | 5.3 |
| Ethylbenzene | 18.2 | 2.7 | 2.1 |
| Ethyl benzoate | 18.1 | 6.6 | 5.9 |
| Furfuryl alcohol | 18.1 | 6.7 | 11.9 |
| gamma-Terpinene | 18.0 | 2.5 | 2.8 |
| Hexylbenzene | 17.4 | 2.9 | 1.6 |
| Indane | 19.7 | 7.3 | 5.8 |
| Indene | 20.3 | 4.4 | 5.4 |
| Isoamylbenzene | 17.1 | 3.7 | 1.8 |
| Isobutylbenzene | 17.1 | 2.9 | 1.6 |
| Isopropylbenzene (cumene) | 17.8 | 2.0 | 1.1 |
| m-Cymene | 18.1 | 2.0 | 2.1 |
| Mesitylene | 19.0 | 2.9 | 1.6 |
| Methyl benzoate | 18.5 | 7.9 | 6.4 |
| Methyl phenylacetate | 18.2 | 7.3 | 6.4 |
| m-Xylene | 18.8 | 3.1 | 2.7 |
| n-Butoxybenzene | 17.5 | 4.4 | 4.1 |
| n-Butylbenzene | 17.6 | 2.6 | 1.7 |
| n-Propyl benzoate | 17.8 | 6.6 | 6.3 |
| n-Propylbenzene | 17.8 | 3.4 | 2.8 |
| o-Dichlorobenzene | 19.5 | 8.7 | 3.3 |
| o-Diethylbenzene | 17.7 | 0.7 | 1.9 |
| o-Ethyltoluene | 18.0 | 1.9 | 2.8 |
| o-Xylene | 18.4 | 2.0 | 2.9 |
| Pentylbenzene | 17.4 | 3.0 | 1.8 |
| p-Ethyltoluene | 18.3 | 3.5 | 2.8 |
| Phenetole | 18.1 | 4.6 | 4.6 |
| Phenyl acetate | 18.5 | 7.9 | 6.4 |
| p-Isopropyltoluene (p-cymene) | 18.0 | 2.5 | 2.8 |
| Propiophenone | 18.3 | 8.9 | 5.3 |
| Propyl benzoate | 17.8 | 6.6 | 6.3 |
| p-Xylene | 18.7 | 3.3 | 3.3 |
| sec-Butyl benzene | 17.2 | 2.2 | 1.6 |
| t-Butylbenzene | 17.2 | 1.3 | 2.9 |
| Tetralin | 19.1 | 2.3 | 4.0 |
| Thiophene | 18.8 | 5.2 | 7.4 |

TABLE 2-continued

Hansen solubility parameters of useful solvents

| Solvent | $H_d$ [MPa$^{0.5}$] | $H_h$ [MPa$^{0.5}$] | $H_p$ [MPa$^{0.5}$] |
|---|---|---|---|
| Toluene | 18.6 | 4.0 | 2.2 |
| Veratrole | 18.2 | 6.3 | 7.5 |

$H_d$ relates to the dispersion contribution.
$H_p$ relates to the polar contribution.
$H_h$ relates to the hydrogen bonding contribution.

Preferably, the solvent at the pressure used, very preferably at atmospheric pressure (1013 hPa), has a boiling point or a sublimation temperature of <300° C., more preferably 260° C., especially preferably 220° C. The evaporation can also be accelerated, for example by using heat and/or reduced pressure. The use of solvents having a boiling point of at least 100° C., preferably at least 130° C., can achieve unexpected improvements.

Typically, the organic solvent may have a surface tension of at least 28 mN/m, preferably at least 30 mN/m, more preferably at least 32 mN/m and especially preferably at least 35 mN/m. The surface tension can be measured with an FTA (First Ten Angstroms) 125 contact angle goniometer at 25° C. Details of the method are available from First Ten Angstroms, as published by Roger P. Woodward, Ph.D., "Surface Tension Measurements Using the Drop Shape Method". It is possible with preference to use the pendant drop method to determine the surface tension.

For a rough estimate, it is possible to calculate the surface tension using the Hansen solubility parameters by the formula laid out in Hansen Solubility Parameters: A User's Handbook, Second Edition, C. M. Hansen (2007), Taylor and Francis Group, LLC (HSPiP Handbook).

$$\text{Surface tension} = 0.0146 \times (2.28 \times \delta H_d^2 + H_p^2 + \delta H_h^2) \times \text{MVol}^{0.2}$$

where:
$H_d$ relates to the dispersion contribution,
$H_p$ relates to the polar contribution,
$H_h$ relates to the hydrogen bonding contribution,
MVol relates to the molar volume.

The Hansen solubility parameters can be determined by the program Hansen Solubility Parameters in Practice (HSPiP) (2nd edition) as obtainable from Hanson and Abbot et al.

Preferably, the solvent may have a relative evaporation rate (butyl acetate=100) of at least 0.01, preferably of at least 0.1, more preferably of at least 0.5, especially preferably of at least 5, very especially preferably of at least 10 and particularly preferably of at least 20. The relative evaporation rate can be determined according to DIN 53170: 2009-08. For a rough estimate, it is possible to calculate the relative evaporation rate using the Hansen solubility parameters with the HSPiP program as specified above and below.

The formulation of the present invention preferably contains at least 70% by weight, more preferably at least 80% by weight and especially preferably at least 90% by weight of one or more organic solvents, based on the total mass of the formulation.

In a further preferred embodiment, the formulation of the present invention contains at least one polymer material as an inert binder. This means that the polymer does not have any semiconductor properties or reacts chemically with one of the semiconductor compounds in the composition. The low conductivity properties of the inert polymeric binder can be determined as a low dielectric constant. Preferred binders according to the present invention are materials having a low dielectric constant, i.e. those which have a dielectric constant (E) at 1000 Hz of 3.3 or less. The organic binder preferably has a dielectric constant at 1000 Hz of less than 3.0, more preferably 2.9 or less. Preferably, the organic binder has a dielectric constant at 1000 Hz of greater than 1.7. With particular preference, the dielectric constant of the binder is in the range from 2.0 to 2.9. The expression "react chemically" as used above and below refers to a possible oxidation or other chemical reaction of the nonconductive addition with the organic light-emitting materials and/or charge transport materials under the conditions used for the production, storage, transport and/or use of the formulation and of the OLED device.

Preferably, the polymeric binder has a weight-average molecular weight in the range from 1000 to 50 000 000 g/mol, more preferably 1500 to 10 000 000 g/mol and especially preferably 2000 to 5 000 000 g/mol. With polymers having a weight-average molecular weight of preferably 10 000 g/mol, more preferably 100 000 g/mol, it is possible to achieve surprising effects.

The polymer may especially have a polydispersity index $M_w/M_n$ in the range from 1.0 to 10.0, more preferably in the range from 1.1 to 5.0 and especially preferably in the range from 1.2 to 3.

Typically, the polymeric binder is dispersible or soluble in the solvent of the present composition as described above and below. Preferably, the polymeric binder is soluble in the organic solvent and the solubility of the polymeric binder in the solvent is at least 1 g/l, more preferably at least 5 g/l and especially preferably at least 10 g/l.

According to a particular embodiment of the present invention, the composition may preferably contain 0.1% to 10% by weight, more preferably 0.25% to 5% by weight and especially preferably 0.5% to 4% by weight of polymeric binder.

According to a particular embodiment, the polymeric binders preferably contain repeat units derived from styrene and/or olefins. Preferred polymeric binders may contain at least 80% by weight, preferably 90% by weight and more preferably 99% by weight of repeat units derived from styrene monomers and/or olefins.

Styrene monomers are well known in the art. These monomers include styrene, substituted styrenes having an alkyl substituent in the side chain, such as α-methylstyrene and α-ethylstyrene, substituted styrenes having an alkyl substituent on the ring, such as vinyltoluene and p-methylstyrene, halogenated styrenes such as monochlorostyrenes, dichlorostyrenes, tribromostyrenes and tetrabromostyrenes.

Olefins are monomers consisting of hydrogen and carbon atoms. These monomers include ethylene, propylene, butylene, isoprene and 1,3-butadiene.

According to a particular aspect of the present invention, the polymeric binder is polystyrene having a weight-average molecular weight in the range from 50 000 to 2 000 000 g/mol, preferably 100 000 to 750 000 g/mol, more preferably in the range from 150 000 to 600 000 g/mol and especially preferably in the range from 200 000 to 500 000 g/mol.

According to a further embodiment of the present invention, the polymeric binder is poly-4-methylstyrene having a weight-average molecular weight in the range from 40 000 to 120 000 g/mol, more preferably in the range from 60 000 to 100 000 g/mol.

More particularly, the binder may be poly-o-methylstyrene having a weight-average molecular weight in the range from 1000 to 20 000 g/mol, more preferably in the range from 1500 to 6000 g/mol.

Useful and preferred polymeric binders have Hansen solubility parameters of $H_d$ in the range from 15.7 to 23.0 MPa$^{0.5}$, $H_p$ in the range from 0.0 to 20.0 MPa$^{0.5}$ and $H_h$ in the range from 0.0 to 12.5 MPa$^{0.5}$. Particularly preferred polymeric binders have Hansen solubility parameters of $H_d$ in the range from 17.0 to 21.0 MPa$^{0.5}$, $H_p$ in the range from 1.0 to 5.0 MPa$^{0.5}$ and $H_h$ in the range from 2.0 to 10.0 MPa$^{0.5}$. Especially preferred polymeric binders have Hansen solubility parameters of $H_d$ in the range from 19.0 to 21.0 MPa$^{0.5}$, $H_p$ in the range from 1.0 to 3.0 MPa$^{0.5}$ and $H_h$ in the range from 2.5 to 5.0 MPa$^{0.5}$.

The Hansen solubility parameters can be determined by the program Hansen Solubility Parameters in Practice (HSPiP) (2nd edition) as obtainable from Hanson and Abbot et al.

Examples of useful polymeric binders are disclosed in table 1 of WO 2011/076325 A1.

According to a preferred embodiment of the present invention, the inert binder is a polymer having a glass transition temperature in the range from −70 to 160° C., preferably 0 to 150° C., more preferably 50 to 140° C. and especially preferably 70 to 130° C. The glass transition temperature can be determined by measuring the DSC of the polymer (DIN EN ISO 11357, heating rate 10° C. per minute).

The formulation according to the present invention may additionally contain one or more further components, for example surface-active compounds, lubricants, wetting agents, dispersants, hydrophobizing agents, adhesives, flow improvers, defoamers, devolatilizing agents, diluents which may be reactive or non-reactive, auxiliaries, colourants, dyes or pigments, sensitizers, stabilizers, nanoparticles or inhibitors. However, these further components should not be oxidizing or otherwise capable of reacting chemically with the organic semiconductor material or of exerting an electrical dopant effect on the organic semiconductor material.

Surprising improvements can be achieved with volatile wetting agents. The expression "volatile" as used above and below means that the agent can be removed from the organic semiconductor material(s) by evaporation after this/these material(s) has/have been deposited onto a substrate of an OLED device under conditions (such as temperature and/or reduced pressure) which do not significantly impair these materials or the OLED device. This preferably means that the wetting agent at the pressure used, very preferably at atmospheric pressure (1013 hPa), preferably has a boiling point or a sublimation temperature of <350° C., more preferably 300° C., especially preferably 250° C. The evaporation can also be accelerated, for example by using heat and/or reduced pressure.

Surprising effects can be achieved with formulations containing volatile components having similar boiling points. Preferably, the difference between the boiling point of the wetting agent and that of the organic solvent is in the range from −50° C. to 50° C., more preferably in the range from −30° C. to 30° C. and especially preferably in the range from −20° C. to 20° C.

Preferred wetting agents are nonaromatic compounds. Preference is further given to nonionic compounds as wetting agents. Particularly useful wetting agents have a surface tension of not more than 35 mN/m, preferably of not more than 30 mN/m and more preferably of not more than 25 mN/m. The surface tension can be measured with an FTA (First Ten Angstroms) 125 contact angle goniometer at 25° C. Details of the method are available from First Ten Angstroms, as published by Roger P. Woodward, Ph.D., "Surface Tension Measurements Using the Drop Shape Method". It is possible with preference to use the pendant drop method to determine the surface tension.

According to a particular aspect of the present invention, the difference between the surface tension of the organic solvent and that of the wetting agent is preferably at least 1 mN/m, preferably at least 5 mN/m and more preferably at least 10 mN/m.

According to a particular aspect of the present invention, the wetting agent may have a relative evaporation rate (butyl acetate=100) of at least 0.01, preferably of at least 0.1, more preferably of at least 0.5, especially preferably of at least 5, very especially preferably of at least 10 and particularly preferably of at least 20.

Unexpected improvements can be achieved with compositions comprising solvents and wetting agents having a similar relative evaporation rate (butyl acetate=100). Preferably, the difference between the relative evaporation rate (butyl acetate=100) of the wetting agent and that of the organic solvent is in the range from −20 to 20, more preferably in the range from −10 to 10. According to a preferred embodiment of the present invention, the ratio of the relative evaporation rate (butyl acetate=100) of the wetting agent to the relative evaporation rate (butyl acetate=100) of the organic solvent may be in the range from 230:1 to 1:230, preferably from 20:1 to 1:20 and more preferably from 5:1 to 1:5.

Unexpected improvements can be achieved by means of wetting agents having a molecular weight of at least 100 g/mol, preferably at least 150 g/mol, more preferably at least 180 g/mol and especially preferably at least 200 g/mol.

Suitable and preferred wetting agents which are not oxidized and do not react chemically in any other way with the OSC materials are selected from the group consisting of siloxanes, alkanes, amines, alkenes, alkynes, alcohols and/or halogenated derivatives of these compounds. In addition, it is possible to use fluoro ethers, fluoro esters and/or fluoro ketones. These compounds are more preferably selected from methylsiloxanes having 6 to 20 carbon atoms, especially 8 to 16 carbon atoms; $C_7$-$C_{14}$ alkanes, $C_7$-$C_{14}$ alkenes, $C_7$-$C_{14}$ alkynes, alcohols having 7 to 14 carbon atoms, fluoro ethers having 7 to 14 carbon atoms, fluoro esters having 7 to 14 carbon atoms and fluoro ketones having 7 to 14 carbon atoms. Especially preferred wetting agents are methylsiloxanes having 8 to 14 carbon atoms.

Examples of compounds useful and preferred as wetting agents are disclosed in WO 2011/076325 A1.

Preferably, the formulation contains preferably not more than 5% by weight, more preferably not more than 3% by weight and especially preferably not more than 1% by weight of wetting auxiliaries. Preferably, the composition contains 0.01% to 5% by weight, more preferably 0.05% to 3% by weight and especially preferably 0.1% to 1% by weight of wetting agents.

The formulations can be produced with the aid of methods very familiar to those skilled in the art. Typically, the individual components of the formulation are mixed and stirred, optionally also while supplying heat. Frequently, the formulation is also degassed or produced with solvents oversaturated with inert gases. Overall, it should be ensured that only solvents and other components of very high purity are used, in order to avoid contamination of the electronic devices with damaging compounds. More particularly, it should be ensured that the water, oxygen and halogen content in the formulation is kept low, since the performance data of organic electroluminescent devices in particular can be greatly impaired by the presence thereof.

The inventive organic TADF compound may, as already explained, be used as emitter in electronic devices. In a further embodiment of the present invention, the TADF compound may also be used as matrix material. In this case, the TADF compound transfers its energy to an emitter which ultimately emits radiation from the electronic device. Suitable emitters for this purpose are in principle any emitters, i.e. both organic fluorescent or organic phosphorescent and inorganic emitters, for example quantum dots and quantum rods, which are also referred to collectively as nanoparticles. The use of TADF compounds as matrix enables electronic devices having particularly advantageous performance data. It is particularly preferable when the emitter is a nanoparticle.

It is therefore very advantageous when the formulation contains nanocrystalline compounds or nanoparticles. The nanocrystals and nanoparticles include the quantum dots (QDs) and quantum rods (QRs). With the aid of these compounds, it is possible to inexpensively produce efficient OLEDs and other organic electronic devices which exhibit a very low failure rate and exhibit emission with narrow bands. In addition, it is possible to obtain emitting compounds which exhibit excellent colour purities and colour qualities (CRI—colour rendering index). In addition, the emission colour (CIE 1931 RGB) of such OLEDs can be adjusted very easily and accurately.

It is very particularly preferable when the formulation, as well as nanoparticles and TADF compound(s), also comprises further matrix compounds, preferably the abovementioned electron-transporting matrix compounds or the abovementioned hole-transporting matrix compounds.

Both quantum dots and quantum rods can be produced in a very simple manner. The size of the particles, the determining factor for the colour of the radiation emitted, is easily adjustable. In addition, quantum dots and quantum rods are soluble in many standard solvents and are of very good suitability for solution-based production processes.

The first monodisperse colloidal quantum dots comprising a semiconductive material were based on CdE (E=S, Se, Te) and were produced with the aid of what is called the TOPO (trioctylphosphine oxide) method (J. Am. Chem. Soc. 115[19], 8706-8715, 1993).

The person skilled in the art is aware of a multitude of methods for production of quantum dots and quantum rods, preference being given to using solution-based methods involving colloidal systems for controlled growth of inorganic quantum dots (Science 271:933 (1996); J. Am. Chem. Soc. 30:7019-7029 (1997); J. Am. Chem. Soc. 115:8706 (1993)).

Suitable semiconductors which are used in quantum dots and quantum rods are selected from the group of semiconductors consisting of
group II-VI elements, for example CdSe, CdS, CdTe, ZnSe, ZnO, ZnS, ZnTe, HgS, HgSe, HgTe and mixtures thereof, for example CdZnSe;
group III-V elements, for example InAs, InP, GaAs, GaP, InN, GaN, InSb, GaSb, AlP, AlAs, AlSb and mixtures thereof, for example InAsP, CdSeTe, ZnCdSe, InGaAs;
group IV-VI elements, for example PbSe, PbTe and PbS and mixtures thereof;
group III-VI elements, for example InSe, InTe, InS, GaSe and mixtures thereof, for example InGaSe, InSeS;
group IV elements, for example Si and Ge and mixtures thereof, and mixtures of the aforementioned materials.

Further suitable semiconductors for quantum dots and quantum rods include those which are disclosed in U.S. Ser. No. 10/796,832 and include any kind of semiconductors comprising group II-VI, III-V, IV-VI and IV element semiconductors. A selection of particularly suitable semiconductors is Si, Ge, Sn, Se, Te, B, C (including diamond), P, BN, BP, BAs, AlN, AlP, AlAs, AlS, AlSb, BaS, BaSe, BaTe, CaS, CaSe, CaTe, GaN, GaP, GaAs, GaSb, InN, InP, InAs, InSb, AlN, AlP, AlAs, AlSb, GaN, GaP, GaAs, GaSb, ZnO, ZnS, ZnSe, ZnTe, CdS, CdSe, CdTe, HgS, HgSe, HgTe, BeS, BeSe, BeTe, MgS, MgSe, GeS, GeSe, GeTe, SnS, SnSe, SnTe, PbO, PbS, PbSe, PbTe, CuF, CuCl, CuBr, CuI, $Si_3N_4$, $Ge_3N_4$, $Al_2O_3$, $(Al, Ga, In)_2 (S, Se, Te)_3$, $Al_2CO$, and a suitable combination of two or more of the semiconductors mentioned.

It is preferable when the quantum dots or quantum rods are selected from elements of groups II-VI, III-V, IV-VI and IV semiconductors, very preferably from ZnO, ZnS, ZnSe, ZnTe, CdS, CdSe, CdTe, HgS, HgSe, HgTe, MgS, MgSe, GeS, GeSe, GeTe, SnS, SnSe, SnTe, PbO, PbS, PbSe, PbTe, GaN, GaP, GaAs, GaSb, InN, InP, InAs, InSb, AlN, AlP, AlAs, AlSb, GaN, GaP, GaAs, GaSb, and a combination of these.

In QDs and QRs, photoluminescence and electroluminescence arise from the band edge states of the nanoparticle. The radiative band-edge emission from nanoparticles competes with non-radiative decay channel originating from surface electronic states, as reported by X. Peng, et al., J. Am. Chem. Soc. Vol. 119:7019-7029 (1997).

Particularly advantageous quantum dots and quantum rods have also been found to be those having a core-shell structure (J. Am. Chem. Soc. Vol. 119:7019-7029 (1997)).

Core-shell structures can be obtained when organometallic precursors containing the shell materials are used as precursors. These precursors are added to a reaction mixture comprising the core nanoparticles. Further details of the production process are well known to those skilled in the art from the prior art.

In a preferred embodiment, ZnS is used as shell material.

It is further preferable when the quantum dots and quantum rods are semiconductive materials of group II-VI, mixtures thereof and core-shell structures thereof. Very preferred in this context are CdSe, CdS, CdTe, ZnSe, ZnS, ZnTe and mixtures thereof.

The quantum dots and quantum rods may contain further ligands bound to the surface of the particles. Suitable ligands for the purpose are well-known in the prior art and are, for example, disclosed in U.S. Ser. No. 10/656,910 and U.S. 60/578,236. In this way, it is possible to improve various properties of the quantum dots and quantum rods. In this way, it is possible to improve solubility in particular solvents, matrix materials and polymers. Further preferred ligands are disclosed in US 2007/0034833A1 and US 20050109989A1.

The terms "quantum dot" and "quantum rod" used herein represent nanoparticles having essentially a monodisperse size distribution. The dimension of the particles is 500 nm or less, up to and including a dimension of about 1 nm. "Monodisperse" means that the particles have a size distribution of +−10% of said dimension of the particles.

Typical structures and methods for production of quantum rods are disclosed in US 2013/0135558 A1.

The inventive formulations can be used to produce layers in electronic devices, the layers which are produced by means of the inventive formulation being applied from solution.

In the production of organic electronic devices, for example the OLEDs, a distinction is made between two fundamentally different methods. In the first method, the relevant compounds are applied by vapour deposition under reduced pressure. This method is very inconvenient and costly. In the second method, the relevant compounds are applied from solution.

Particular electronic devices are constructed from multilayer systems. In the production of such multilayer systems, it is possible to use both the abovementioned methods. Frequently, individual layers are applied by vapour deposition, while other layers are processed from solution.

The present invention therefore further provides a process for producing an organic electronic device, characterized in that at least one layer of the electronic device is produced from solution with the aid of the inventive formulation.

Typical methods for production of layers from solution are, for example, spin-coating or any desired printing method, for example screen printing, flexographic printing, offset printing or nozzle printing, but more preferably LITI (light-induced thermal imaging, thermal transfer printing) or inkjet printing. Formulations are required for this purpose.

The organic electronic devices are preferably an organic integrated circuit (OIC), an organic field-effect transistor (OFET), an organic thin-film transistor (OTFT), an organic electroluminescent device, an organic solar cell (OSC), an organic optical detector, an organic photoreceptor, but preferably an organic electroluminescent device.

Very preferred organic electroluminescent devices are the organic light-emitting transistors (OLETs), organic field quench devices (OFQDs), organic light-emitting electrochemical cells (OLECs, LECs, LEECs), organic laser diodes (O-lasers) and organic light-emitting diodes (OLEDs), preferably OLECs and OLEDs, very preferably OLEDs.

The organic electroluminescent device comprises cathode, anode, emitting layer and at least one adjoining electron transport layer on the cathode side. Apart from these layers, it may also comprise further layers, for example in each case one or more hole injection layers, hole transport layers, further electron transport layers, electron injection layers, exciton blocker layers, electron blocker layers and/or charge generation layers. However, it should be pointed out that not necessarily every one of these layers need be present.

In the further layers of the inventive organic electroluminescent device, especially in the hole injection and transport layers and in the electron injection and transport layers, it is possible to use any materials as typically used according to the prior art. The hole transport layers may also be p-doped or the electron transport layers may also be n-doped. A p-doped layer is understood to mean a layer in which free holes have been generated and which has increased conductivity as a result. A comprehensive discussion of doped transport layers in OLEDs can be found in Chem. Rev. 2007, 107, 1233. More preferably, the p-dopant is capable of oxidizing the hole transport material in the hole transport layer, i.e. has a sufficiently high redox potential, especially a higher redox potential than the hole transport material. Suitable dopants are in principle any compounds which are electron acceptor compounds and which can increase the conductivity of the organic layer by oxidizing the host. The person skilled in the art, in the context of his common knowledge in the art, is able to identify suitable compounds without any great effort. Especially suitable dopants are the compounds disclosed in WO 2011/073149, EP 1968131, EP 2276085, EP 2213662, EP 1722602, EP 2045848, DE 102007031220, U.S. Pat. Nos. 8,044,390, 8,057,712, WO 2009/003455, WO 2010/094378, WO 2011/120709 and US 2010/0096600.

The person skilled in the art will therefore be able, without exercising inventive skill, to use all the materials known for organic electroluminescent devices in combination with the emitting layer comprising the inventive TADF compounds.

More particularly, it may be preferable when further electron transport layers and/or electron injection layers are present between the inventive electron transport layer and the cathode.

An electron transport layer in the context of the present invention is a layer disposed between the cathode or the electron injection layer and the emitting layer. An electron injection layer in the context of the present invention is a layer which directly adjoins the cathode and has a layer thickness of not more than 5 nm, preferably 0.5 to 5 nm.

At the same time, preferably all the electron transport layers, i.e. all the layers present between the cathode or, if present, the electron injection layer and the emitting layer, contain at least one compound having a LUMO $5 \leq -2.55$ eV.

In order that the emission of the TADF compound is not quenched at the directly adjoining electron transport layer, it is preferable that the lowest triplet energy of this electron transport layer is not more than 0.1 eV lower than the triplet energy of the molecule which exhibits TADF. Especially preferably, $T_1(ETL) \geq T_1(TADF)$. More preferably: $T_1(ETL)-T_1(TADF) \geq 0.1$ eV, most preferably $T_1(ETL)-T_1(TADF) \geq 0.2$ eV. $T_1(ETL)$ here is the lowest triplet energy of the electron transport layer directly adjoining the emitting layer, and $T_1(TADF)$ is the lowest triplet energy of the TADF compound. The triplet energy of the materials of the electron transport layer is determined here by quantum chemistry methods disclosed in a general and detailed manner in the examples section. When the electron transport layer contains more than one compound, the condition for the triplet energy preferably applies to each of the compounds.

The abovementioned conditions for the triplet energy are preferable only for the electron transport layer directly adjoining the emitting layer. If further electron transport layers are present on the cathode side of the electron transport layer directly adjoining the emitting layer, the triplet energy is unimportant for these further electron transport layers, and so it is also possible here to choose electron transport materials having a lower triplet energy, for example anthracene derivatives.

The electron transport layer directly adjoining the emitting layer on the cathode side may also act as a hole blocker layer, and can thus simultaneously also, apart from electron-transporting properties, have hole-blocking properties. This depends on the position of the HOMO level of the layer. More particularly, the layer acts as a hole blocker layer when the following is true for the HOMO of the layer: HOMO (EML)−HOMO(ETL)>0.2 eV, preferably HOMO(EML)−HOMO(ETL)>0.3 eV. HOMO(ETL) is the HOMO of the material of the electron transport layer. If this layer consists of two or more materials, HOMO(ETL) is the highest HOMO of these materials. HOMO(EML) is the HOMO of the material of the emitting layer. If this layer consists of two or more materials, HOMO(EML) is the highest HOMO of these materials. In each case, the HOMO (highest occupied molecular orbital) is determined by quantum-chemical calculations, as explained in general terms at the back in the examples section.

For clarification, it should be emphasized that the values for HOMO and LUMO are negative numerical values by definition. The highest HOMO is therefore the smallest HOMO in terms of magnitude, and the lowest LUMO is the greatest LUMO in terms of magnitude.

The electron transport layer may take the form of a pure layer, i.e. consist only of one compound, which then preferably has a LUMO of 5≤−2.55 eV. The layer may also take the form of a mixture, in which case at least one of the compounds preferably has a LUMO of ≤−2.55 eV. This compound is present in the layer in a proportion of preferably at least 30% by volume, more preferably at least 50% by volume, most preferably at least 70% by volume. Especially preferably, the layer takes the form of a pure layer, meaning that it consists solely of a compound preferably having a LUMO of ≤−2.55 eV. When the electron transport layer contains a mixture of two or more materials, it is preferable when each of these materials has a LUMO of ≤−2.55 eV.

Suitable electron transport materials for use in the electron transport layer are selected from the substance classes of the triazines, the pyrimidines, the lactams, the metal complexes, especially the Be, Zn and Al complexes, the aromatic ketones, the aromatic phosphine oxides, the azaphospholes, the azaboroles substituted by at least one electron-conducting substituent, the benzimidazoles, the oxadiazoles and the quinoxalines.

Preferred cathodes of the inventive electroluminescent device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. Likewise preferred are metal alloys, especially alloys composed of an alkali metal or alkaline earth metal and silver, more preferably an alloy composed of Mg and Ag. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, CsF, $Cs_2CO_3$, $BaF_2$, MgO, NaF, etc.). Likewise useful are organic alkali metal or alkaline earth metal complexes, for example lithium quinolinate (LiQ). The layer thickness of this layer, which should be regarded as an electron injection layer, is preferably between 0.5 and 5 nm.

Preferred anodes of the inventive electroluminescent device are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. $Al/Ni/NiO_x$, $Al/PtO_x$) may also be preferable. In this case, at least one of the electrodes has to be transparent or semitransparent in order to enable the emission of light. Preferred transparent or semitransparent anode materials are conductive mixed metal oxides. Particular preference is given to indium tin oxide (ITO) or indium zinc oxide (IZO). Preference is further given to conductive doped organic materials, especially conductive doped polymers.

The device is correspondingly (according to the application) structured, contact-connected and finally hermetically sealed, since the lifetime of such devices is severely shortened in the presence of water and/or air.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution. These methods are especially also suitable for oligomers, dendrimers and polymers.

These methods are known in general terms to those skilled in the art and can be applied without exercising inventive skill to organic electroluminescent devices comprising the inventive compounds.

The present invention therefore further provides a process for producing an inventive organic electroluminescent device, characterized in that at least one layer is applied by a sublimation method and/or in that at least one layer is applied by an OVPD (organic vapour phase deposition) method or with the aid of a carrier gas sublimation and/or in that at least one layer is applied from solution, by spin-coating or by a printing method.

The inventive TADF compounds, compositions, formulations and devices feature one or more of the following surprising advantages over the prior art:

1. The inventive organic TADF compounds are very easy to prepare.
2. The inventive organic TADF compounds have improved solubility in organic solvents which are typically used for production of electronic devices.
3. Devices, especially organic electroluminescent devices, produced with the aid of the inventive formulations have comparable efficiencies and voltages to devices from the prior art.
4. Organic electronic devices, especially organic electroluminescent devices, produced with the aid of the inventive formulations are easy and inexpensive to produce and are therefore particularly suitable for the mass production of commercial products.
5. With the aid of the inventive formulations, it is possible in a very simple and inexpensive manner to produce layers of organic electronic devices, especially in organic electroluminescent devices comprising several components, for example several matrix compounds.
6. With the aid of the inventive formulations, the production processes can be matched very easily to new demands.
7. The use of the inventive formulations for production of organic electronic devices leads to very reliable production processes, especially also because of a reduced failure rate.
8. The number of short circuits in electronic devices comprising the inventive compounds or compositions is much reduced compared to the prior art devices.

9. The stability of the emitters in the emission layer can be improved through use of the TADF compounds compared to the prior art.
10. The inventive compounds can be used in relatively high concentrations in electronic devices, which has an advantageous effect on the efficiency of the devices.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Any feature disclosed in the present invention, unless stated otherwise, should therefore be considered as an example from a generic series or as an equivalent or similar feature.

All features of the present invention may be combined with one another in any manner, unless particular features and/or steps are mutually exclusive. This is especially true of preferred features of the present invention.

Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby. The person skilled in the art will be able to use the information given to execute the invention over the entire scope disclosed and produce further inventive organic electroluminescent devices without exercising inventive skill.

EXAMPLES

Example 1

Determination Methods
Quantum Chemistry Method for Determining Orbital Energies and Electronic States The HOMO and LUMO energies and the triplet level and singlet levels of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "# AM1 opt") with charge 0 and multiplicity 1. Subsequently, on the basis of the optimized geometry, a single-point energy calculation is effected for the electronic ground state and the triplet level. This is done using the TDDFT (time dependent density functional theory) method B3PW91 with the 6-31G(d) basis set (Gaussian input line "# B3PW91/6-31G(d) td=(50-50, nstates=4)") (charge 0, multiplicity 1). For organometallic compounds (referred to as the "M-org." method), the geometry is optimized by the Hartree-Fock method and the LanL2 MB basis set (Gaussian input line "# HF/LanL2 MB opt") (charge 0, multiplicity 1). The energy calculation is effected, as described above, analogously to that for the organic substances, except that the "LanL2DZ" basis set is used for the metal atom and the "6-31G(d)" basis set for the ligands (Gaussian input line "# B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. This is used to determine the HOMO and LUMO value in electron volts, calibrated by cyclic voltammetry measurements, as follows:

$$HOMO(eV)=(HE_h*27.212)*0.8308-1.118$$

$$LUMO(eV)=(LE_h*27.212)*1.0658-0.5049$$

These values are to be regarded as HOMO and as LUMO of the materials in the context of this application.

The triplet level $T_1$ of a material is defined as the relative excitation energy (in eV) of the triplet state having the lowest energy which is found by the quantum-chemical energy calculation.

The singlet level $S_1$ of a material is defined as the relative excitation energy (in eV) of the singlet state having the second-lowest energy which is found by the quantum-chemical energy calculation.

The energetically lowest singlet state is referred to as $S_0$.

The method described herein is independent of the software package used and always gives the same results. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01".

Table 3 states the HOMO and LUMO energy values and $S_1$ and $T_1$ of the various materials.

Determination of Orbital Overlap

The overlap of the molecular orbitals involved in particular electronic transitions (charge transfer states) is described with the aid of the parameter $\Lambda$. The meaning of this parameter $\Lambda$ is well known to those skilled in the art. The determination of the parameter by means of methods described in the prior art does not present any difficulties at all to the person skilled in the art. In the context of the present invention, the parameter $\Lambda$ is determined by the PBHT method according to D. J. Tozer et al. (J. Chem. Phys. 128, 044118 (2008)), which is implemented, for example, in the Q-Chem 4.1 software package from Q-Chem, Inc. This calculates the molecular orbitals by the method described above. Subsequently, the spatial overlaps for all possible pairs of occupied molecular orbitals, $\varphi_i$, and unoccupied (virtual) molecular orbitals, $\varphi_a$, is determined by the following equation:

$$O_{ia}=\langle |\varphi_i| \| \varphi_a| \rangle$$

where the magnitudes of the orbitals are used for the calculation.

The parameter $\Lambda$ is then found from the weighted sum total over all the pairs is of occupied and unoccupied molecular orbitals according to $$\Lambda = \frac{\sum_{ia} \kappa_{ia}^2 O_{ia}}{\sum_{ia} \kappa_{ia}^2}$$

where the value of $\kappa_{ia}$ according to Tozer et al. is determined from the orbital coefficients in the excitation vectors of the solved TD (time-dependent) eigenvalue calculation and where $0 \leq \Lambda \leq 1$.

Determination of PL Quantum Efficiency (PLQE)

A 50 nm-thick film of the emission layers used in the different OLEDs is applied to a suitable transparent substrate, preferably quartz, meaning that the layer contains the same materials in the same concentration as in the OLED. This is done using the same production conditions as in the production of the emission layer for the OLEDs. An absorption spectrum of this film is measured in the wavelength range of 350-500 nm. For this purpose, the reflection spectrum $R(\lambda)$ and the transmission spectrum $T(\lambda)$ of the sample are determined at an angle of incidence of 6° (i.e. incidence virtually at right angles). The absorption spectrum in the context of this application is defined as $A(\lambda)=1-R(\lambda)-T(\lambda)$.

If $A(\lambda) \leq 0.3$ in the range of 350-500 nm, the wavelength corresponding to the maximum of the absorption spectrum in the range of 350-500 nm is defined as $\lambda_{exc}$. If, for any wavelength, $A(\lambda) > 0.3$, $\lambda_{exc}$ is defined as being the greatest wavelength at which $A(\lambda)$ changes from a value of less than 0.3 to a value of greater than 0.3 or from a value of greater than 0.3 to a value of less than 0.3.

The PLQE is determined using a Hamamatsu C9920-02 measurement system. The principle is based on the excitation of the sample with light of a defined wavelength and the measurement of the radiation absorbed and emitted. During the measurement, the sample is within an Ulbricht sphere ("integrating sphere"). The spectrum of the excitation light is approximately Gaussian with a half-height width of <10 nm and a peak wavelength $\lambda_{exc}$ as defined above.

The PLQE is determined by the evaluation method customary for said measurement system. It should be strictly ensured that the sample does not come into contact with oxygen at any time, since the PLQE of materials having a small energy gap between $S_1$ and $T_1$ is very greatly reduced by oxygen (H. Uoyama et al., Nature 2012, Vol. 492, 234).

Table 2 states the PLQE for the emission layers of the OLEDs as defined above together with the excitation wavelength used.

Determination of Decay Time

The decay time is determined using a sample which has been produced as described above under "Determination of the PL quantum efficiency (PLQE)". The measurement is effected under reduced pressure. The sample is excited at room temperature by a laser pulse of suitable intensity (wavelength 266 nm, pulse duration about 1.5 ns). After excitation (defined as t=0), the profile of the photoluminescence emitted against time is measured. For the measurement data from time t=250 ns, the decay time $t_a = t_e - 250$ ns is determined. In this formula, $t_e$ is that time after t=250 ns at which the intensity has for the first time dropped to 1/e of its value at t=250 ns.

Determination of Solubility

In order to examine whether a material has a toluene solubility of 10 mg/ml or more, the procedure is as follows: 20 mg of material in solid form are initially charged in a sample bottle. At room temperature (20° C.), 2 ml of toluene are added. The bottle is closed and the contents are stirred at 60° C. on a heatable magnetic stirrer for 1 h. In the course of this, good thermal contact is ensured by means of an aluminium block having holes into which the bottles fit exactly. After 1 h, the bottle is removed and left to cool to room temperature. If a clear solution lacking any large particles is present in the bottle, at least 10 mg/ml of the material are soluble in toluene.

Solubilities with other solubility limits are determined in entirely the same way. The starting weight is also matched to 2 ml of solvent.

Example 2

Synthesis of Compounds 6a to 6f

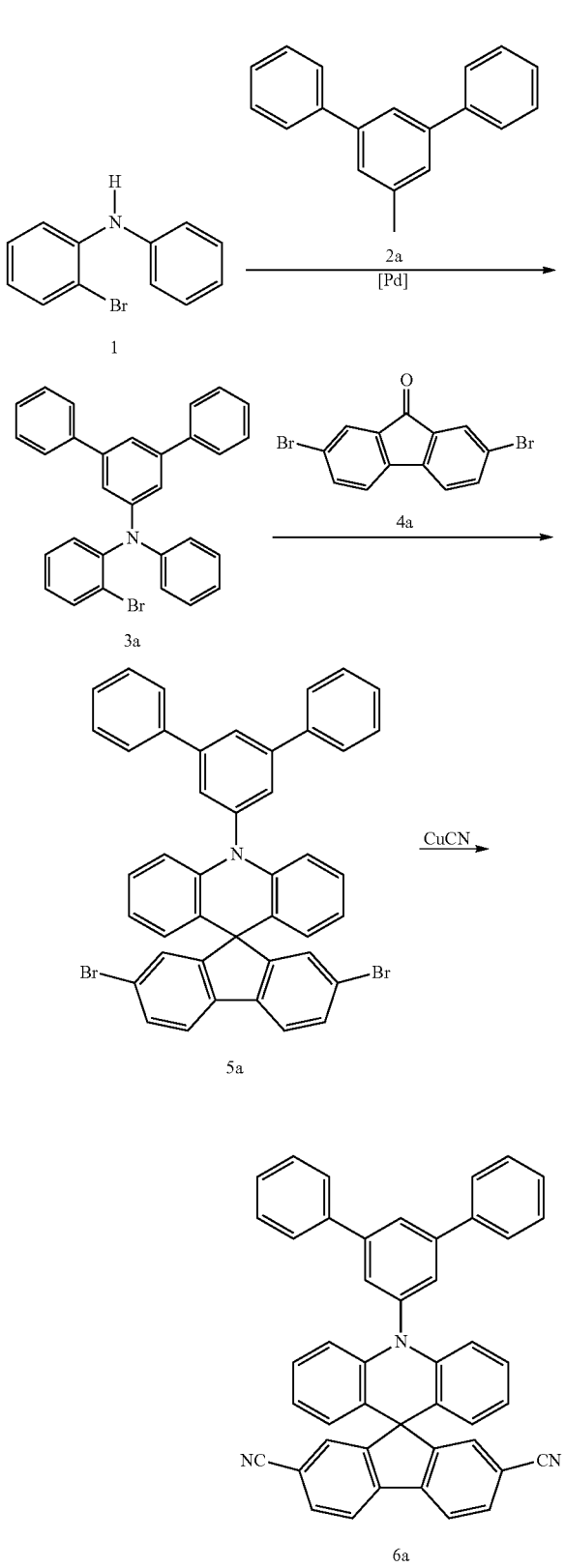

Stage 1

(2-Bromophenyl)phenyl[1,1;3',1"]terphenyl-5'-ylamine 3a

To a suspension of 50.0 g (200 mmol, 1.0 eq) of N-phenyl-2-bromoaniline [61613-22-7] and 85.5 g (240 mmol, 1.2 eq) of 5'-iodo-1,1':3',1"-terphenyl [87666-86-2] in 500 ml of toluene are added 23.1 g (240 mmol, 1.2 eq) of sodium tert-butoxide, and the mixture is degassed for 30 minutes. Subsequently, 1.35 g (6.0 mmol, 0.03 eq) of palladium(II) acetate and 10 ml (10 mmol, 0.05 eq) of a 1 N tri-tert-butyl phosphonate solution in toluene are added. The mixture is heated under reflux overnight and, after the reaction has ended, washed with water. The aqueous phase is extracted twice with toluene, the combined organic phases are dried over sodium sulphate and the solvent is removed on a rotary evaporator. 89.6 g (188 mmol, 94%) of a brownish oil are obtained.

The following are prepared analogously:

| No. | Reactant 2 | Product | Yield |
|---|---|---|---|
| 3b | 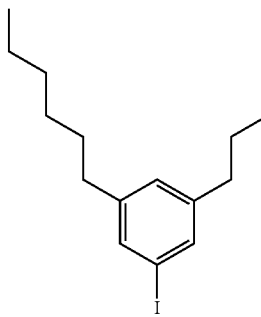 | 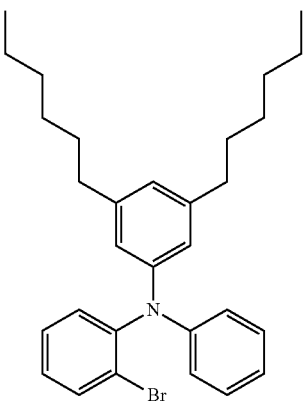 [SMILES: CCCCCCc1cc(CCCCCC)cc(N(c2ccccc2)c2ccccc2Br)c1] | 87% |
| 3c | 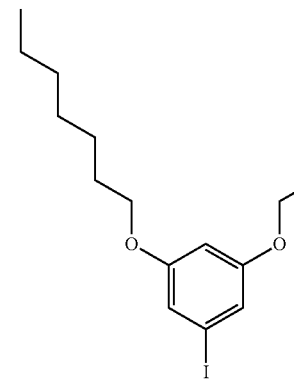  [1264968-31-1] | 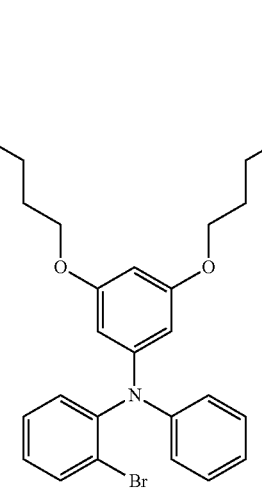 | 64% |
| 3d | 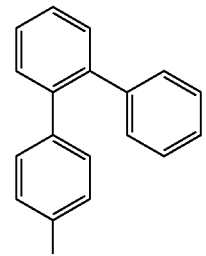  [24253-38-1] | 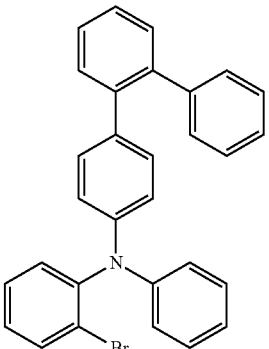 | 92% |

-continued
| No. | Reactant 2 | Product | Yield |
|---|---|---|---|
| 3e | 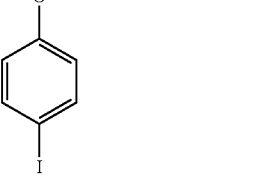 [1227071-97-7] | 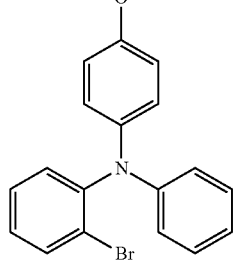 | 59% |
| 3f | 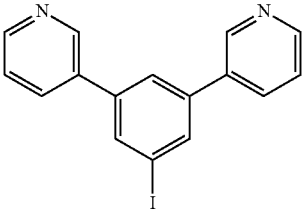 [1214386-08-9] | 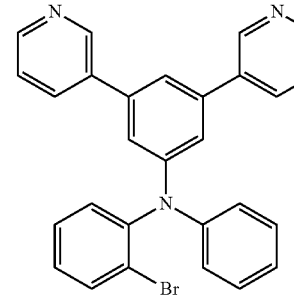 | 89% |
| 3g | 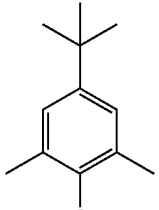 [5122-20-3] | 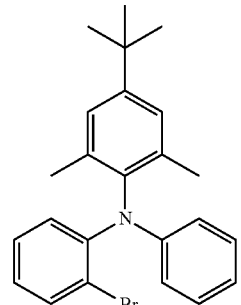 | 95% |
| 3h | 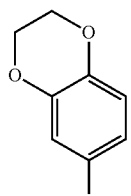 [57744-67-9] | 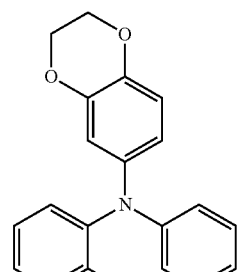 | 32% |

| No. | Reactant 2 | Product | Yield |
|---|---|---|---|
| 3i | 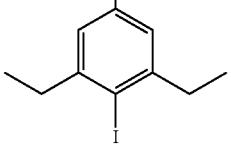 [2100-21-2] | 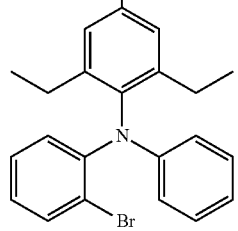 | 84% |
| 3j | 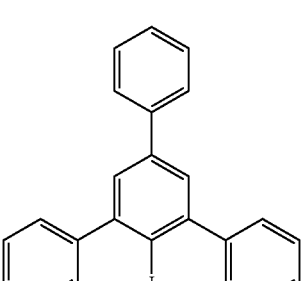 [97388-36-8] | 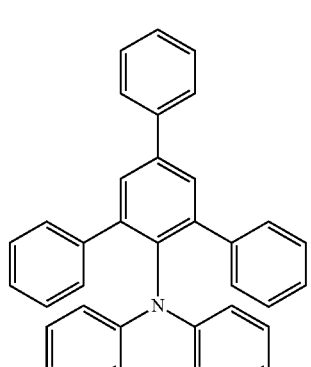 | 65% |

Stage 2

2',7'-Dibromo-10H-terphenyl-10H-spiro(acridine-9,9'-fluorene) 5a

A solution of 89.0 g (187 mmol, 1.0 eq) of the amine 3a is dissolved in 1 l of dried THF, and 75 ml of n-BuLi (187 mmol, 1.0 eq, 2.5 M in hexane) are added at −78° C. After the addition has ended, the reaction mixture is stirred at this temperature for one hour and then a solution of 63.2 g (187 mmol, 1.0 eq) in 400 ml of dried THF is added. The reaction mixture is stirred at −78° C. for a further 30 minutes and warmed to room temperature overnight. This is followed by quenching of the reaction with water, removal of the organic phase after addition of a little diethyl ether, and washing with water and saturated sodium chloride solution. The organic phase is dried over sodium sulphate and the solvent mixture is removed on a rotary evaporator. The isolated intermediate is added to a mixture of 100 ml of conc. HCl and 1 l of acetic acid and refluxed for 2 h. The reaction mixture is cooled, diluted with water and extracted with dichloromethane. The combined organic phases are washed with saturated sodium hydrogencarbonate solution and water, then dried over sodium sulphate, and the solvent is removed under reduced pressure. The resulting solid is recrystallized from toluene/heptane. 79.2 g (110 mmol, 59%) of a colourless solid are obtained.

The following are prepared analogously:
| No | Reactant 3 | Reactant 4 | Product 5 | Yield |
|---|---|---|---|---|
| 5b | 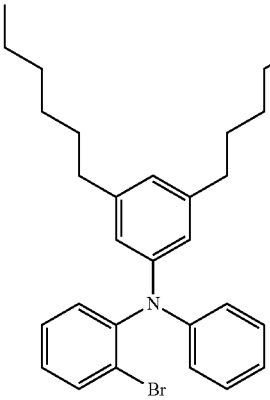 | 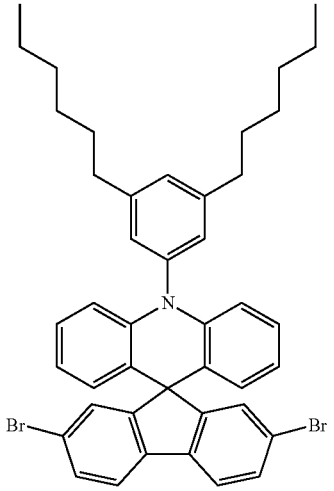 [SMILES: CCCCCCc1cc(CCCCCC)cc(N2c3ccccc3C3(c4cc(Br)ccc4-c4ccc(Br)cc43)c3ccccc32)c1][14348-75-5] | 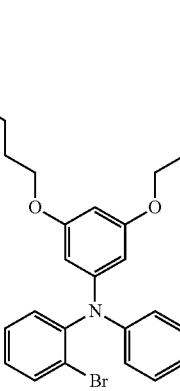 | 41% |
| 5c | 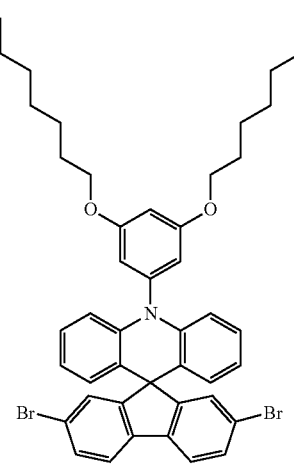 | 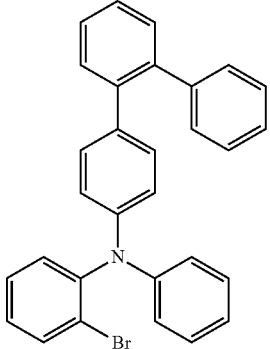 [SMILES: Brc1ccccc1N(c1ccccc1)c1ccc(-c2ccccc2-c2ccccc2)cc1][14348-75-5] | 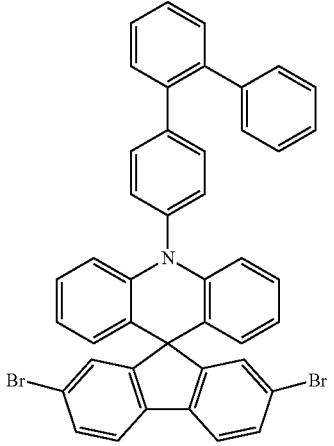 [SMILES: Brc1ccc2c(c1)C1(c3cc(Br)ccc3-2)c2ccccc2N(c2ccc(-c3ccccc3-c3ccccc3)cc2)c2ccccc21] | 32% |
| 5d |  | [14348-75-5] |  | 22% |

-continued

| No | Reactant 3 | Reactant 4 | Product 5 | Yield |
|---|---|---|---|---|
| 5e | | [14348-75-5] | | 54% |
| 5f | | [14348-75-5] | | 67% |
| 5g | | [84-65-1] | | 71% |

-continued

| No | Reactant 3 | Reactant 4 | Product 5 | Yield |
|---|---|---|---|---|
| 5h | | [84-65-1] | | 78% |
| 5i | | [84-65-1] | | 18% |
| 5j | | [84-65-1] | | 63% |

-continued

| No | Reactant 3 | Reactant 4 | Product 5 | Yield |
|---|---|---|---|---|
| 5k | | [84-65-1] | | 44% |
| 5k | | [84-65-1] | | 37% |

Stage 3

2',7'-Cyano-10H-terphenyl-10H-spiro(acridine-9,9'-fluorene) 6a

A mixture of 79.0 g (110 mmol, 1.0 eq) of the dibromide 5a and 24.6 g (275 mmol, 2.5 eq) of copper(1) cyanide [544-92-3] in 1.2 l of NMP is stirred at 170° C. for 24 h. After the reaction has ended, the solution is added to 2 N sodium hydroxide solution, and sodium hypochlorite is added. The resulting solution is stirred for half an hour and extracted with toluene. The combined organic phases are washed with water and dried over sodium sulphate, and the solvent is removed on a rotary evaporator (crude yield: 56.3 g, 92.4 mmol, 84%). The resulting solid is recrystallized repeatedly from toluene/heptane until a purity of >99.9% (HPLC) is attained. Finally, the product is purified by means of sublimation. 28.1 g (46.2 mmol, 42%) of the target compound in high purity are obtained.

The following are prepared analogously:

| No. | Reactant 5 | Product | Yield |
|---|---|---|---|
| 6b | (structure with 3,5-dihexylphenyl-acridine-spiro-fluorene-2,7-dibromide) | (structure with 3,5-dihexylphenyl-acridine-spiro-fluorene-2,7-dicyanide) not sublimed | 54% |
| 6c | (structure with 3,5-bis(octyloxy)phenyl-acridine-spiro-fluorene-2,7-dibromide) | (structure with 3,5-bis(octyloxy)phenyl-acridine-spiro-fluorene-2,7-dicyanide) not sublimed | 47% |
| 6d | (structure with ortho-terphenyl-phenyl-acridine-spiro-fluorene-2,7-dibromide) | (structure with ortho-terphenyl-phenyl-acridine-spiro-fluorene-2,7-dicyanide) | 68% |

| No. | Reactant 5 | Product | Yield |
|---|---|---|---|
| 6e | 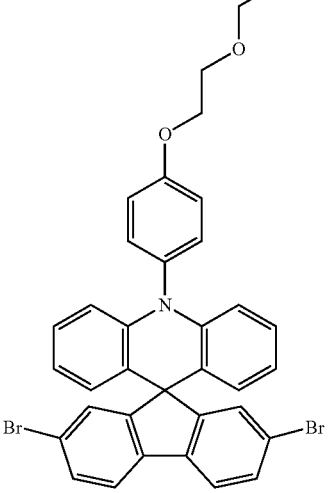 | 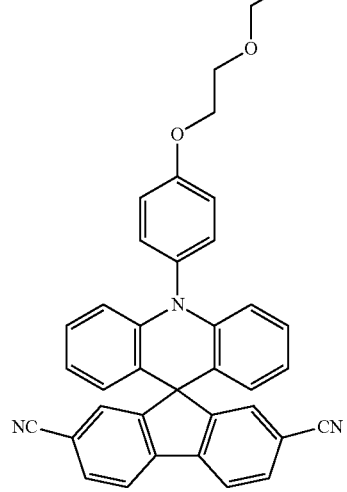<br>not sublimed | 33% |
| 6f |  |  | 71% |

Example 3

Synthesis of Compound 8a

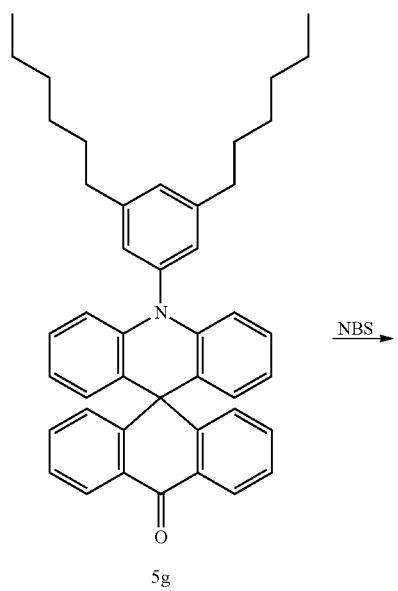

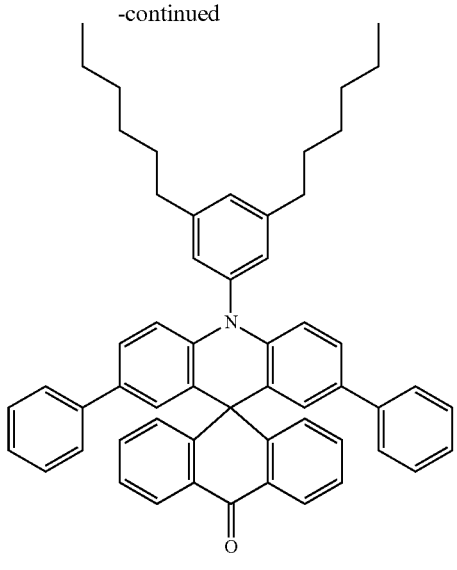

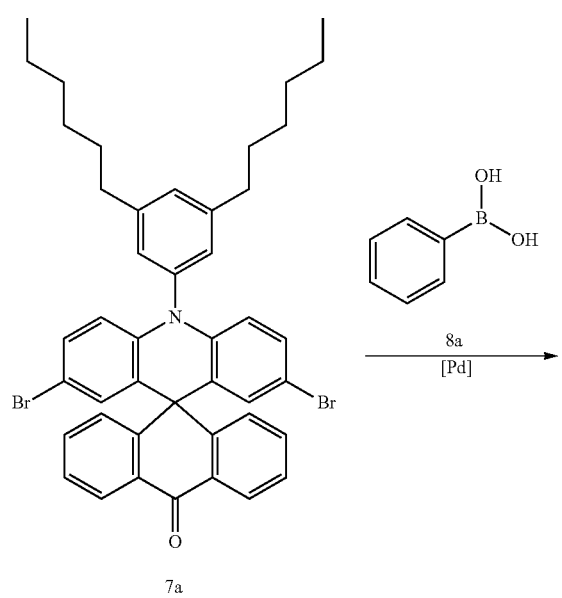
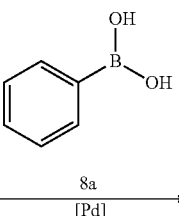

Stage 1

20 g (33 mol, 1.0 eq) of reactant 5 g are initially charged in 500 ml of DMF, and 12 g (68 mmol, 2.05 eq) of N-bromosuccinimide are added gradually. After three hours at room temperature, the precipitated solid is filtered off with suction and washed with ethanol. 24 g (31 mmol, 96%) of a beige solid 7a are obtained.

Stage 2

24 g (31 mmol, 1.0 eq) of the dibromide 7a, 9.5 g (78 mmol, 2.5 eq) of phenylboronic acid and 26 g (124 mmol, 4.0 eq) of tripotassium phosphate are initially charged, and 375 ml of toluene, 150 ml of dioxane and 375 ml of water are added. After the mixture has been degassed to 30 minutes, 70 mg (0.31 mmol, 0.01 eq) of palladium(II) acetate and 570 mg (1.9 mmol, 0.06 eq) of tri-o-tolylphosphine are added and the mixture is stirred at 85° C. overnight. After the reaction has ended, the phases are separated in a separating funnel, the organic phase is extracted with toluene and the combined organic phases are washed with water. The organic phase is subsequently dried over sodium sulphate and the solvent is removed on a rotary evaporator. 22 g (29 mmol, 93%) of a colourless solid are obtained, which is recrystallized repeatedly from toluene/heptane until an HPLC purity of >99.9% is achieved. Finally, the target product obtained is purified by means of sublimation. 11.5 g (15 mmol, 48%) of compound 8a in high purity are obtained.

Example 4

Synthesis of Compounds 9a to 9f

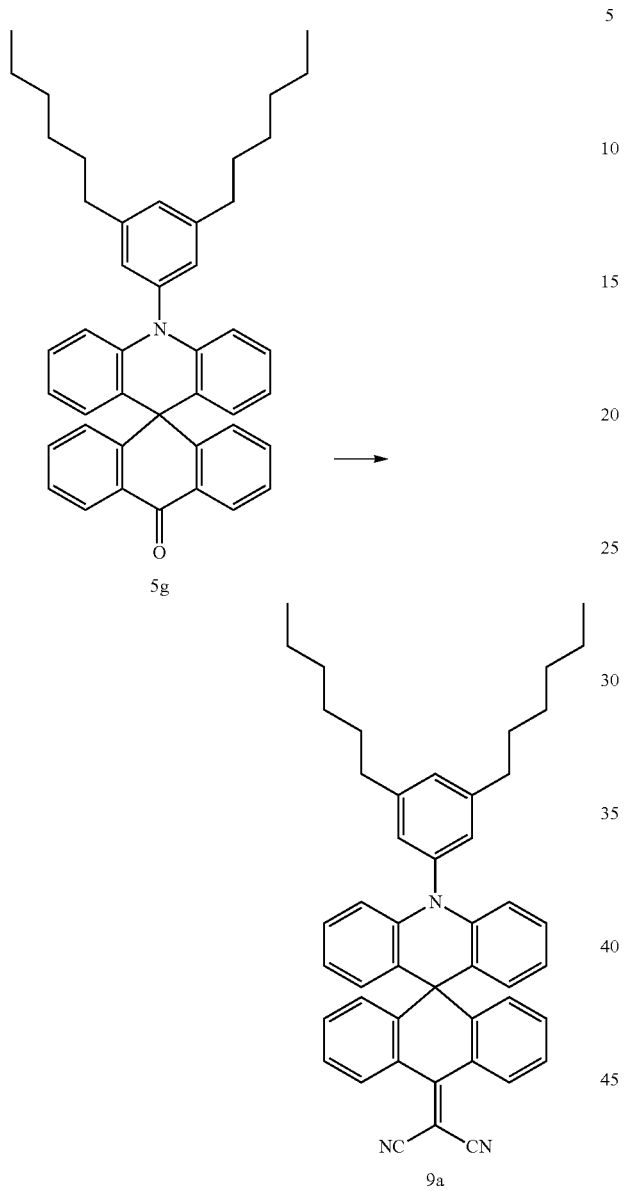

30 g (50 mmol, 1.0 eq) of the unpurified crude product 5 g are dissolved under protective gas together with 16.5 g (250 mmol, 5.0 eq) of malononitrile in 1.5 l of dichloromethane. Subsequently, 250 ml (250 mmol, 5.0 eq) of titanium (IV) chloride as a 1 M solution in dichloromethane are added gradually, followed by 20 ml (500 mmol, 10 eq) of dried pyridine. The reaction mixture is boiled under reflux for 24 hours and the same amounts again of malononitrile, titanium (IV) chloride and dried pyridine are added. After the mixture has been boiled again under reflux for 24 hours, 500 ml of dichloromethane are added and the organic phase is washed successively with 10% HCl and 5% NaOH. The organic phase is dried over sodium sulphate and the solvent is removed on a rotary evaporator. The resulting solid, 11.7 g (18 mmol, 36%) is recrystallized with toluene/heptane until an HPLC purity of >99.9% is achieved; finally, a sublimation is conducted. 3.6 g (5.5 mmol, 11%) of product 9a in high purity are obtained.

The following are prepared analogously:

| No | Reactant 8 | Product 9 | Yield |
|---|---|---|---|
| 9b | | | 14% |
| 9c | | | 9% |
| 9d | | | 24% |

-continued
| No | Reactant 8 | Product 9 | Yield |
|---|---|---|---|
| 9e | 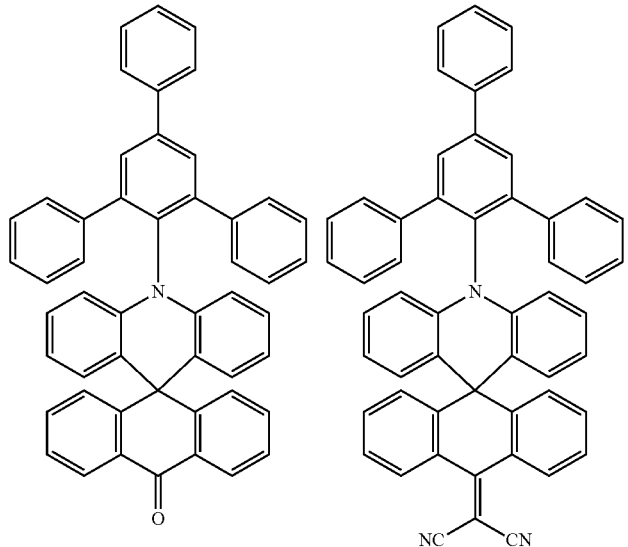 | | 21% |
| 9f | 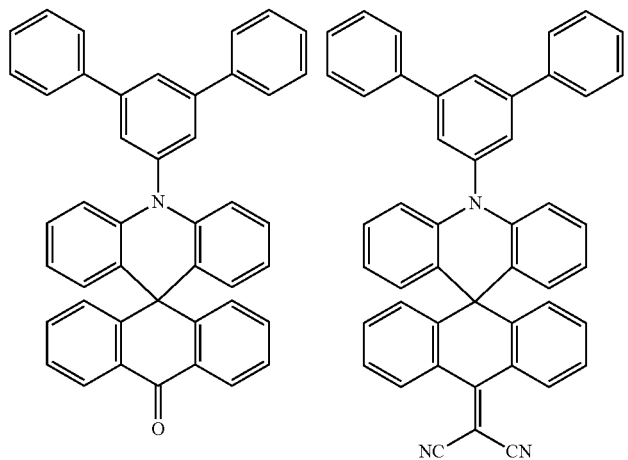 | | 13% |

Example 5
Synthesis of Compounds 14a to 14i
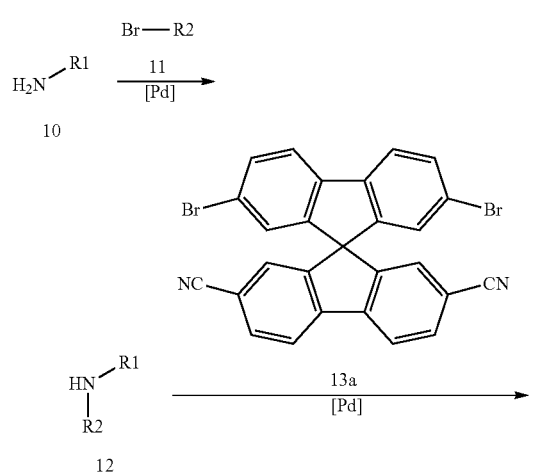
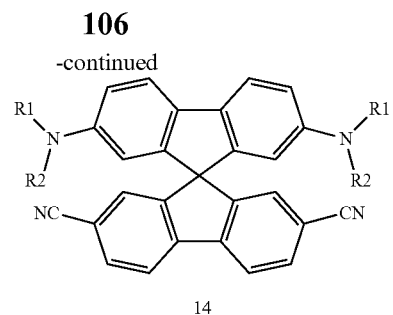
Stage 1
Formation of secondary amines 12a to 12h
The synthesis is conducted in accordance with the method for compound 3a.
The following are obtained analogously:
| No. | Reactant 10 | Reactant 11 | Product 12 | Yield |
|---|---|---|---|---|
| 12a | [343239-58-7] | [28320-31-2] | | 64% |
| 12b | [104-13-2] | [41492-05-1] | | 57% |

-continued
| No. | Reactant 10 | Reactant 11 | Product 12 | Yield |
|---|---|---|---|---|
| 12c | 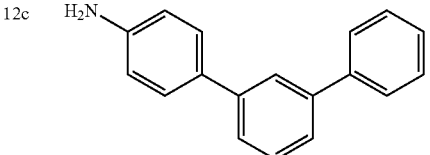 [78626-54-7] | 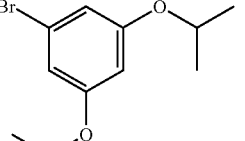 [1310418-54-2] | 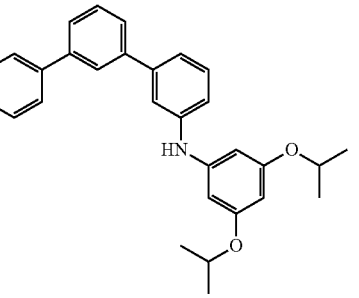 | 61% |
| 12d | 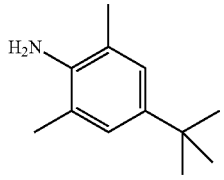 [42014-60-8] | 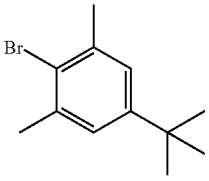 [5345-05-1] | 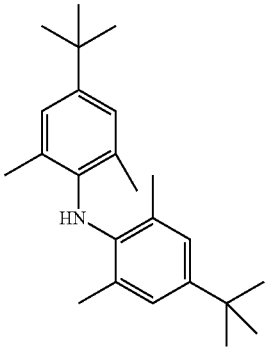 [SMILES: Cc1cc(C(C)(C)C)cc(C)c1Nc1c(C)cc(C(C)(C)C)cc1C] | 48% |
| 12e | 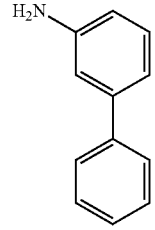 [2243-47-2] | 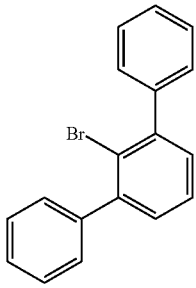 [126866-29-3] | 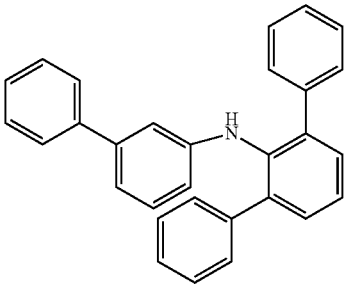 [SMILES: c1ccc(-c2cccc(Nc3c(-c4ccccc4)cccc3-c3ccccc3)c2)cc1] | 56% |
| 12f | 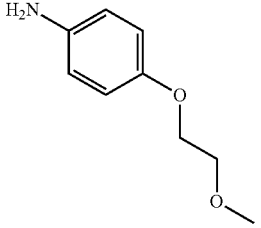 [33311-29-4] | 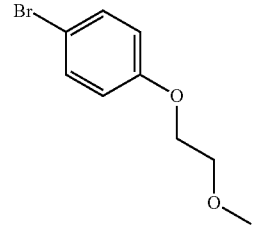 [39255-23-7] | 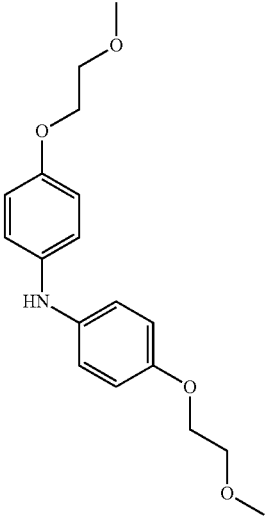 [SMILES: COCCOc1ccc(Nc2ccc(OCCOC)cc2)cc1] | 67% |

| No. | Reactant 10 | Reactant 11 | Product 12 | Yield |
|---|---|---|---|---|
| 12g | [22013-33-8] | [126866-29-3] | | 31% |
| 12h | [63344-48-9] | [60631-83-6] | | 45% |

Stage 2
Preparation of Target Compounds 14a to 14i 5.7 g (11 mmol, 1.0 eq) of 2,7-dibromo-2',7'-dicyano-9,9'-spirobifluorene and 17 g (33 mmol, 3.0 eq) of the amine 12a are initially charged in 100 ml of dry toluene and degassed with argon for 30 minutes. Subsequently, 62 mg (0.28 mmol, 0.025 eq) of palladium(II) acetate and 0.55 ml (0.55 mmol, 0.05 eq) of tri-tert-butylphosphine (1 M in toluene) are added and the mixture is heated under reflux overnight. After the reaction has ended, water is added and the organic phase is removed and washed again with water. Subsequently, the combined aqueous phases are extracted with toluene. The organic phases are dried over sodium sulphate and the solvent is removed on a rotary evaporator. 11.5 g (8.3 mmol, 75%) of a beige solid are obtained, which is purified further by recrystallization with heptane/toluene until an HPLC purity >99.9% is achieved. Finally, the solid is subjected to heat treatment at 300° C. under reduced pressure for five hours. 8.9 g (6.4 mmol, 58%) of the target compound 14a are obtained.

The following are obtained analogously:
| No. | Reactant 12 | Reactant 13 |
|---|---|---|
| 14b | 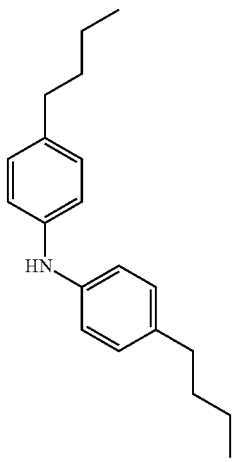 [SMILES: CCCCc1ccc(Nc2ccc(CCCC)cc2)cc1] | 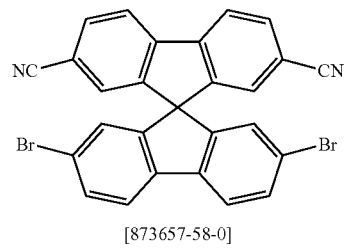 [SMILES: N#Cc1ccc2c(c1)C1(c3cc(Br)ccc3-c3ccc(Br)cc31)c1cc(C#N)ccc1-2]<br>[873657-58-0] |
| 14c | 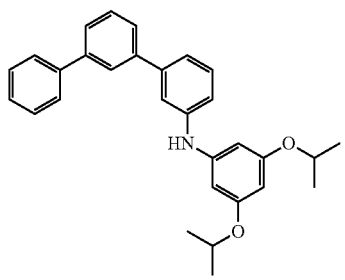 [SMILES: CC(C)Oc1cc(Nc2cccc(-c3cccc(-c4ccccc4)c3)c2)cc(OC(C)C)c1] | 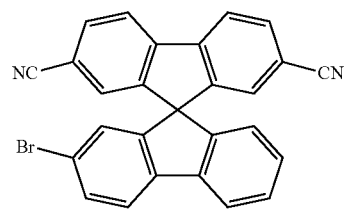<br>[876173-76-1] |
| 14d | 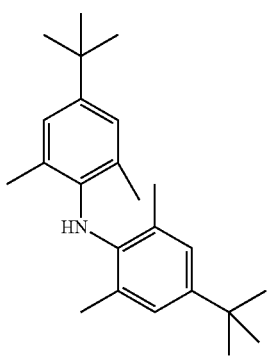 [SMILES: Cc1cc(C(C)(C)C)cc(C)c1Nc1c(C)cc(C(C)(C)C)cc1C] | 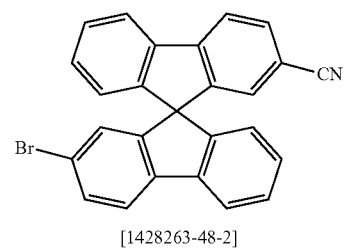 [SMILES: N#Cc1ccc2c(c1)C1(c3ccccc3-c3ccc(Br)cc31)c1ccccc1-2]<br>[1428263-48-2] |
| 14e | 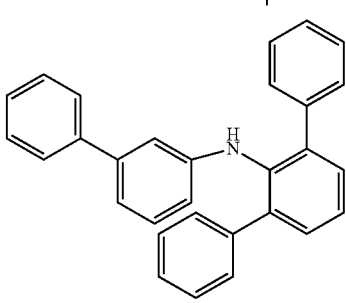 | 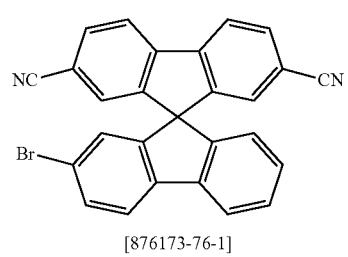 [SMILES: N#Cc1ccc2c(c1)C1(c3ccccc3-c3ccc(Br)cc31)c1cc(C#N)ccc1-2]<br>[876173-76-1] |

-continued
14f
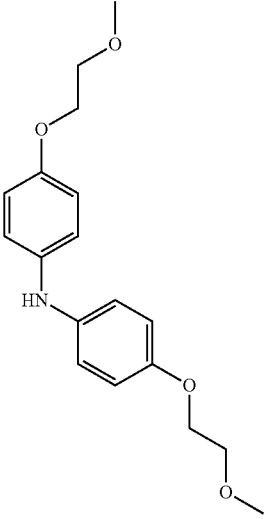 [SMILES: COCCOc1ccc(Nc2ccc(OCCOC)cc2)cc1]
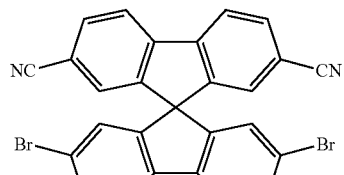
[873657-58-0]
14g
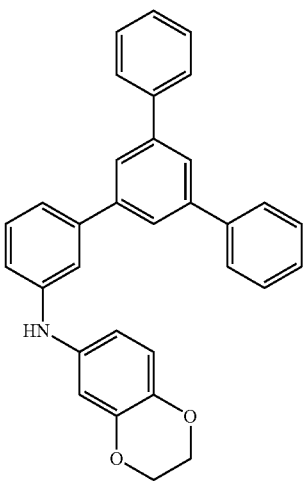 [SMILES: c1ccc(-c2cc(-c3ccccc3)cc(-c3cccc(Nc4ccc5c(c4)OCCO5)c3)c2)cc1]
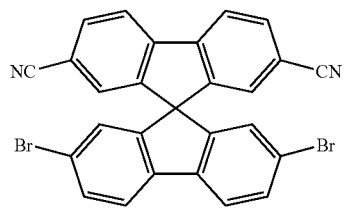
[873657-58-0]
14h
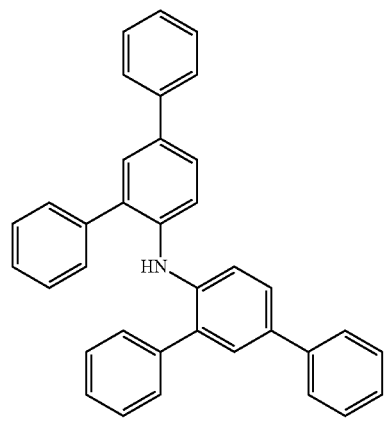 [SMILES: c1ccc(-c2ccc(Nc3ccc(-c4ccccc4)cc3-c3ccccc3)c(-c3ccccc3)c2)cc1]
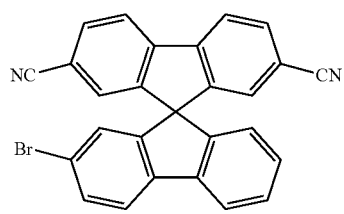
[876173-76-1]

-continued
| 14i | 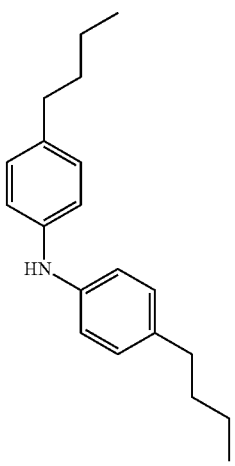 [SMILES: CCCCc1ccc(Nc2ccc(CCCC)cc2)cc1] | 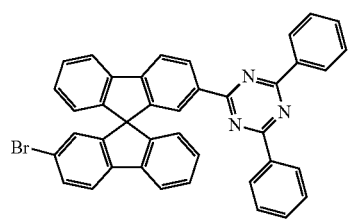 [1421827-56-6] |
| No. | Product 14 | Yield |
|---|---|---|
| 14b | 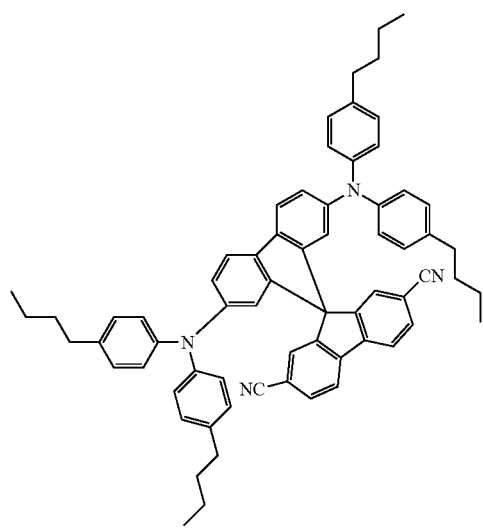 [SMILES: CCCCc1ccc(N(c2ccc(CCCC)cc2)c2ccc3c(c2)C2(c4cc(C#N)ccc4-c4ccc(C#N)cc42)c2cc(N(c4ccc(CCCC)cc4)c4ccc(CCCC)cc4)ccc2-3)cc1] | 58% |
| 14c | 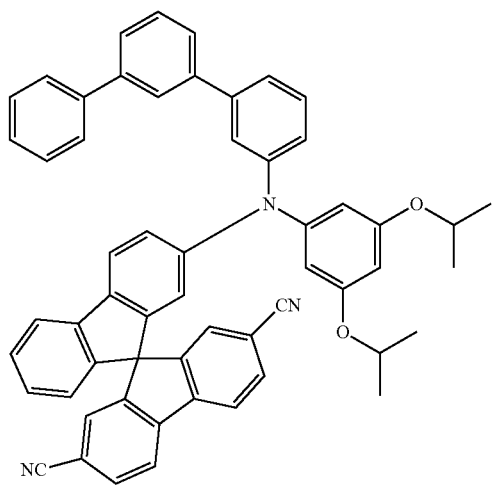 [SMILES: CC(C)Oc1cc(OC(C)C)cc(N(c2cccc(-c3cccc(-c4ccccc4)c3)c2)c2ccc3c(c2)C2(c4ccccc4-3)c3cc(C#N)ccc3-c3ccc(C#N)cc32)c1] | 31% |

-continued
| 14d | 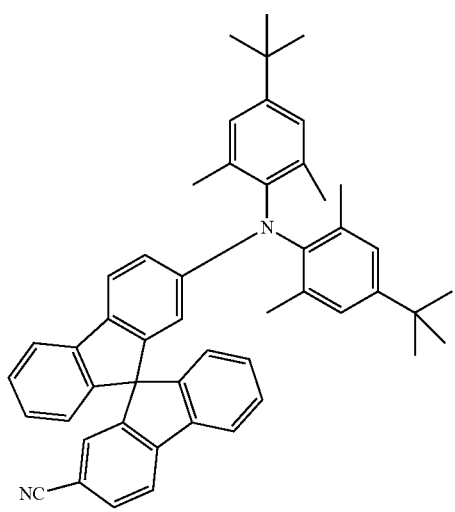 [SMILES: Cc1cc(C(C)(C)C)cc(C)c1N(c1ccc2c(c1)C1(c3ccccc3-c3ccc(C#N)cc31)c1ccccc1-2)c1c(C)cc(C(C)(C)C)cc1C] | 46% |
| 14e | 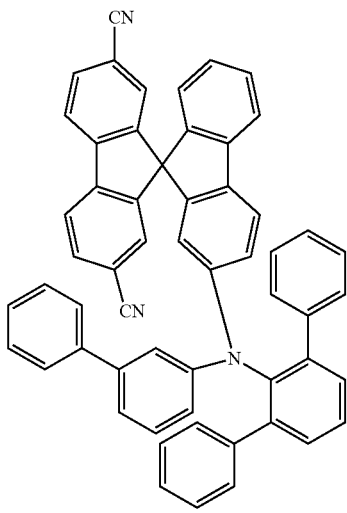 [SMILES: N#Cc1ccc2c(c1)C1(c3ccccc3-c3ccc(N(c4cccc(-c5ccccc5)c4)c4c(-c5ccccc5)cccc4-c4ccccc4)cc31)c1cc(C#N)ccc1-2] | 67% |
| 14f | 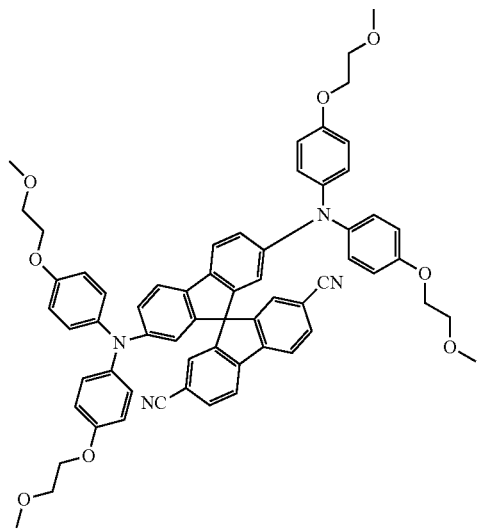 | 18% |

-continued
| | | |
|---|---|---|
| 14g | 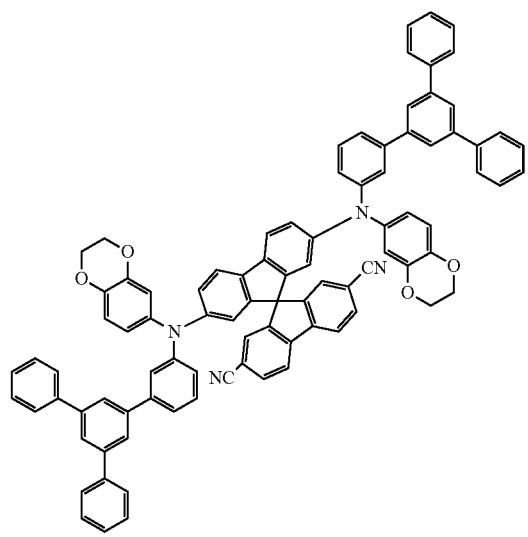 [SMILES: N#Cc1ccc2c(c1)C1(c3cc(C#N)ccc3-2)c2cc(N(c3cccc(-c4cc(-c5ccccc5)cc(-c5ccccc5)c4)c3)c3ccc4c(c3)OCCO4)ccc2-c2ccc(N(c3cccc(-c4cc(-c5ccccc5)cc(-c5ccccc5)c4)c3)c3ccc4c(c3)OCCO4)cc21] | 25% |
| 14h | 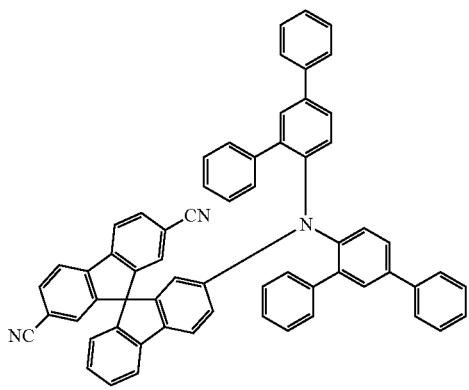 [SMILES: N#Cc1ccc2c(c1)C1(c3ccccc3-c3ccc(N(c4ccc(-c5ccccc5)cc4-c4ccccc4)c4ccc(-c5ccccc5)cc4-c4ccccc4)cc31)c1cc(C#N)ccc1-2] | 49% |
| 14i | 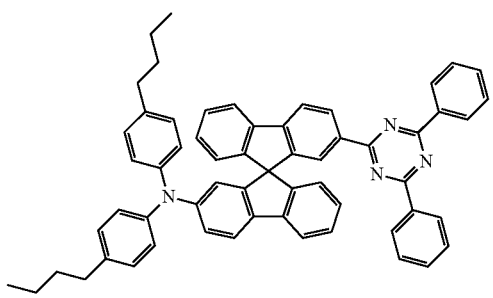 [SMILES: CCCCc1ccc(N(c2ccc(CCCC)cc2)c2ccc3c(c2)C2(c4ccccc4-c4ccc(-c5nc(-c6ccccc6)nc(-c6ccccc6)n5)cc42)c2ccccc2-3)cc1] | 69% |

Example 6

Synthesis of Compounds 19a to 19f

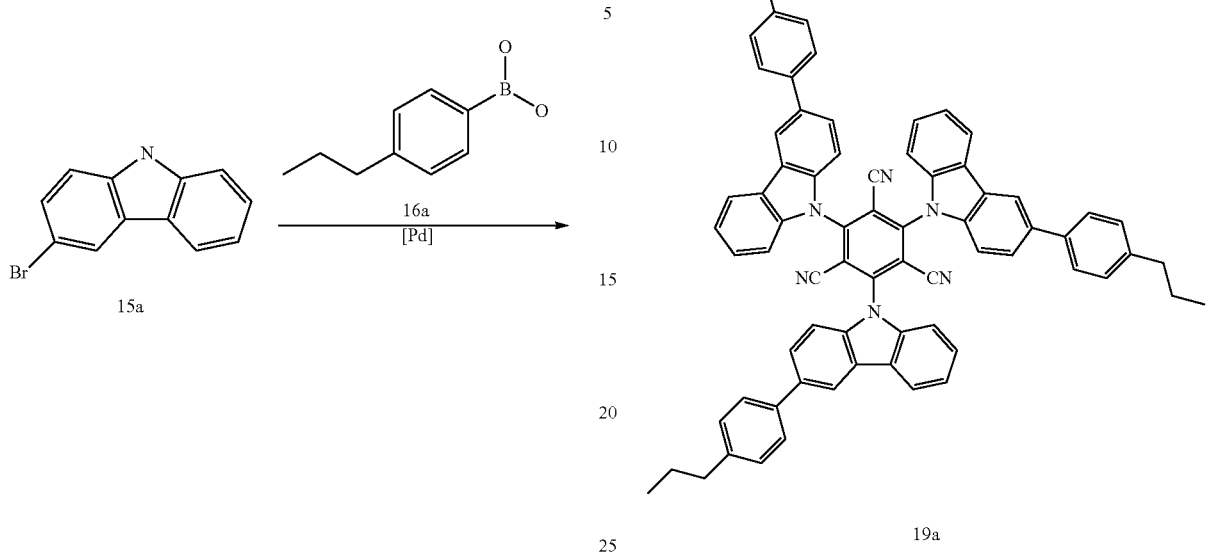

Stage 1

3-(4-Propylphenyl)-9H-carbazole 17a 25 g (100 mmol, 1.0 eq) of 3-bromo-9H-carbazole are initially charged together with 20 g (120 mmol, 1.2 eq) of 4-propylphenylboronic acid [134150-01-9] and 23 g of tripotassium phosphate (106 mmol, 1.06 eq), each in 350 ml of toluene, dioxane and water, and degassed for 30 minutes. Subsequently, 450 mg (2.0 mmol, 0.02 eqα) of palladium(II) acetate and 1.5 g (5.0 mmol, 0.05 eqα) of tri-o-tolylphosphine are added and the reaction mixture is heated to reflux overnight. After the reaction has ended, the organic phase is removed and washed with water. The aqueous phase is extracted with toluene and the combined organic phases are dried over sodium sulphate. The resulting solid is washed with ethanol. After drying, 26 g (91 mmol, 91%) of a pale beige solid 17a are obtained.

The following are prepared analogously;

| No. | Reactant 15 | Reactant 16 | Product 17 | Yield |
|---|---|---|---|---|
| 17b | 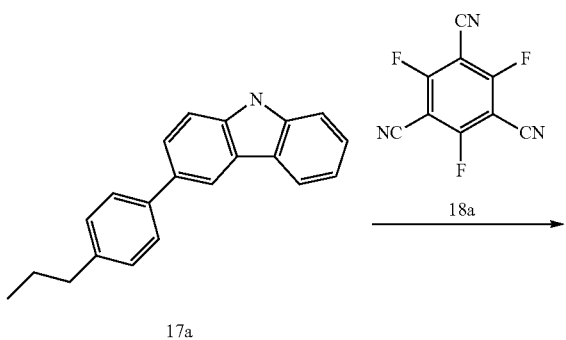 [1592-95-6] | (structure) [1233200-59-3] | (structure) | 88% |

| No. | Reactant 15 | Reactant 16 | Product 17 | Yield |
|---|---|---|---|---|
| 17c | [6825-20-3] | | [1333122-38-5] | 64% |

Stage 2
Synthesis of Target Compound 18a
Variant A:

To a well-stirred suspension of 3.6 g (91 mmol, 4.0 eq) of sodium hydride, 60% by weight dispersion in mineral oil, in 500 ml of THF are added in portions while cooling with ice, at about +10° C., 26 g (91 mmol, 4.0 eq) of compound 17a—Caution! Evolution of hydrogen! Foaming! After the addition has ended, the mixture is stirred for a further 30 minutes and then 6.6 g (23 mmol, 1.0 eq) of 1,3,5-tricyano-2,4,6-trifluorobenzene [363897-9] are added in portions while cooling with ice in such a way that the temperature does not exceed +20° C. After the addition has ended, the mixture is stirred at +10° C. for a further 2 h, then the cooling bath is removed, and the mixture is allowed to warm to 20-25° C., stirred for a further 2 h and then heated to 40° C. for another 12 h. After cooling to room temperature, the reaction is ended by dropwise addition of 30 ml of methanol and the reaction mixture is concentrated almost to dryness under reduced pressure. The residue is subjected to hot extractive stirring twice with 225 ml each time of a mixture of 175 ml of methanol and 50 ml of water and then once with 100 ml of methanol. Purification is effected by repeated recrystallization from heptane/toluene until an HPLC purity of >99.9% is achieved. 4.8 g (4.8 mmol, 21%) of a colourless solid 18a are obtained.

Variant B:

A well-stirred suspension of 3.6 g (91 mmol, 4.0 eq) of carbazole 17a, 6.6 g (23 mmol, 1.0 eq) of 1,3,5-tricyano-2,4,6-trifluorobenzene, 24.4 g (115 mmol, 5.0 eq) of tripotassium phosphate (anhydrous) and 200 g of glass beads in 500 ml of dimethylacetamide is stirred at 160° C. for 16 h. After cooling, 1000 ml of water are added, the precipitated solids are filtered off with suction, and these are washed twice with 300 ml each time of water and twice with 200 ml each time of methanol, and then dried under reduced pressure. Further purification is effected analogously to the purification described in Variant A. Yield: 7.8 g (7.8 mmol, 34%), purity: 99.9% by HPLC.

In an analogous manner, the following compounds are prepared:

| No. | Reactant 17 | Reactant 18 | Product 19 | Yield |
|---|---|---|---|---|
| 19b | [23039-06-7] | [1415349-61-9] | | A 41% |

-continued
| No. | Reactant 17 | Reactant 18 | Product 19 | Yield |
|---|---|---|---|---|
| 19c | 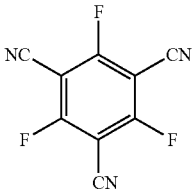 363897-9 | 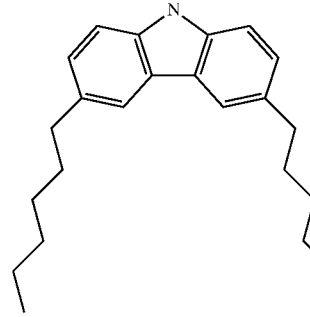 [1131605-21-4] | 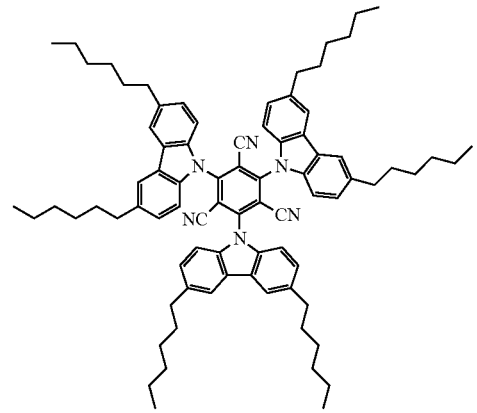 [SMILES: CCCCCCc1ccc2c(c1)c1cc(CCCCCC)ccc1n2-c1c(C#N)c(-n2c3ccc(CCCCCC)cc3c3cc(CCCCCC)ccc32)c(C#N)c(-n2c3ccc(CCCCCC)cc3c3cc(CCCCCC)ccc32)c1C#N] | A 24% |
| 19d | 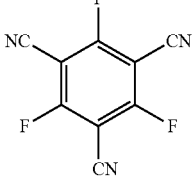 363897-9 | 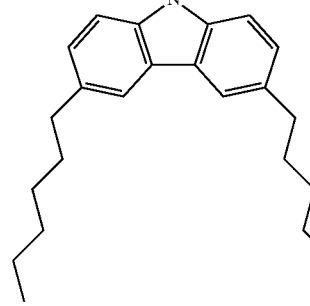 [1131605-21-4] | 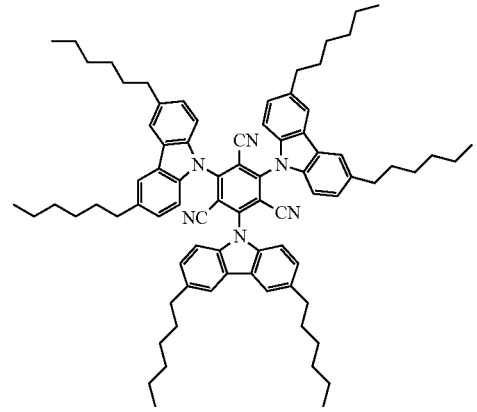 [SMILES: CCCCCCc1ccc2c(c1)c1cc(CCCCCC)ccc1n2-c1c(C#N)c(-n2c3ccc(CCCCCC)cc3c3cc(CCCCCC)ccc32)c(C#N)c(-n2c3ccc(CCCCCC)cc3c3cc(CCCCCC)ccc32)c1C#N] | B 22% |
| 19e | 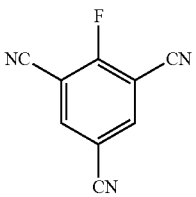 [13519-91-0] | 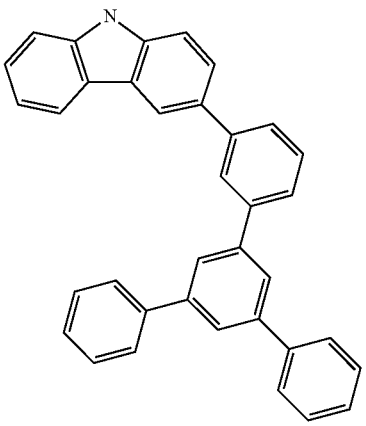 [SMILES: c1ccc(-c2cc(-c3ccccc3)cc(-c3cccc(-c4ccc5[nH]c6ccccc6c5c4)c3)c2)cc1] | 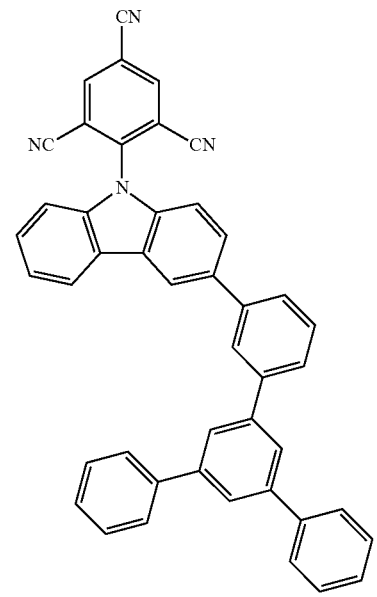 [SMILES: N#Cc1cc(C#N)c(-n2c3ccccc3c3cc(-c4cccc(-c5cc(-c6ccccc6)cc(-c6ccccc6)c5)c4)ccc32)c(C#N)c1] | A 37% |

| No. | Reactant 17 | Reactant 18 | Product 19 | Yield |
|---|---|---|---|---|
| 19f | F, NC, CN [23039-06-7] | (structure) | (structure) | B 14% |

A and B in the Yield column relate to the variants conducted for the different compounds.

Example 7

Solubilities

For good processability from solution, a high solubility in standard solvents is of crucial significance. Standard solutions in toluene applied by means of spin-coating contain a mixture of the OLED-active substances having a total concentration of about 20 mg/ml. In the case of use of higher-boiling solvents, for example mesitylene, it is necessary to use even higher concentrations in order to achieve equal layer thicknesses. If an individual substance has only a solubility of 2 mg/ml in toluene, it is possible to process only mixtures having not more than 10% of this component from solution, and even smaller material proportions still from higher-boiling solvents. A solubility of 5 mg/ml, in contrast, allows the processing of mixtures having up to 25% of this component, and a solubility of 10 mg/ml correspondingly up to 50%.

The solubilities of selected materials can be found in table 1,

TABLE 1

Solubilities of selected materials

| Ex. | Material | Solubility in toluene > 2 mg/ml | Solubility in toluene > 5 mg/ml | Solubility in toluene > 10 mg/ml |
|---|---|---|---|---|
| C1-1 | 20a CAS 1416881-52-1 | yes | no | no |

TABLE 1-continued

Solubilities of selected materials

| Ex. | Material | Solubility in toluene > 2 mg/ml | Solubility in toluene > 5 mg/ml | Solubility in toluene > 10 mg/ml |
|---|---|---|---|---|
| C1-2 | 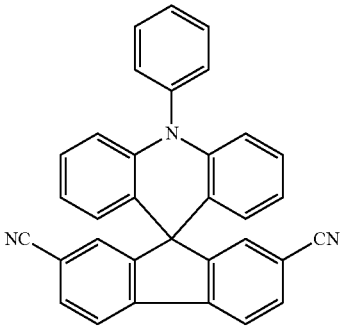  20b  CAS 1206626-92-7 | no | no | no |
| C1-3 | 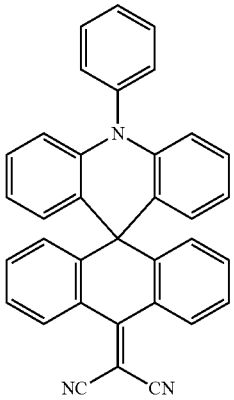  20c  CAS 1418575-73-1 | yes | no | no |
| I1-1 | 6a | yes | yes | no |
| I1-2 | 9a | yes | yes | yes |
| I1-3 | 9e | yes | yes | no |
| I1-4 | 19d | yes | yes | yes |

Example 8

Device Examples

The materials which are required for the examples which follow are shown in table 2. The corresponding HOMO and LUMO energy levels and $S_1$ and $T_1$ are reported in table 3.

OLEDs Having an Emission Layer Processed from Solution

There are already many descriptions of the production of completely solution-based OLEDs in the literature, for example in WO 2004/037887. There have likewise been many previous descriptions of the production of vacuum-based OLEDs, including in WO 2004/058911.

In the examples discussed hereinafter, layers applied in a solution-based and vacuum-based manner were combined within an OLED, and so the processing up to and including the emission layer was effected from solution and in the subsequent layers (hole blocker layer and electron transport layer) from vacuum. For this purpose, the previously described general methods are matched to the circumstances described here (layer thickness variation, materials) and combined as follows:

The general structure is as follows: substrate/ITO (50 nm)/hole injection layer (HIL)/hole transport layer (HTL)/emission layer (EML)/hole blocker layer (HBL)/electron transport layer (ETL)/cathode (aluminium, 100 nm).

Cleaned glass plaques (cleaning in Miele laboratory glass washer, Merck Extran detergent) coated with structured ITO (indium tin oxide) of thickness 50 nm are treated with UV ozone plasma for 20 minutes and then, for better processing, coated with PEDOT:PSS (poly(3,4-ethylenedioxy-2,5-thiophene) polystyrenesulphonate, sourced from Heraeus Precious Metals GmbH & Co. KG, Germany). PEDOT:PSS is spun on from water under air and subsequently baked under air at 180° C. for 10 minutes in order to remove residual water. A crosslinkable hole transport layer is applied to these substrates. It consists of a polymer of the following structural formula:

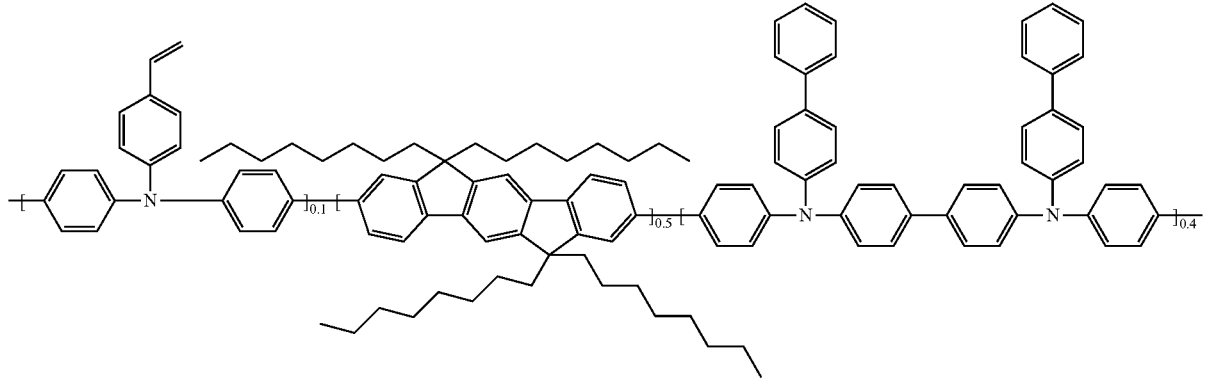

which has been synthesized according to WO 2010/097155. The material is dissolved in toluene. The solids content of the solution is 5 g/l. The layers are spun on in an inert gas atmosphere, argon in the present case, and baked at 180° C. for 60 minutes.

Subsequently, the emission layer is applied. The latter is always composed of at least one matrix material (host material) and an emitting dopant (emitter). Details given in such a form as IC2(60%):WB1(30%):6a(10%) mean that material IC2 is present in a proportion by weight of 60%, WB1 in a proportion by weight of 30% and 6a in a proportion by weight of 10% in the solution from which the emission layer is produced. A corresponding solids mixture for the emission layer is dissolved in toluene. The solids content is 18 g/I. The emission layer is spun on in a nitrogen atmosphere and baked at 180° C. in a nitrogen atmosphere for 10 minutes.

Subsequently, the samples are introduced into a vacuum chamber without contact with air and further layers are applied by thermal evaporation. If such a layer consists of two or more materials, the nomenclature described further up applies to the mixing ratios of the individual components, except that the proportions by weight should be replaced by proportions by volume.

To characterize the OLEDs, current-voltage-luminance characteristics are measured. Luminance is determined with a calibrated photodiode. In addition, the electroluminescence spectrum is measured at a luminance of 1000 cd/m$^2$. Assuming Lambertian radiation characteristics, this is used to calculate the external quantum efficiency (EQE, measured in percent).

Comparative Example C2-1

For the emission layer, a solid mixture of IC2(60%):WB1(30%):20a(10%) is used. This is used as described above to produce a 60 nm-thick emission layer. Subsequently, a 10 nm-thick layer of the material ST1 and then a 40 nm-thick layer of ST1(50%):LiQ(50%) is applied by thermal evaporation under reduced pressure. Subsequently, a 100 nm-thick aluminium layer is applied as cathode by evaporation under reduced pressure.

The OLEDs exhibit green emission, 14.2% EQE at 1000 cd/m$^2$, and require a voltage of 7.4 V for this luminance.

Inventive Example I2-1

The OLED corresponds to Example C2-1, except that, rather than the mixture IC2(60%):WB1(30%):20a(10%), the mixture IC2(60%):WB1(25%):19d(15%) is used.

The OLEDs exhibit green emission, 14.6% EQE at 1000 cd/m$^2$, and require a voltage of 7.3 V for this luminance.

Inventive Example I2-2

The OLED corresponds to Example I2-1, except that the mixture IC2(60%):WB1(20%):19d(20%) is used.

The OLEDs exhibit green emission, 14.9% EQE at 1000 cd/m$^2$, and require a voltage of 8.1 V for this luminance.

Inventive Example I2-3

The OLED corresponds to Example I2-1, except that the mixture IC2(60%):WB1(25%):9a(15%) is used.

The OLEDs exhibit green emission, 12.8% EQE at 1000 cd/m$^2$, and require a voltage of 7.5 V for this luminance.

Inventive Example I2-4

The OLED corresponds to Example I2-1, except that the mixture IC2(60%):WB1(20%):9a(20%) is used.

The OLEDs exhibit green emission, 13.2% EQE at 1000 cd/m$^2$, and require a voltage of 7.7 V for this luminance.

Inventive Example I2-5

The OLED corresponds to Example I2-1, except that the mixture IC2(60%):WB1(25%):9e(15%) is used.

The OLEDs exhibit green emission, 12.5% EQE at 1000 cd/m$^2$, and require a voltage of 7.3 V for this luminance.

Inventive Example I2-6

The OLED corresponds to Example I2-1, except that the mixture IC2(60%):WB1(20%):9e(20%) is used.

The OLEDs exhibit green emission, 13.0% EQE at 1000 cd/m$^2$, and require a voltage of 7.4 V for this luminance.

Inventive Example I2-7

The OLED corresponds to Example I2-1, except that the mixture IC2(60%):WB1(20%):6a(20%) is used.

The OLEDs exhibit greenish blue emission, 10.5% EQE at 1000 cd/m², and require a voltage of 7.2 V for this luminance.

Comparison of the Examples

In the inventive examples, it is found that the use of higher concentrations of the dopant is advantageous particularly for the efficiency of the components produced. These higher concentrations can be achieved only in the case of sufficient solubility of the dopant, which results from use of the inventive materials. Overall, it is possible with the inventive materials to achieve efficient solution-processed OLEDs without the use of transition metal complexes.

TABLE 2

Structural formulae of the materials of the OLEDs

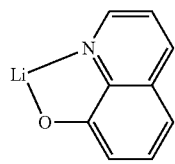

LiQ

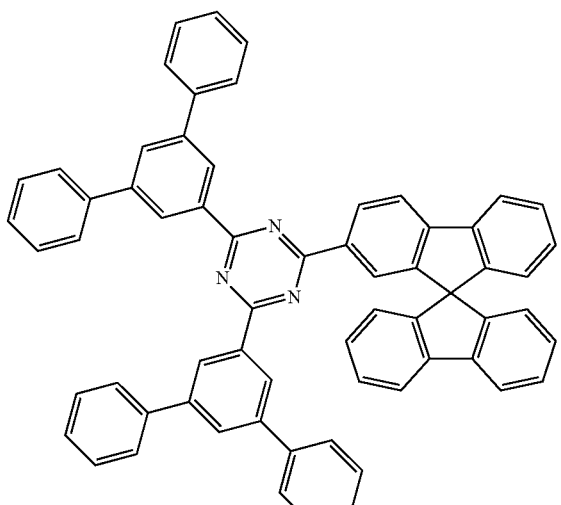

ST1

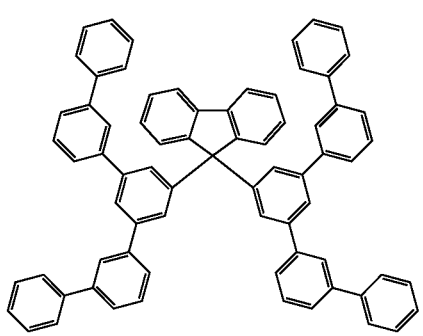

WB1

TABLE 2-continued

Structural formulae of the materials of the OLEDs

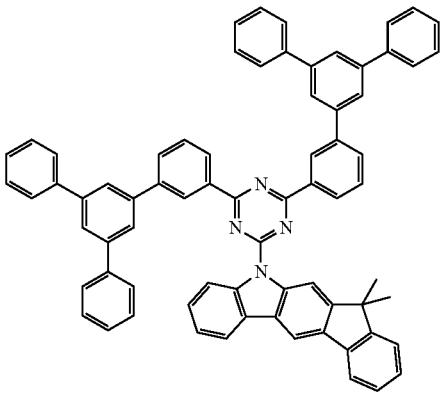

IC2

TABLE 3

HOMO, LUMO, $T_1$, $S_1$ of the relevant materials

| Material | Method | HOMO (eV) | LUMO (eV) | $S_1$ (eV) | $T_1$ (eV) |
|---|---|---|---|---|---|
| IC2 | org. | −5.78 | −2.84 | 3.04 | 2.69 |
| WB1 | org. | −6.16 | −2.24 | 3.38 | 2.95 |
| ST1 | org. | −6.03 | −2.82 | 3.32 | 2.68 |
| LiQ | organomet. | −5.17 | −2.39 | 2.85 | 2.13 |
| 6a | org. | −5.60 | −3.01 | 2.47 | 2.46 |
| 9a | org. | −5.58 | −3.32 | 2.18 | 2.17 |
| 9e | org. | −5.57 | −3.29 | 2.20 | 2.19 |
| 19d | org. | −5.89 | −3.66 | 2.11 | 2.10 |

The invention claimed is:

1. An organic luminescent TADF compound which does not contain any metals and which has a gap between the first excited triplet state ($T_1$) and the first excited singlet state ($S_1$) of not more than 0.15 eV, characterized in that the organic compound contains at least one solubilizing group LG, wherein LG is selected from the following groups, where the groups may have further substitution by one or more identical or different $R^1$ radicals:

Formula (LG-5)

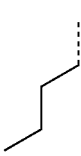

Formula (LG-6)

Formula (LG-7)

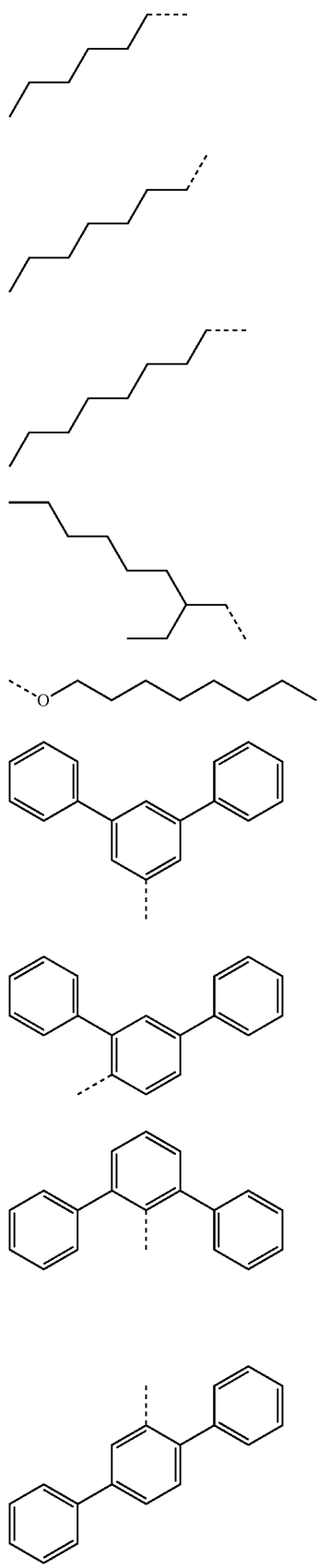
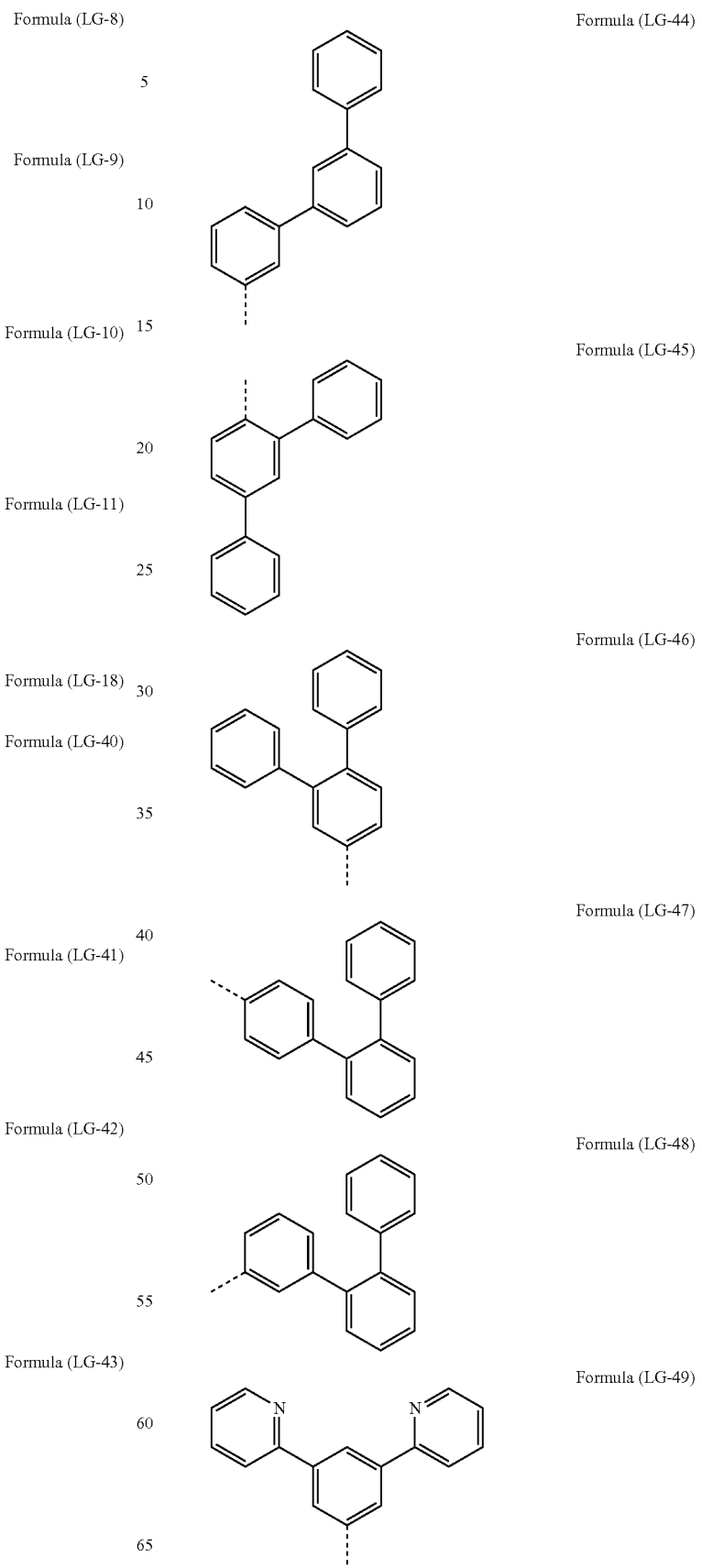

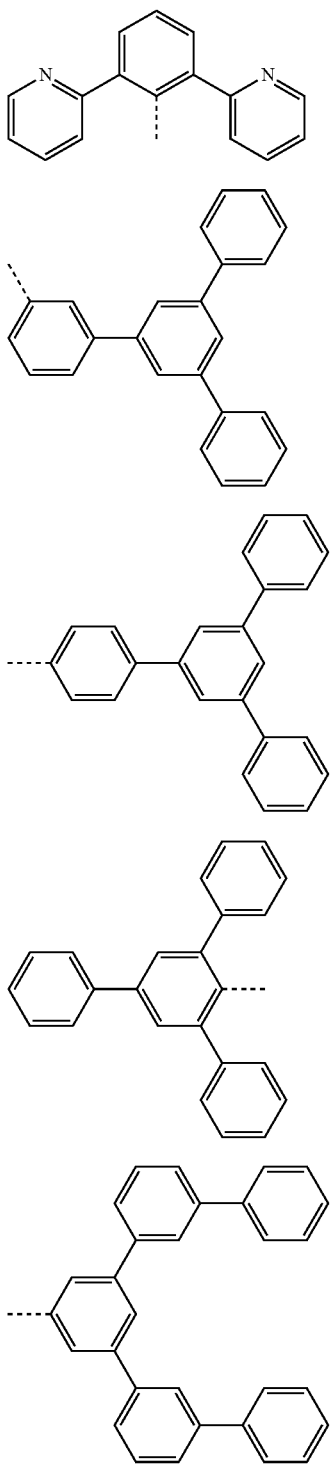

Formula (LG-50)
Formula (LG-51)
Formula (LG-52)
Formula (LG-53)
Formula (LG-54)

and $R^1$ is the same or different at each instance and is hydrogen, a straight-chain alkyl, alkoxy or thioalkoxy group having 1 to 40 carbon atoms or a branched or cyclic alkyl, alkoxy or thioalkoxy group having 3 to 40 carbon atoms or a silyl group or a substituted keto group having 1 to 40 carbon atoms, an alkoxycarbonyl group having 2 to 40 carbon atoms, an aryloxycarbonyl group having 7 to 40 carbon atoms, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where two or more of the $R^1$ groups together may form a mono- or polycyclic, aliphatic or aromatic ring system.

2. The compound according to claim 1, wherein the compound is of the general formula (1)

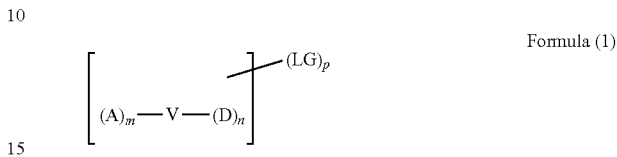

Formula (1)

where the symbols and indices used are as follows:
m is an integer selected from 1, 2, 3, 4 and 5;
n is an integer selected from 1, 2, 3, 4 and 5;
p is an integer greater than or equal to 1;
A is an acceptor group which may be substituted by one or more $R^1$ radicals which may be the same or different at each instance;
D is a donor group which may be substituted by one or more $R^1$ radicals which may be the same or different at each instance;
LG is as defined in claim 1;
V is any organic bridge between the A and D groups or a single bond, where, when V is a single bond, either m or n is 1, where V may be substituted by one or more $R^1$ radicals which may be the same or different at each instance;
$R^1$ is the same or different at each instance and is hydrogen, a straight-chain alkyl, alkoxy or thioalkoxy group having 1 to 40 carbon atoms or a branched or cyclic alkyl, alkoxy or thioalkoxy group having 3 to 40 carbon atoms or a silyl group or a substituted keto group having 1 to 40 carbon atoms, an alkoxycarbonyl group having 2 to 40 carbon atoms, an aryloxycarbonyl group having 7 to 40 carbon atoms, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where two or more of the $R^1$ groups together may form a mono- or polycyclic, aliphatic or aromatic ring system.

3. The compound according to claim 2, wherein
p is an integer from 1 to 4;
$R^1$ is the same or different at each instance and is hydrogen, a straight-chain alkyl, alkoxy or thioalkoxy group having 1 to 40 carbon atoms or a branched or cyclic alkyl, alkoxy or thioalkoxy group having 3 to 40 carbon atoms or a silyl group or a substituted keto group having 1 to 40 carbon atoms, an alkoxycarbonyl group having 2 to 40 carbon atoms, an aryloxycarbonyl group having 7 to 40 carbon atoms, a crosslinkable group or a substituted or unsubstituted aromatic or heteroaromatic ring system having 5 to 60 ring atoms, or an aryloxy or heteroaryloxy group having 5 to 60 ring atoms, or a combination of these systems, where two or more of the $R^1$ groups together may form a mono- or polycyclic, aliphatic or aromatic ring system, and when no two or more of the $R^1$ groups together can form a mono- or polycyclic, aliphatic or aromatic ring system.

4. The compound according to claim 1, wherein the TADF compound is an organic compound having a molecular weight of not more than 5000 g/mol.

5. The compound according to claim 1, wherein the TADF compound is an organic compound having a molecular weight of not more than 1000 g/mol.

6. The compound according to claim 1, wherein the A group contains a cyano, oxo or nitrile group or a pyrimidine or a pyrazine.

7. The compound according to claim 1, wherein the D group contains a diarylamino, diarylheteroarylamino, carbazole, indenocarbazole or indolocarbazole group.

8. The compound according to claim 1, wherein the bridge V is selected from the following formulae which may be substituted by one or more $R^1$ radicals which may be the same or different at each instance:

Formula (V-1)

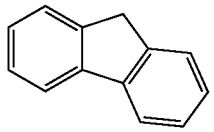
Formula (V-2)

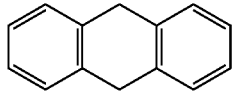
Formula (v-3)

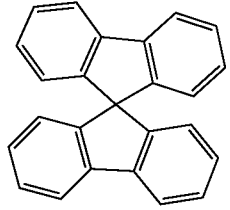
Formula (V-4)

Formula (V-5)

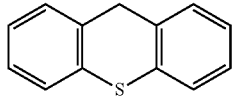
Formula (V-6)

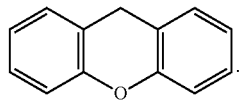
Formula (V-7)

9. The compound according to claim 1, wherein the compound contains at least 2, aromatic rings.

10. A composition comprising one or more of the compounds according to claim 1 and one or more functional materials selected from the group of the electron-conducting materials (ETM), electron-injecting materials (EIM), electron-blocking materials (EBM), hole-conducting materials (HTM), hole-injecting materials (HIM), hole-blocking materials (HBM), fluorescent emitters, phosphorescent emitters, matrix materials and inorganic nanoparticles.

11. The composition according to claim 8, wherein the composition comprises two matrix materials.

12. A formulation comprising at least one compound according to claim 1 and at least one solvent.

13. A process for producing an organic electronic device which comprises producing at least one layer of the electronic device from solution with the aid of the formulation according to claim 12.

14. An organic electronic device which comprises at least one compound according to claim 1.

15. The organic electronic device as claimed in claim 14, wherein the device is an organic light-emitting diode (OLED) or organic light-emitting electrochemical cell (OLEC, LEEC, LEC).

16. The device according to claim 14, wherein the device is selected from organic integrated circuits (OICs), organic field-effect transistors (OFETs), organic thin-film transistors (OTFTs), organic electroluminescent devices, organic solar cells (OSCs), organic optical detectors or organic photoreceptors.

17. The device according to claim 14, wherein the device is an organic electroluminescent device selected from the group consisting of the organic light-emitting transistors (OLETs), organic field quench devices (OFQDs), organic light-emitting electrochemical cells (OLETs, LECs, LEECs), organic laser diodes (O-lasers) and organic light-emitting diodes (OLEDs).

18. An organic electroluminescent device comprising at least one compound according to claim 1 in an emission layer.

* * * * *